(12) United States Patent
Conner et al.

(10) Patent No.: US 7,674,950 B2
(45) Date of Patent: Mar. 9, 2010

(54) PLANT REGULATORY SEQUENCES FOR SELECTIVE CONTROL OF GENE EXPRESSION

(75) Inventors: Timothy W. Conner, Chesterfield, MO (US); Patrice Dubois, Quebec (CA); Marianne Malven, Ellisville, MO (US); James D. Masucci, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 413 days.

(21) Appl. No.: 10/325,107

(22) Filed: Dec. 20, 2002

(65) Prior Publication Data

US 2003/0165947 A1    Sep. 4, 2003

(51) Int. Cl.
*A01H 5/00*     (2006.01)
*C12N 15/82*    (2006.01)
*C07H 21/04*    (2006.01)

(52) U.S. Cl. .................. 800/287; 800/298; 435/419; 536/24.1

(58) Field of Classification Search ................. 800/295; 435/320.1; 536/23.1
See application file for complete search history.

(56) References Cited

OTHER PUBLICATIONS

Kim et al. Plant Mol Biol 1994. vol. 24, pp. 105-117.*
Bilodeau et al. Plant Cell Reports. 1994. vol. 14. pp. 125-130.*
Benfey et al., "The CaMV 35S enhancer contains at least two domains which can confer different developmental and tissue-specific expression patterns," *The EMBO J.*, 8(8):2195-2202, 1989.
Cho et al., "Regulation of root hair initiation and expansin gene expression in arabidopsis," *The Plant Cell*, 14:3237-3253, 2002.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Molecular Biology*, 38:655-662, 1998.
Welsch et al., "Structural and functional characterization of the phytoene synthase promoter from arabidopsis thaliana," *Planta*, 216:523-534, 2003.

* cited by examiner

*Primary Examiner*—Elizabeth F McElwain
(74) *Attorney, Agent, or Firm*—Erin C. Robert, Esq.; Sonnenschein Nath & Rosenthal LLP

(57) ABSTRACT

Promoters from male reproductive tissues are isolated from corn and wheat. These promoters can be used in plants to regulate transcription of target genes including genes for control of fertility, insect or pathogen tolerance, herbicide tolerance or any gene of interest.

12 Claims, 2 Drawing Sheets

PLANT REGULATORY SEQUENCES FOR SELECTIVE CONTROL OF GENE EXPRESSION

FIELD OF THE INVENTION

The present invention relates to the isolation and use of nucleic acid molecules for control of gene expression in plants, specifically novel plant promoters.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al., 1995, World Journal of Microbiology and Biotechnology 11: 449-460). Particularly desirable traits or qualities of interest for plant genetic engineering would include, but are not limited to, resistance to insects, fungal diseases, and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous gene sequence that confers the desired phenotype when expressed in the plant is introduced into the plant cell. The vector also includes a plant promoter that is operably linked to the heterologous gene sequence, often a promoter not normally associated with the heterologous gene. The vector is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

Because the promoter is a regulatory element that plays an integral part in the overall expression of a gene or gene(s), it would be advantageous to have a variety of promoters to tailor gene expression such that a gene or gene(s) is transcribed efficiently at the right time during plant growth and development, in the optimal location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing that can be caused by recombination of homologous sequences. In light of these and other considerations, it is apparent that optimal control of gene expression and regulatory element diversity are important in plant biotechnology.

The proper regulatory sequences must be present and in the proper location with respect to the DNA sequence of interest for the newly inserted DNA to be transcribed and thereby, if desired, translated into a protein in the plant cell. These regulatory sequences include, but are not limited to, a promoter, a 5' untranslated leader, and a 3' polyadenylation sequence. The ability to select the tissues in which to transcribe such foreign DNA and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range or tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. Other classes of promoters would include, but are not limited to, inducible promoters that can be triggered by external stimuli such as chemical agents, developmental stimuli, or environmental stimuli. Thus, the different types of promoters desired can be obtained by isolating the regulatory regions of DNA sequences that are transcribed and expressed in a constitutive, tissue-enhanced, or inducible manner.

The technological advances of high-throughput sequencing and bioinformatics have provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced, and the expressed sequences can be catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue-enhanced sequence can then be used as a probe or primer to clone the corresponding full-length cDNA. A genomic library of the target plant can then be used to isolate the corresponding gene and the associated regulatory elements, including but not limited to promoter sequences.

Multiple genes that have a desired expression profile such as in male reproductive tissues can be isolated by selectively comparing cDNA libraries of target tissues of interest with non-target or background cDNA libraries to find the 5' regulatory regions associated with the expressed sequences in those target libraries. The promoter sequences can be isolated from the genomic DNA flanking the desired genes. The isolated promoter sequences can be used for selectively modulating expression of any operatively linked gene and provide additional regulatory element diversity in a plant expression vector in gene stacking approaches.

SUMMARY OF THE INVENTION

The present invention provides isolated plant promoter sequences that comprise nucleic acid regions located upstream of the 5' end of plant DNA structural coding sequences that are transcribed in male reproductive tissues. The plant promoter sequences are capable of modulating or initiating transcription of DNA sequences to which they are operably linked.

The present invention provides nucleic acid sequences comprising regulatory sequences as shown in SEQ ID NOs: 35-62 that are located upstream of the 5' end of plant DNA structural coding sequences and transcribed in male reproductive tissues.

In one aspect, the present invention provides nucleic acid sequences comprising a sequence selected from the group consisting of SEQ ID NOs: 35-62 or any fragments or regions of the sequence or cis elements of the sequence that are capable of regulating transcription of operably linked DNA sequences.

The present invention also provides nucleic acid sequences comprising a sequence selected from the group consisting of SEQ ID NOs: 35-62 that are promoters.

Another aspect of the present invention relates to the use of one or more cis elements, or fragments thereof of the disclosed 5' promoter sequences that can be combined to create novel promoters or used in a novel combination with another heterologous regulatory sequence to create a chimeric promoter capable of modulating transcription of an operably linked DNA sequence.

Hence, the present invention relates to the use of nucleic acid sequences disclosed in SEQ ID NOs: 35-62 or any fragment, region, or cis element of the disclosed sequences that are capable of regulating transcription of a DNA sequence when operably linked to the DNA sequence. Therefore, the invention not only encompasses the sequences as disclosed in SEQ ID NOs: 35-62, but also includes any truncated or deletion derivatives, or fragments or regions thereof that are capable of functioning independently as a promoter including cis elements that are capable of functioning as regulatory sequences in conjunction with one or more regulatory sequences when operably linked to a transcribable sequence.

The present invention thus encompasses a novel promoter or chimeric or hybrid promoter comprising a nucleic acid of SEQ ID NOs: 35-62. The chimeric or hybrid promoters can consist of any length fragments, regions, or cis elements of the disclosed sequences of SEQ ID NOs: 35-62 combined with any other transcriptionally active minimal or full-length promoter. For example, a promoter sequence selected from SEQ ID NOs: 35-62 may be combined with a CaMV 35S or other promoter to construct a novel chimeric promoter. A minimal promoter can also be used in combination with the nucleic acid sequences of the present invention. A novel promoter also comprises any promoter constructed by engineering the nucleic acid sequences disclosed in SEQ ID NOs: 35-62 or any fragment, region, or cis element of the disclosed sequences in any manner sufficient to transcribe an operably linked DNA sequence.

Another aspect of the present invention relates to the ability of the promoter sequences of SEQ ID NOs: 35-62, or fragments, regions, or cis elements thereof to regulate transcription of operably linked transcribable sequences in male reproductive tissues. Fragments, regions, or cis elements of SEQ ID NOs: 35-62 that are capable of regulating transcription of operably linked DNA sequences in certain tissues may be isolated from the disclosed nucleic acid sequences of SEQ ID NOs: 35-62 and used to engineer novel promoters.

The present invention also encompasses DNA constructs comprising the disclosed sequences as shown in SEQ ID NOs: 35-62 or any fragments, regions, or cis elements thereof, including novel promoters generated using the disclosed sequences or any fragment, region, or cis element of the disclosed sequences.

The present invention also includes any transgenic cells and plants containing the DNA disclosed in the sequences as shown in SEQ ID NOs: 35-62, or any fragments, regions, or cis elements thereof.

The present invention also provides a method of regulating transcription of a DNA sequence comprising operably linking the DNA sequence to any promoter comprising a nucleic acid comprising all or any fragment, region or cis element of a sequence selected from the group consisting of SEQ ID NOs: 35-62.

In another embodiment the present invention provides a method of regulating expression of DNA sequences in male reproductive tissues by operably linking a sequence selected from the group consisting of SEQ ID NOs: 35-62, or any fragment, region, or cis element of the disclosed sequences to any transcribable DNA sequence. The fragments, regions, or cis elements of the disclosed promoters as shown in SEQ ID NOs: 35-62 can be engineered and used independently in novel combinations including multimers, or truncated derivatives and the novel promoters can be operably linked with a transcribable DNA sequence. Alternatively the disclosed fragments, regions, or cis elements of the disclosed sequences can be used in combination with a heterologous promoter including a minimal promoter to create a novel chimeric or hybrid promoter and the novel chimeric promoter can be operably linked to a transcribable DNA sequence.

The present invention also provides a method of making a transgenic plant by introducing into a cell of a plant a DNA construct comprising: (i) a promoter comprising a nucleic acid comprising a sequence selected from the group consisting of SEQ ID NOs: 35-62, or fragment, region, or cis element thereof, and operably linked to the promoter, (ii) a transcribable DNA sequence and (iii) a 3' untranslated region.

The present invention also provides a method of isolating at least one 5' regulatory sequence of a desired expression profile from a target plant of interest by evaluating a collection of nucleic acid sequences of ESTs derived from one or more cDNA libraries prepared from a plant cell type of interest, comparing EST sequences from at least one target plant cDNA library and one or more non-target cDNA libraries of ESTs from a different plant cell type, subtracting common EST sequences found in both target and non-target libraries, designing gene-specific primers from the remaining ESTs after the subtraction that are representative of the targeted expressed sequences, and isolating the corresponding 5' flanking and regulatory sequences, that include promoter sequences from a genomic library prepared from the target plant using the gene specific primers.

The present invention also provides a method of isolating at least one 5' regulatory sequence of a desired expression profile from a target plant of interest by evaluating a collection of nucleic acid sequences of ESTs derived from one or more cDNA libraries from a plant cell type of interest, immobilizing these ESTs on a nylon membrane or glass chip, and hybridizing the ESTs with labeled probes to identify those ESTs from genes that have a desired expression profile and isolating the corresponding 5' flanking and regulatory sequences, that include promoter sequences from a genomic library prepared from the target plant using the gene specific primers.

The present invention also provides a method of isolating at least one 5' regulatory sequence of a desired expression profile from a target plant of interest by constructing a subtracted library consisting of cDNA clones from a plant cell type of interest and subtracting by hybridization those cDNA clones which are also present in non-target plant tissues, isolating clones of the subtracted library and isolating the corresponding 5' flanking and regulatory sequences, that include promoter sequences from a genomic library prepared from the target plant using the gene specific primers.

The foregoing and other aspects of the invention will become more apparent from the following detailed description and accompanying drawings.

BRIEF DESCRIPTION OF THE SEQUENCE LISTING

Figure 1:
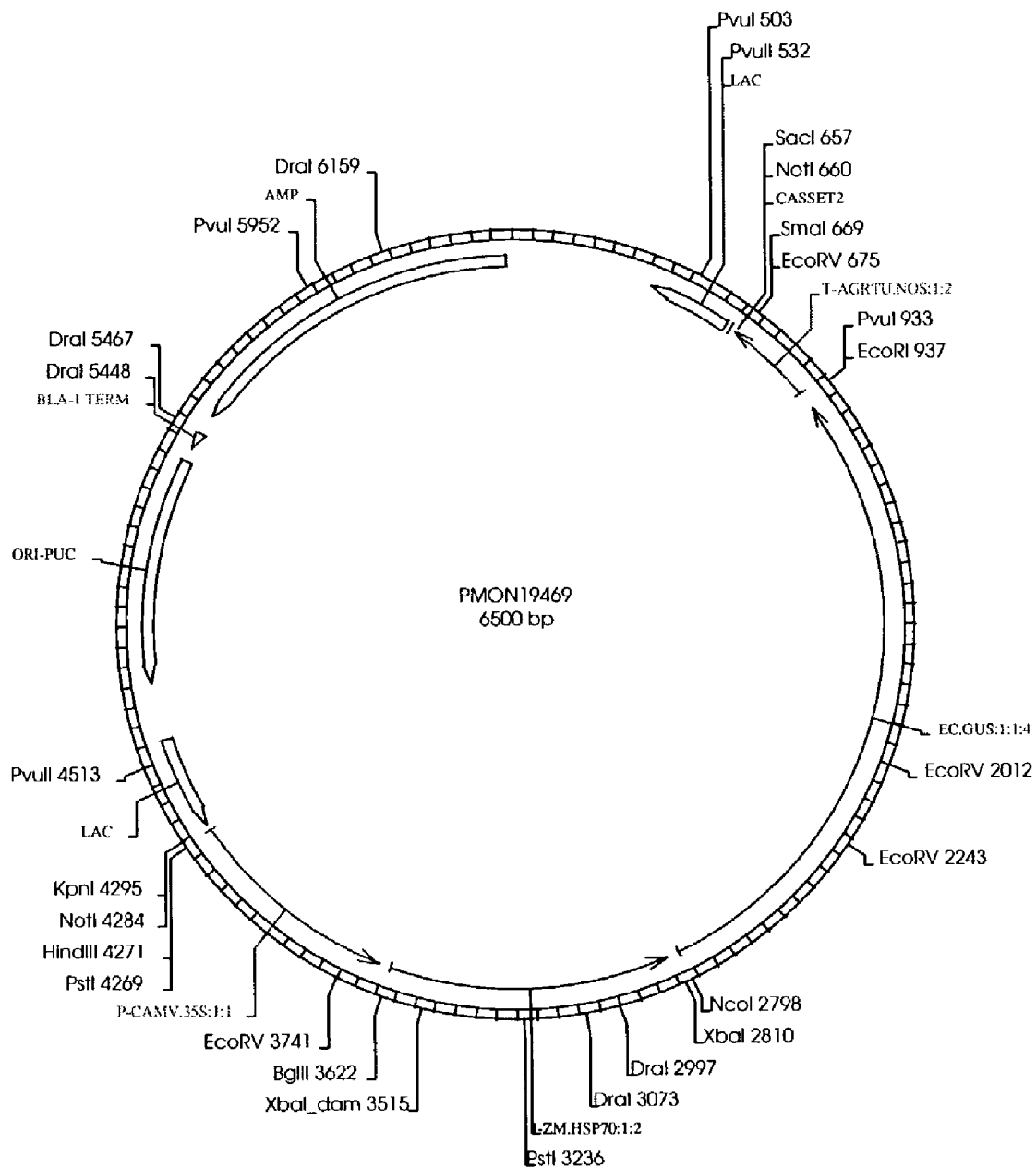
FIG. 1 is a plasmid map of pMON19469.

SEQ ID NOs: 1-3 are adaptor primer sequences.
SEQ ID NOs: 4-24 are fully synthesized primers derived from known maize (*Zea mays*) sequences.
SEQ ID NOs: 25-34 are fully synthesized primers derived from known wheat (*Triticum aestivum*) sequences.
SEQ ID NOs: 35-55 are promoter sequences isolated from maize (*Zea mays*).
SEQ ID NOs: 56-57 are promoter sequences isolated from wheat (*Triticum aestivum*). SEQ ID NOs: 58-62 are promoter sequences isolated from maize (*Zea mays*).
SEQ ID NOs: 63-68 are fully synthesized primers derived from known maize (*Zea mays*) sequences.

DETAILED DESCRIPTION OF THE INVENTION

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. The nomenclature for DNA bases as set forth at 37 CFR §1.822 is used. The standard one- and three-letter nomenclature for amino acid residues is used.

"Nucleic acid (sequence)", "nucleotide sequence" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence that originates from a foreign source or species or, if from the same source, is modified from its original form.

An "isolated" nucleic acid sequence is substantially separated or purified away from other nucleic acid sequences that the nucleic acid is normally associated with in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

The term "substantially purified", as used herein, refers to a molecule separated from substantially all other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantial identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman (Adv. Appl. Math. 2: 482, 1981); by the homology alignment algorithm of Needleman and Wunsch (J. Mol. Biol. 48:443, 1970); by the search for similarity method of Pearson and Lipman (Proc. Natl. Acad. Sci. USA 85:2444, 1988); preferably by computerized implementations of these algorithms (GAP, BESTFIT, FASTA, and TFASTA) in the Wisconsin Genetics Software Package Release 7.0 (Genetics Computer Group, 575 Science Dr., Madison, Wis.). The reference nucleic acid may be a full-length molecule or a portion of a longer molecule. Alternatively, two nucleic acids have substantial identity if one hybridizes to the other under stringent conditions, as defined below.

A first nucleic acid sequence is "operably linked" with a second nucleic acid sequence when the sequences are so arranged that the first nucleic acid sequence affects the function of the second nucleic acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., *Molecular Cloning: A Laboratory Manual*, 2nd ed., vol. 1-3, ed. Sambrook et al., Cold Spring Harbor Laboratory Press, Cold Spring Harbor, N.Y., 1989; *Current Protocols in Molecular Biology*, ed. Ausubel et al., Greene Publishing and Wiley-Interscience, New York, 1992, with periodic updates, 1992; and *PCR Protocols: A Guide to Methods and Applications*, Academic Press: San Diego, Innis et al., 1990). Methods for chemical synthesis of nucleic acids are discussed, for example, in Beaucage and Carruthers (Tetra. Letts. 22: 1859-1862, 1981), and Matteucci et al. (J. Am. Chem. Soc. 103:

3185, 1981). Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Host cells often display a preferred pattern of codon usage (Murray et al., 1989). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc. (University of Wisconsin Biotechnology Center, Madison, Wis.).

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and by Innis et al. (*PCR Protocols: A Guide to Methods and Applications*, Academic Press, San Diego, 1990). In PCR, a primer refers to a short oligonucleotide of defined sequence that is annealed to a DNA template to initiate the polymerase chain reaction.

"Transformed", "transfected", or "transgenic" refers to a cell; tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

"Transcriptional profiling" refers to a method where the expression of many genes is monitored in parallel. Gene sequences, usually in the form of cDNA sequences or EST sequences are immobilized on either glass or nylon membranes (Schena, et al., Science 270: 467-470, 1995; Drmanac, et al., Genomics 37: 29-40, 1996). Labeled probes, typically cDNA made from total RNA or mRNA isolated from a particular tissue or tissues are used to hybridized with the immobilized DNA. Because a large number of DNA fragments can be placed on the arrays, the hybridization allows for the determination of parallel gene expression studies (Ramsay, Nature Biotechnology 16 (1) 40-44, 1998). The identification of tissue specific genes can be accomplished by immobilizing a large number of EST sequences that have been isolated from a specific library or libraries and hybridizing that array with probes derived from different tissues (Ruan, et al., The Plant Journal 15 (6): 821-833, 1998). Analysis of the results can uncover genes that are highly expressed in the desired tissue but are not detected or detected at low levels in undesired tissues. The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to, promoter regions, 5' untranslated leaders, introns, genes, 3' untranslated regions, and other regulatory sequences or sequences that affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association of nucleic acid sequences by base-pairing (A-G-T pairs with the complementary sequence A-C-T). Complementarity between two single-stranded molecules may be partial, if only some of the nucleic acids pair are complementary, or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"ESTs" or "Expressed Sequence Tags" are short sequences of randomly selected clones from a cDNA (or complementary DNA) library that are representative of the cDNA inserts of these randomly selected clones (McCombie et al., Nature Genetics, 1: 124, 1992; Kurata et al., Nature Genetics, 8: 365, 1994; Okubo et al., Nature Genetics, 2: 173, 1992).

The term "electronic Northern" refers to a computer-based sequence analysis that allows sequences from multiple cDNA libraries to be compared electronically based on parameters the researcher identifies including abundance in EST populations in multiple cDNA libraries, or exclusively to EST sets from one or combinations of libraries.

"Electronic subsetting", also known as "electronic subtraction", refers to a method of comparing electronically nucleic acid sequences from different or multiple sources that can be used to assess the expression profile of the nucleic acid sequences that reflects gene transcription activity and message stability in a particular tissue, at a particular time, or under particular conditions.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example, by chemical compounds (chemical inducers) or in response to environmental, hormonal, chemical, or developmental signals. Inducible or regulated promoters include, for example, promoters regulated by light, heat, stress, flooding or drought, phytohormones, wounding, or chemicals such as ethanol, jasmonate, salicylic acid, or safeners.

Any plant promoter can be used as a 5' regulatory sequence for modulating expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50: 349-383, 1981; Messing et al., In: Genetic Engineering of Plants, Kosuge et al., eds, pp. 211-227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds, pp. 211-227, 1983). In addition, virtually all promoters include additional upstream activating sequences or enhancers (Benoist and Chambon, Nature 290: 304-310, 1981; Gruss et al., Proc. Natl. Acad. Sci. USA 78: 943-947, 1981; and Khoury and Gruss, Cell 27: 313-314, 1983) extending from around −100 bp to −1,000 bp or more upstream of the transcription initiation site. Enhancers have also been found 3' to the transcriptional start site.

When fused to heterologous DNA sequences, such promoters typically cause the fused sequence to be transcribed in a manner that is similar to that of the gene sequence that the promoter is normally associated with. Promoter fragments that include regulatory sequences can be added (for example, fused to the 5' end of, or inserted within, an active promoter having its own partial or complete regulatory sequences (Fluhr et al., Science 232: 1106-1112, 1986; Ellis et al., EMBO J. 6: 11-16, 1987; Strittmatter and Chua, Proc. Nat. Acad. Sci. USA 84: 8986-8990, 1987; Poulsen and Chua, Mol. Gen. Genet. 214: 16-23, 1988; Comai et al., Plant Mol. Biol. 15: 373-381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232: 1106-1112, 1986; Strittmatter and Chua, Proc. Nat. Acad. Sci. USA 84: 8986-8990, 1987; Aryan et al., Mol. Gen. Genet. 225: 65-71, 1991).

Promoters are typically comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84: 8986-8990, 1987; Ellis et al., EMBO J. 6: 11-16, 1987; Benfey et al., EMBO J. 9: 1677-1684, 1990). Cis elements bind trans-acting protein factors that regulate transcription. Some cis elements bind more than one factor, and trans-acting transcription factors may interact with different affinities with more than one cis element (Johnson and McKnight, Ann. Rev. Biochem. 58: 799-839, 1989). Plant transcription factors, corresponding cis elements, and analysis of their interaction are discussed, for example, in Martin (Curr. Opinions Biotech. 7: 130-138, 1996), Murai (*Methods in Plant Biochemistry and Molecular Biology*, Dashek, ed., CRC Press, 1997, pp. 397-422), and Maliga et al. (*Methods in Plant Molecular Biology*, Cold Spring Harbor Press, 1995, pp. 233-300). The promoter sequences of the present invention can contain "cis elements" that can confer or modulate gene expression.

Cis elements can be identified by a number of techniques, including deletion analysis, i.e., deleting one or more nucleotides from the 5' end or internal to a promoter; DNA binding protein analysis using DNAse I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, *Methods in Plant Biochemistry and Molecular Biology*, Dashek, ed., CRC Press, 1997, pp. 397-422; and *Methods in Plant Molecular Biology*, Maliga et al., eds, Cold Spring Harbor Press, 1995, pp. 233-300).

Cis elements can be obtained by chemical synthesis or by cloning from promoters that include such elements, and they can be synthesized with additional flanking sequences that contain useful restriction enzyme sites to facilitate subsequent manipulation. In one embodiment, the promoters are comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84: 8986-8990, 1987; Ellis et al., EMBO J. 6:11-16, 1987; Benfey et al., EMBO J. 9: 1677-1684, 1990). In a preferred embodiment, sequence regions comprising "cis elements" of the nucleic acid sequences of SEQ ID NOs: 35-62 are identified using computer programs designed specifically to identify cis elements, or domains or motifs within sequences.

The present invention includes cis elements of SEQ ID NOs: 35-62, or homologues of cis elements known to affect gene regulation that show homology with the nucleic acid sequences of the present invention. A number of such elements are known in the literature, such as elements that are regulated by numerous factors such as light, heat, or stress; elements that are regulated or induced by pathogens or chemicals, and the like. Such elements may either positively or negatively regulated gene expression, depending on the conditions. Examples of cis elements would include, but are not limited to, oxygen responsive elements (Cowen et al., J. Biol. Chem. 268(36): 26904, 1993), light regulatory elements (see for example, Bruce and Quail, Plant Cell 2(11): 1081, 1990; and Bruce et al., EMBO J. 10: 3015, 1991), a cis element responsive to methyl jasmonate treatment (Beaudoin and Rothstein, Plant Mol. Biol. 33: 835, 1997), salicylic acid responsive elements (Strange et al., Plant J. 11: 1315, 1997), heat shock response elements (Pelham et al., Trends Genet. 1: 31, 1985), elements responsive to wounding and abiotic stress (Loace et al., Proc. Natl. Acad. Sci. U.S.A. 89:9230, 1992; Mhiri et al., Plant Mol. Biol. 33: 257, 1997), low temperature elements (Baker et al., Plant Mol. Biol. 24: 701, 1994; Jiang et al., Plant Mol. Biol. 30: 679, 1996; Nordin et al., Plant Mol. Biol. 21: 641, 1993; Zhou et al., J. Biol. Chem. 267: 23515, 1992), and drought responsive elements, (Yamaguchi et al., Plant Cell 6: 251-264, 1994; Wang et al., Plant Mol. Biol. 28: 605, 1995; Bray, Trends in Plant Science 2: 48, 1997).

The present invention therefore encompasses fragments or cis elements of the disclosed nucleic acid molecules, and such nucleic acid fragments can include any region of the disclosed sequences. The promoter regions or partial promoter regions of the present invention as shown in SEQ ID NOs: 35-62 can contain one or more regulatory elements including but not limited to cis elements or domains that are capable of regulating expression of operably linked DNA sequences, preferably in male reproductive tissues.

Plant promoters can include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11-16, 1987; Strittmatter and Chua, Proc. Nat. Acad. Sci. USA 84: 8986-8990, 1987; Poulsen and Chua, Mol. Gen. Genet. 214: 16-23, 1988; Comai et al., Plant. Mol. Biol. 15: 373-381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232: 1106-1112, 1986; Strittmatter and Chua, Proc. Nat. Acad. Sci. USA 84: 8986-8990, 1987; Aryan et al., Mol. Gen. Genet. 225: 65-71, 1991).

The design, construction, and use of chimeric or hybrid promoters comprising one or more of cis elements of SEQ ID NOs: 35-62 for modulating or regulating the expression of operably linked nucleic acid sequences is also encompassed by the present invention.

The promoter sequences, fragments, regions or cis elements thereof of SEQ ID NOs: 35-62 are capable of transcribing operably linked DNA sequences in male reproductive tissues and therefore can selectively regulate expression of genes in these tissues.

The promoter sequences of the present invention are useful for regulating gene expression in male reproductive tissues such as tassels, anthers, and pollen. For a number of agronomic traits, transcription of a gene or genes of interest is desirable in multiple tissues in order to confer the desired characteristic(s). The availability of suitable promoters that regulate transcription of operably linked genes in selected target tissues of interest is important because it may not be desirable to have expression of a gene in every tissue, but only in certain tissues. For example, if one desires to selectively express a target gene for controlling fertility in corn, it would be advantageous to have a promoter that confers enhanced expression in reproductive tissues. The promoter sequences of the present invention are capable of regulating operably linked DNA sequence particularly in male reproductive tissues and have utility for regulating transcription of any target gene including, but not limited to, genes for control of fertility, insect or pathogen tolerance, herbicide tolerance or any gene of interest. Consequently, it is important to have a wide variety of choices of 5' regulatory elements for any plant biotechnology strategy.

The advent of genomics, which comprises molecular and bioinformatics techniques, has resulted in rapid sequencing and analyses of a large number of DNA samples from a vast number of targets, including but not limited to plant species of agronomic importance. To identify the nucleic acid sequences of the present invention from a database or collection of cDNA sequences, the first step involves constructing cDNA libraries from specific plant tissue targets of interest. Briefly, the cDNA libraries are first constructed from these tissues that are harvested at a particular developmental stage or under particular environmental conditions. By identifying differentially expressed genes in plant tissues at different developmental stages or under different conditions, the corresponding regulatory sequences of those genes can be identified and isolated. Transcript imaging enables the identification of tissue-preferred sequences based on specific imaging of nucleic acid sequences from a cDNA library. By transcript imaging as used herein is meant an analysis that compares the abundance of expressed genes in one or more libraries. The clones contained within a cDNA library are sequenced and the sequences compared with sequences from publicly available databases. Computer-based methods allow the researcher to provide queries that compare sequences from multiple libraries. The process enables quick, identification of clones of interest compared with conventional hybridization subtraction methods known to those of skill in the art.

Using conventional methodologies, cDNA libraries can be constructed from the mRNA (messenger RNA) of a given tissue or organism using poly dT primers and reverse transcriptase (Efstratiadis et al., Cell 7: 279, 1976; Higuchi et al., Proc. Natl. Acad. Sci. U.S.A. 73: 3146, 1976; Maniatis et al., Cell 8: 163, 1976; Land et al., Nucleic Acids Res. 9: 2251, 1981; Okayama et al., Mol. Cell. Biol. 2: 161, 1982; Gubler et al., Gene 25: 263, 1983).

Several methods can be employed to obtain full-length cDNA constructs. For example, terminal transferase can be used to add homopolymeric tails of dC residues to the free 3' hydroxyl groups (Land et al., Nucleic Acids Res. 9: 2251, 1981). This tail can then be hybridized by a poly dG oligo that can act as a primer for the synthesis of full-length second strand cDNA. Okayama and Berg reported a method for obtaining full-length cDNA constructs (Mol. Cell Biol. 2: 161, 1982). This method has been simplified by using synthetic primer adapters that have both homopolymeric tails for priming the synthesis of the first and second strands and restriction sites for cloning into plasmids (Coleclough et al., Gene 34: 305, 1985) and bacteriophage vectors (Krawinkel et al., Nucleic Acids Res. 14: 1913, 1986; Han et al., Nucleic Acids Res. 15: 6304, 1987).

These strategies can be coupled with additional strategies for isolating rare mRNA populations. For example, a typical mammalian cell contains between 10,000 and 30,000 different mRNA sequences (Davidson, Gene Activity in Early Development, 2nd ed., Academic Press, New York, 1976). The number of clones required to achieve a given probability that a low-abundance mRNA will be present in a cDNA library is $N=(\ln(1-P))/(\ln(1-1/n))$ where N is the number of clones required, P is the probability desired, and 1/n is the fractional proportion of the total mRNA that is represented by a single rare mRNA (Sambrook et al., 1989).

One method to enrich preparations of mRNA for sequences of interest is to fractionate by size. One such method is to fractionate by electrophoresis through an agarose gel (Pennica et al., Nature 301: 214, 1983). Another method employs sucrose gradient centrifugation in the presence of an agent, such as methylmercuric hydroxide, that denatures secondary structure in RNA (Schweinfest et al., Proc. Natl. Acad. Sci. U.S.A. 79: 4997-5000, 1982).

A frequently adopted method is to construct equalized or normalized cDNA libraries (Ko, Nucleic Acids Res. 18: 5705, 1990; Patanjali et al., Proc. Natl. Acad. Sci. U.S.A. 88: 1943, 1991). Typically, the cDNA population is normalized by subtractive hybridization (Schmid et al., J. Neurochem. 48: 307, 1987; Fargnoli et al., Anal. Biochem. 187: 364, 1990; Travis et al., Proc. Natl. Acad. Sci. U.S.A. 85: 1696, 1988; Kato, Eur. J. Neurosci. 2: 704, 1990; Schweinfest et al., Genet. Anal. Tech. Appl. 7: 64, 1990). Subtraction represents another method for reducing the population of certain sequences in the cDNA library (Swaroop et al., Nucleic Acids Res. 19: 1954, 1991). Normalized libraries can be constructed using the Soares procedure (Soares et al., Proc. Natl. Acad. Sci. U.S.A. 91: 9228, 1994). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected, and clones for rare transcripts are effectively increased in abundance.

ESTs can be sequenced by a number of methods. Two basic methods can be used for DNA sequencing, the chain termination method (Sanger et al., Proc. Natl. Acad. Sci. U.S.A. 74: 5463, 1977) and the chemical degradation method (Maxam and Gilbert, Proc. Nat. Acad. Sci. U.S.A. 74: 560, 1977). Automation and advances in technology, such as the replacement of radioisotopes with fluorescence-based sequencing, have reduced the effort required to sequence DNA (Craxton, Methods, 2: 20, 1991; Ju et al., Proc. Natl. Acad. Sci. U.S.A. 92: 4347, 1995; Tabor and Richardson, Proc. Natl. Acad. Sci. U.S.A. 92: 6339, 1995). Automated sequencers are available from a number of manufacturers including Pharmacia Biotech, Inc., Piscataway, N.J. (Pharmacia ALF); LI-COR, Inc., Lincoln, Nebr. (LI-COR 4,000); and Millipore, Bedford, Mass. (Millipore BaseStation).

ESTs longer than 150 bp have been found to be useful for similarity searches and mapping (Adams et al., Science 252: 1651, 1991). EST sequences normally range from 150-450 bases. This is the length of sequence information that is routinely and reliably generated using single run sequence data. Typically, only single run sequence data is obtained from the cDNA library (Adams et al., Science 252:1651, 1991). Automated single run sequencing typically results in an approximately 2-3% error or base ambiguity rate (Boguski et al., Nature Genetics, 4: 332, 1993).

EST databases have been constructed or partially constructed from, for example, *C. elegans* (McCombrie et al., Nature Genetics 1:124, 1992), human liver cell line HepG2 (Okubo et al., Nature Genetics 2:173, 1992), human brain RNA (Adams et al., Science 252:1651, 1991; Adams et al., Nature 355: 632, 1992), Arabidopsis (Newman et al., Plant Physiol. 106: 1241, 1994) and rice (Kurata et al., Nature Genetics 8: 365, 1994). The present invention uses ESTs from a number of cDNA libraries prepared from male reproductive tissues of corn as a tool for the identification of genes expressed in these target tissues, which then facilitates the isolation of 5' regulatory sequences such as promoters that regulate the genes.

Computer-based sequence analyses can be used to identify differentially expressed sequences including, but not limited to, those sequences expressed in one tissue compared with another tissue. For example, a different set of sequences can be found from cDNA isolated from root tissue versus leaf tissue. Accordingly, sequences can be compared from cDNA libraries prepared from plants grown under different environmental or physiological conditions. Once the preferred sequences are identified from the cDNA library of interest, the genomic clones can be isolated from a genomic library prepared from the plant tissue, and corresponding regulatory sequences including but not limited to 5' regulatory sequences can be identified and isolated.

In one preferred embodiment, expressed sequence tags (EST) sequences from a variety of cDNA libraries are catalogued in a sequence database. This database is used to identify promoter targets from a particular tissue of interest. The selection of expressed sequence tags for subsequent promoter isolation is reflective of the presence of one or more sequences among the representative ESTs from a random sampling of an individual cDNA library or a collection of cDNA libraries. For example, the identification of regulatory sequences that direct the expression of transcripts in male reproductive tissues is conducted by identifying ESTs found in tissues such as tassel and anther, and absent or in lower abundance in other cDNA libraries in the database. The identified EST leads are then evaluated for relative abundance within the library and the expression profile for a given EST is assessed. By abundance as used herein is meant the number of times a clone or cluster of clones appears in a library. The sequences that are enhanced or in high abundance in a specific tissue or organ that represent a target expression profile are identified in this manner and primers can be designed from the identified EST sequences. A PCR-based approach can be used to amplify flanking regions from a genomic library of the target plant of interest. A number of methods are known to those of skill in the art to amplify unknown DNA sequences adjacent to a core region of known sequence. Methods include but are not limited to inverse PCR (IPCR), vectorette PCR, Y-shaped PCR, and genome walking approaches.

In a preferred embodiment, genomic DNA ligated to an adaptor is subjected to a primary round of PCR amplification with a gene-specific primer and a primer that anneals to the adaptor sequence. The PCR product is next used as the template for a nested round of PCR amplification with a second gene-specific primer and second adaptor. The resulting fragments from the nested PCR reaction are then isolated, purified and subcloned into an appropriate vector. The fragments are sequenced, and the translational start sites can be identified when the EST is derived from a truncated cDNA. The fragments can be cloned into plant expression vectors as transcriptional or translational fusions with a reporter gene such as β-glucuronidase (GUS). The constructs can be tested in transient analyses, and subsequently the 5' regulatory regions are operably linked to other genes and regulatory sequences of interest in a suitable plant transformation vector and the transformed plants are analyzed for the expression of the gene(s) of interest, by any number of methods known to those of skill in the art.

Any plant can be selected for the identification of genes and regulatory sequences. Examples of suitable plant targets for the isolation of genes and regulatory sequences would include but are not limited to Acadia, alfalfa, apple, apricot, Arabidopsis, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lily, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugar-cane, sunflower, sweet potato, sweetgum, tangerine, tea, tobacco, tomato, triticale, turf, turnip, a vine, watermelon, wheat, yams, and zucchini. Particularly preferred plant targets would include corn, cotton, rice, soybean, and wheat.

The nucleic acid molecules of the present invention are isolated from corn (*Zea mays*) or wheat (*Triticum aesitivum*). The corn plant develops about 20-21 leaves, silks about 65 days post-emergence, and matures about 125 days post-emergence. Normal corn plants follow a general pattern of development, but the time interval between different stages and morphology varies between different hybrids, growth and environmental conditions.

There are a number of identifiable stages in corn plant development. The stages are defined as vegetative (V) and reproductive (R) stages. Subdivisions of the V stages are numerically designated as V1, V2, V3, etc., through V(n) where (n) represents the last leaf stage before tasseling (VT) and the first V stage is the emergence (VE) stage. For example, VE is the emergence from the soil of a seedling leaf, V1 represents the first true leaf, V2 represents the second leaf, etc. The reproductive stages include the first appearance of silk to the mature seed and are represented as follows: R1 is silking, R2 is blistering, R3 is the milk stage, R4 is the dough stage, R5 is the dent stage, and R6 is physiological maturity (see for example, Ritchie et al., *How a Corn Plant Develops*, Iowa State University of Science and Technology Cooperative Extension Service, Ames, Iowa 48: 1-21, 1986).

Any type of plant tissue can be used as a target tissue for the identification of genes and associated regulatory sequences. For the present invention, corn or wheat male reproductive tissue is used. More preferably corn anther tissues or wheat anther tissues are the target tissues for identification of promoter sequences. Corn cDNA libraries can be constructed from several different plant developmental stages. More preferably corn plants at stages V6-V9 are used or wheat plants at Feekes stage 10. Background or non-target libraries can include but are not limited to libraries such as leaf, root, embryo, callus, shoot, seedling, endosperm, culm, ear, and silks.

Any method that allows a differential comparison between different types or classes of sequences can be used to isolate genes or regulatory sequences of interest. For example, in one differential screening approach, a cDNA library from mRNA isolated from a particular tissue can be prepared in a bacteriophage host using a commercially available cloning kit. The plaques are spread onto plates containing lawns of a bacterial host such as *E. coli* to generate bacteriophage plaques. About $10^5$-$10^6$ plaques can be lifted onto DNA-binding membranes. Duplicate membranes are probed using probes generated from mRNA from the target and non-target or background tissue. The probes are labeled to facilitate detection after hybridization and development. Plaques that hybridize to target tissue-derived probes but not to non-target tissue derived probes that display a desired differential pattern of expression can be selected for further analysis. Genomic DNA libraries can also be prepared from a chosen species by partial digestion with a restriction enzyme and size selecting the DNA fragments within a particular size range. The genomic DNA can be cloned into a suitable vector including but not limited to a bacteriophage and prepared using a suitable vector such as a bacteriophage using a suitable cloning kit from any number of vendors (see for example Stratagene, La Jolla, Calif., or Gibco BRL, Gaithersburg, Md.).

Differential hybridization techniques as described are well known to those of skill in the art and can be used to isolate a desired class of sequences. By classes of sequences as used herein is meant sequences that can be grouped based on a common identifier including but not limited to sequences isolated from a common target plant, a common library, or a common plant tissue type. In a preferred embodiment, sequences of interest are identified based on sequence analyses and querying of a collection of diverse cDNA sequences from libraries of different tissue types. The disclosed method provides an example of a differential screening approach based on electronic sequence analyses of plant ESTs derived from diverse cDNA libraries.

A number of methods used to assess gene expression are based on measuring the mRNA level in an organ, tissue, or cell sample. Typical methods include but are not limited to RNA blots, ribonuclease protection assays and RT-PCR. In another preferred embodiment, a high-throughput method is used whereby regulatory sequences are identified from a transcript profiling approach. The development of cDNA microarray technology enables the systematic monitoring of gene expression profiles for thousands of genes (Schena et al, Science, 270: 467, 1995). This DNA chip-based technology arrays thousands of cDNA sequences on a support surface. These arrays are simultaneously hybridized to multiple labeled cDNA probes prepared from RNA samples of different cell or tissue types, allowing direct comparative analysis of expression. This technology was first demonstrated by analyzing 48 Arabidopsis genes for differential expression in roots and shoots (Schena et al, Science, 270:467, 1995). More recently, the expression profiles of over 1400 genes were monitored using cDNA microarrays (Ruan et al, The Plant Journal 15:821, 1998). Microarrays provide a high-throughput, quantitative and reproducible method to analyze gene expression and characterize gene function. The transcript profiling approach using microarrays thus provides another valuable tool for the isolation of regulatory sequences such as promoters associated with those genes.

The present invention uses high throughput sequence analyses to form the foundation of rapid computer-based identification of sequences of interest. Those of skill in the art are aware of the resources available for sequence analyses. Sequence comparisons can be done by determining the similarity of the test or query sequence with sequences in publicly available or proprietary databases ("similarity analysis") or by searching for certain motifs ("intrinsic sequence analysis") (e.g., cis elements) (Coulson, Trends in Biotechnology, 12: 76, 1994; Birren et al., Genome Analysis, 1: 543, 1997).

The nucleotide sequences provided in SEQ ID NOs: 35-62 or fragments thereof, or complements thereof, or a nucleotide sequence at least 90% identical, preferably 95% identical even more preferably 99% or 100% identical to the sequence provided in SEQ ID NOs: 35-62 or fragment thereof, or complement thereof, can be "provided" in a variety of mediums to facilitate use. Such a medium can also provide a subset thereof in a form that allows one of skill in the art to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable media can be used to create a manufacture comprising computer readable medium having recorded thereon a nucleotide sequence of the present invention.

By providing one or more of nucleotide sequences of the present invention, those of skill in the art can routinely access the sequence information for a variety of purposes. Computer software is publicly available that allows one of skill in the art to access sequence information provided in a computer readable medium. Examples of public databases would include but are not limited to the DNA Database of Japan (DDBJ) (http://www.ddbj.nig.ac.jp/); Genbank (http://www.ncbi.nlm.nih.gov/web/Genbank/Index.html); and the European Molecular Biology Laboratory Nucleic Acid Sequence Database (EMBL) (http://www.ebi.ac.uk/ebi_docs/embl_db.html) or versions thereof. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology, 12: 76-80, 1994; Birren et al., Genome Analysis, 1: 543, 1997).

Any program designed for motif searching also has utility in the present invention. Sequence analysis programs designed for motif searching can be used for identification of cis elements. Preferred computer programs would include but are not limited to MEME, SIGNAL SCAN, and GENESCAN. MEME is a program that identifies conserved motifs (either nucleic acid or peptide) in a group of unaligned sequences. MEME saves these motifs as a set of profiles. These profiles can be used to search a database of sequences. A MEME algorithm (Version 2.2) can be found in version 10.0 of the GCG package; MEME (Bailey and Elkan, Machine Learning, 21(1-2): 51-80, 1995 and the location of the website is http://www.sdsc.edu/MEME/meme/website/COPYRIGHT.html. SIGNALSCAN is a program that identifies known motifs in the test sequences using information from other motif databases (Prestridge, CABIOS 7, 203-206, 1991). SIGNALSCAN version 4.0 information is available at the following website: http://biosci.cbs.umn.edu/software/sigscan.html. The ftp site for SIGNALSCAN is ftp://biosci.cbs.umn.edu/software/sigscan.html. Databases used with SIGNALSCAN include PLACE (http://www.dna.affrc.go.ip/htdocs/PLACE; Higo et al., Nucleic Acids Research 27(1): 297-300, 1999) and TRANSFAC (Heinemeye et al., Nucleic Acid Research 27(1): 318-322) that can be found at the following website: http://transfac.gbf.de/. GENESCAN is another suitable program for motif searching (Burge and Karlin, J. Mol. Biol. 268: 78-94, 1997), and information on Version 1.0 is available at the following website: http://gnomic.stanford.edu/GENESCANW.html. As used herein, "a target structural motif" or "target motif" refers to any rationally selected sequence or combination of sequences in which the sequence(s) are chosen based on a three-dimensional configuration that is formed upon the folding of the target motif. There are a variety of target motifs known to those of skill in the art. Protein target motifs include, but are not limited to, enzymatic active sites and signal sequences. Preferred target motifs of the present invention would include but are not limited to promoter sequences, cis elements, hairpin structures and other expression elements such as protein binding sequences.

As used herein, "search means" refers to one or more programs that are implemented on the computer-based system to compare a target sequence or target structural motif with the sequence information stored within the data storage means. Search means are used to identify fragments or regions of the sequences of the present invention that match a particular target sequence or target motif. Multiple sequences can also be compared in order to identify common regions or motifs that may be responsible for specific functions. For example, cis elements or sequence domains that confer a specific expression profile can be identified when multiple promoter regions of similar classes of promoters are aligned and analyzed by certain software packages.

The present invention further provides systems, particularly computer-based systems, which contain the sequence information described herein. As used herein, a "computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. Those of skill in the art can appreciate that any one of the available computer-based systems are suitable for use in the present; invention.

SEQ ID NOs: 4-34 and SEQ ID NOs: 63-68 are primers designed from the cDNA sequences identified from the computer-based sequence comparisons. These sequences are used to extend the nucleic acid sequence using polymerase chain reaction (PCR) amplification techniques (see for example, Mullis et al., Cold Spring Harbor Symp. Quant. Biol. 51: 263, 1986; Erlich et al., European Patent Appln. EP50,424, EP84,796, EP258,017, EP 237,362; 201,184, U.S. Pat. Nos. 4,683,202, 4,582,788, and 4,683,194). A number of PCR amplification methods are known to those of skill in the art and are used to identify nucleic acid sequences adjacent to a known sequence. For example, inverse PCR (IPCR) methods to amplify unknown DNA sequences adjacent to a core region of known sequence have been described. Other methods are also available such as capture PCR (Lagerstrom et al., PCR Methods Applic. 1: 111, 1991), and walking PCR (Parker et al., Nucleic Acids Res 19: 3055, 1991). A number of manufacturers have also developed kits based on modifications of these methods for the purposes of identifying sequences of interest. Technical advances including improvements in primer and adaptor design, improvements in the polymerase enzyme, and thermocycler capabilities have facilitated quicker, more efficient methods for isolating sequences of interest.

In a preferred embodiment, the flanking sequences containing the 5' regulatory elements of the present invention are isolated using a genome-walking approach (Universal GenomeWalker™ Kit, CLONTECH Laboratories, Inc., Palo Alto, Calif.). In brief, the purified genomic DNA is subjected to a restriction enzyme digest that produces genomic DNA fragments with ends that are ligated with GenomeWalker™ adaptors. GenomeWalker™ primers are used along with gene specific primers in two consecutive PCR reactions (primary and nested PCR reactions) to produce PCR products containing the 5' regulatory sequences that are subsequently cloned and sequenced.

In addition to their use in modulating gene expression, the promoter sequences of the present invention also have utility as probes or primers in nucleic acid hybridization experiments. The nucleic acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure (see for example Sambrook et al., at 9.52-9.55 and 9.47-9.52, 9.56-9.58, 1989; Kanehisa, Nucl. Acids Res. 12: 203-213, 1984; Wetmur and Davidson, J. Mol. Biol. 31:349-370, 1968). Appropriate stringency conditions that promote DNA hybridization are, for example, 6.0× sodium chloride/sodium citrate (SSC) at about 45° C., followed by a wash of 2.0×SSC at 50° C., and they are known to those skilled in the art or can be found in laboratory manuals including but not limited to Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. For example, hybridization using DNA or RNA probes or primers can be performed at 65° C. in 6×SSC, 0.5% SDS, 5×Denhardt's, 100 μg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well known to those of skill in the art. Thus depending on the application envisioned, one will desire to employ varying hybridization conditions to achieve varying degrees of selectivity of probe towards target sequence and the method of choice will depend on the desired results.

The nucleic acid sequences in SEQ ID NOs: 35-62, and any variants thereof, are capable of hybridizing to other nucleic acid sequences under appropriately selected conditions of stringency. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" if they can hybridize to one another with sufficient stability to permit them to remain annealed to one another under conventional "high stringency" conditions. Conventional stringency conditions are described by Sambrook et al. (*Molecular Cloning, A Laboratory Manual, 2nd Ed.*, Cold Spring Harbor Press, Cold Spring Harbor, N.Y., 1989), and by Haymes et al. (*Nucleic Acid Hybridization, A Practical Approach*, IRL Press, Washington, D.C., 1985).

In a preferred embodiment, the nucleic acid sequences SEQ ID NOs: 35-62 or a fragment, region, cis element, or oligomer of these sequences may be used in hybridization assays of other plant tissues to identify closely related or homologous genes and associated regulatory sequences. These include but are not limited to Southern or northern hybridization assays on any substrate including but not limited to an appropriately prepared plant tissue, cellulose, nylon, or combination filter, chip, or glass slide. Such methodologies are well known in the art and are available in a kit or preparation that can be supplied by commercial vendors.

Of course, nucleic acid fragments can also be obtained by other techniques such as by directly synthesizing the fragment by chemical means, as is commonly practiced by using an automated oligonucleotide synthesizer. Fragments can also be obtained by application of nucleic acid reproduction technology, such as the PCR™ (polymerase chain reaction) technology or by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

A fragment of a nucleic acid as used herein is a portion of the nucleic acid that is less than full-length. For example, for the present invention any length of nucleotide sequence that is less than the disclosed nucleotide sequences of SEQ ID NOs: 35-62 is considered to be a fragment. A fragment can also comprise at least a minimum length capable of hybridizing specifically with a native nucleic acid under stringent hybridization conditions as defined above. The length of such a minimal fragment is preferably at least 8 nucleotides, more preferably 15 nucleotides, even more preferably at least 20 nucleotides, and most preferably at least 30 nucleotides of a native nucleic acid sequence.

The nucleic acid sequences of the present invention can also be used as probes and primers. Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described (see Sambrook et al., 1989; Ausubel et al., 1992, and Innis et al., 1990). PCR-primer pairs can be derived from a known sequence, for example, by using computer programs intended for that purpose such as Primer (Version 0.5, © 1991, Whitehead Institute for Biomedical Research, Cambridge, Mass.). Primers and probes based on the native promoter sequences disclosed herein can be used to confirm and, if necessary, to modify the disclosed sequences by conventional methods, e.g., by re-cloning and re-sequencing.

In another embodiment, the nucleotide sequences of the promoters disclosed herein can be modified. Those skilled in the art can create DNA molecules that have variations in the nucleotide sequence. The nucleotide sequences of the present invention as shown in SEQ ID NOs: 35-62 may be modified or altered to enhance their control characteristics. One preferred method of alteration of a nucleic acid sequence is to use PCR to modify selected nucleotides or regions of sequences. These methods are known to those skilled in the art. Sequences can be modified, for example by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In another embodiment, the nucleotide sequences as shown in SEQ ID NOs: 35-62 include any length of said nucleotide sequences that are capable of regulating an operably linked DNA sequence. For example, the sequences as disclosed in SEQ ID NOs: 35-62 may be truncated or portions deleted and still be capable of regulating transcription of an operably linked DNA sequence. In a related embodiment, a cis element of the disclosed sequences may confer a particular specificity such as conferring enhanced expression of operably linked DNA sequences in certain tissues. Consequently, any sequence fragments, portions, or regions of the disclosed sequences of SEQ ID NOs: 35-62 can be used as regulatory sequences including but not limited to cis elements or motifs of the disclosed sequences. For example, one or more base pairs may be deleted from the 5' or 3' end of a promoter sequence to produce a "truncated" promoter. One or more base pairs can also be inserted, deleted, or substituted internally to a promoter sequence. Promoters can be constructed such that promoter fragments or elements are operably linked for example, by placing such a fragment upstream of a minimal promoter. A "minimal promoter" or "basal promoter" refers to a piece of DNA fragment of a promoter that is capable of recruiting and binding the basal transcription machinery. A minimal promoter responds to transcriptional activator sequences. A minimal promoter may be combined with any fragment of a promoter of the present invention to form a chimeric or hybrid promoter so that the activity of the promoter fragment of the present invention may be tested. A "CaMV minimal promoter" is a fragment of the CaMV promoter that is isolated from the cauliflower mosaic virus (CaMV). A minimal CaMV 35S promoter is a good example that may be used in the present invention, which is capable of expressing in most plant tissues. One example of the basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region that are capable of recruiting and binding transcription factors that modulate transcription, e.g., enhance, repress, render transcription hormone-dependent, etc. Substitutions, deletions, insertions or any combination thereof can be combined to produce a final construct.

Native or synthetic nucleic acids according to the present invention can be incorporated into recombinant nucleic acid constructs, typically DNA constructs, capable of introduction into and replication in a host cell. In one preferred embodiment, the nucleotide sequences of the present invention as shown in SEQ ID NOs: 35-62 or fragments, variants or derivatives thereof are incorporated into an expression vector cassette that includes the promoter regions of the present invention operably linked to a genetic component such as a selectable, screenable, or scorable marker gene. The disclosed nucleic acid sequences of the present invention are preferably operably linked to a genetic component such as a nucleic acid that confers a desirable characteristic associated with plant morphology, physiology, growth and development, yield, nutritional enhancement, disease or pest resistance, or environmental or chemical tolerance. These genetic components such as marker genes or agronomic genes of interest can function in the identification of a transformed plant cell or plant, or a produce a product of agronomic utility.

In a preferred embodiment, one genetic component produces a product that serves as a selection device and functions in a regenerable plant tissue to produce a compound that would confer upon the plant tissue resistance to an otherwise toxic compound. Genes of interest for use as a selectable, screenable, or scorable marker would include but are not limited to GUS (coding sequence for beta-glucuronidase), GFP (coding sequence for green fluorescent protein), LUX (coding gene for luciferase), antibiotic resistance marker genes, or herbicide tolerance genes. Examples of transposons and associated antibiotic resistance genes include the transposons Tns (bla), Tn5 (nptII), Tn7 (dhfr), penicillins, kanamycin (and neomycin, G418, bleomycin), methotrexate (and trimethoprim), chloramphenicol and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil (Cell Culture and Somatic Cell Genetics of Plants, Vols. I-III, Laboratory Procedures and Their Applications Academic Press, New York, 1984). Particularly preferred selectable marker genes for use in the present invention would include genes that confer resistance to compounds such as antibiotics like kanamycin and herbicides like glyphosate (Della-Cioppa et al., Bio/Technology 5(6), 1987; U.S. Pat. Nos. 5,463,175 and 5,633,435). Other selection devices can also be implemented and would still fall within the scope of the present invention.

For the practice of the present invention, conventional compositions and methods for preparing and using vectors and host cells are employed, as discussed, inter alia, in Sambrook et al., 1989. In a preferred embodiment, the host cell is a plant cell. A number of vectors suitable for stable transfection of plant cells or for the establishment of transgenic plants have been described in, e.g., Pouwels et al. (Cloning Vectors: A Laboratory Manual, 1985, supp. 1987); Weissbach and Weissbach (Methods for Plant Molecular Biology, Academic Press, 1989); Gelvin et al. (Plant Molecular Biology Manual, Kluwer Academic Publishers, 1990); and Croy (Plant Molecular Biology LabFax, BIOS Scientific Publishers, 1993). Plant expression vectors can include, for example, one or more cloned plant genes under the transcriptional control of 5' and 3' regulatory sequences. They can also include a selectable marker as described to select for host cells containing the expression vector. Such plant expression vectors also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and a polyadenylation signal. Other sequences of bacterial origin are also included to allow the vector to be cloned in a bacterial host. The vector will also typically contain a broad host range prokaryotic origin of replication. In a particularly preferred embodiment, the host cell is a plant cell and the plant expression vector comprises a promoter region as disclosed in SEQ ID NOs: 35-62, an operably linked transcribable sequence, and a transcription termination sequence. Other regulatory sequences envisioned as genetic components in an expression vector include, but is not limited to, non-translated leader sequence that can be coupled with the promoter. Plant expression vectors also can comprise additional sequences including but not limited to restriction enzyme sites that are useful for cloning purposes.

A number of promoters have utility for plant gene expression for any gene of interest including but not limited to selectable markers, scorable markers, genes for pest tolerance, disease tolerance, nutritional enhancements and any other gene that confers a desirable trait or characteristic. Examples of constitutive promoters useful for plant gene expression include, but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988); the octopine synthase promoter (Fromm et al., Plant Cell 1:977, 1989); and the figwort mosaic virus (FMV) promoter as described in U.S. Pat. No. 5,378,619.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wun1, Siebertz et al., Plant Cell 1:961, 1989); or (5) chemicals such as methyl jasmonate, salicylic acid, or safener. It may also be advantageous to employ (6) organ-specific promoters (e.g., Roshal et al., EMBO J. 6:1155, 1987; Schermthaner et al., EMBO J. 7:1249, 1988; Bustos et al., Plant Cell 1:839, 1989). The promoters of the present invention are plant promoters that are capable of transcribing operably linked DNA sequences in male reproductive tissues and can be operably linked to any gene of interest in an expression vector.

Plant expression vectors can include RNA processing signals, e.g., introns, which may be positioned upstream or downstream of a polypeptide-encoding sequence in the transgene. In addition, the expression vectors may include additional regulatory sequences from the 3'-untranslated region of plant genes (Thornburg et al., Proc. Natl. Acad. Sci. USA 84: 744, 1987; An et al., Plant Cell 1: 115, 1989), e.g., a 3' terminator region to increase mRNA stability of the mRNA, such as the PI-II terminator region of potato or the octopine or nopaline synthase 3' terminator regions. Five prime non-translated regions of a mRNA can play an important role in translation initiation and can also be a genetic component in a plant expression vector. For example, non-translated 5' leader sequences derived from heat shock protein genes have been demonstrated to enhance gene expression in plants (see, for example U.S. Pat. No. 5,362,865). These additional upstream and downstream regulatory sequences may be derived from a source that is native or heterologous with respect to the other elements present on the expression vector.

The promoter sequences of the present invention are used to control gene expression in plant cells. The disclosed promoter sequences are genetic components that are part of vectors used in plant transformation. The promoter sequences of the present invention can be used with any suitable plant transformation plasmid or vector containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance, such as a B.t., pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, fertilizer, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9: 207, 1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene that produces a protein or mRNA that expresses a phenotype or morphology change of interest is useful for the practice of the present invention.

In addition to regulatory elements or sequences located upstream (5') or within a DNA sequence, there are downstream (3') sequences that affect gene expression and thus the term regulatory sequence as used herein refers to any nucleotide sequence located upstream, within, or downstream to a DNA sequence that controls, mediates, or affects expression of a gene product in conjunction with the protein synthetic apparatus of the cell.

The promoter sequences of the present invention may be modified, for example for expression in other plant systems. In another approach, novel hybrid promoters can be designed or engineered by a number of methods. Many promoters contain upstream sequences that activate, enhance or define the strength and/or specificity of the promoter (Atchison, Ann. Rev. Cell Biol. 4:127, 1988). T-DNA genes, for example, contain "TATA" boxes defining the site of transcription initiation and other upstream elements located upstream of the transcription initiation site modulate transcription levels (Gelvin, In: Transgenic Plants, Kung and Us, eds, San Diego: Academic Press, pp. 49-87, 1988). Chimeric promoter combined a trimer of the octopine synthase (ocs) activator to the mannopine synthase (mas) activator plus promoter and reported an increase in expression of a reporter gene (Min Ni et al., The Plant Journal 7: 661, 1995). The upstream regulatory sequences of the present invention can be used for the construction of such chimeric or hybrid promoters. Methods for construction of variant promoters of the present invention include but are not limited to combining control elements of different promoters or duplicating portions or regions of a promoter (see for example U.S. Pat. Nos. 5,110,732 and 5,097,025). Those of skill in the art are familiar with the standard resource materials that describe specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Maliga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

The promoter sequences of the present invention may be incorporated into an expression vector using screenable or scorable markers as described and tested in transient analyses that provide an indication of gene expression in stable plant systems. Methods for testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12: 612, 1993, electroporation of leaf protoplasts of wheat (Sethi et al., J. Crop Sci. 52: 152, 1983; electroporation of protoplast prepared from corn tissue (Sheen, The Plant Cell 3: 225, 1991), or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include, but are not limited to, leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences of the present invention include a GUS gene or a GFP gene. The expression vectors containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the 5' regulatory sequences when operatively linked to genes of agronomic interest in stable plants. Ultimately, the 5' regulatory sequences of the present invention are directly incorporated into suitable plant transformation expression vectors comprising the 5' regulatory sequences operatively linked to a transcribable DNA, sequence interest, transformed into plants and the stably transformed plants and progeny thereof analyzed for the desired expression profile conferred by the 5' regulatory sequences.

Those of skill in the art are aware of the vectors suitable for plant transformation. Suitable vectors would include but are not limited to disarmed Ti-plasmids for Agrobacterium-mediated methods. These vectors can contain a resistance marker, 1-2 T-DNA borders, and origins of replication for E. coli and Agrobacterium along with one or more genes of interest and associated regulatory regions. Those of skill in the art are aware that for Agrobacterium-mediated approaches a number of strains and methods are available. Such strains would include but are not limited to Agrobacterium strains C58, LBA4404, EHA101 and EHA105. Particularly preferred strains are *Agrobacterium tumefaciens* strains. Other DNA delivery systems for plant transformation are also known to those of skill in the art and include, but are not limited to, particle bombardment of selected plant tissues.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet which one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation vectors containing the promoter sequences of the present invention may be introduced into plants by any plant transformation method. Several methods are available for introducing DNA sequences into plant cells and are well known in the art. Suitable methods include but are not limited to bacterial infection, binary bacterial artificial chromosome vectors, direct delivery of DNA (e.g. via PEG-mediated transformation, desiccation/inhibition-mediated DNA uptake, electroporation, agitation with silicon carbide fibers), and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. Nos. 5,004,863, 5,159,135 and 5,518,908, WO 97/43430), soybean (U.S. Pat. Nos. 5,569,834 and 5,416,011; McCabe et al., Bio/Technology, 6:923, 1988; Christou et al., Plant Physiol., 87: 671, 1988); Brassica (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes et al., Science, 240: 204, 1988; Gordon-Kamm et al., Plant Cell, 2: 603, 1990; Fromm et al., Bio/Technology, 8: 833, 1990; Koziel et al., Bio/Technology, 11: 194, 1993); oats (*Avena sativa*; Somers et al., Bio/Technology, 10: 1589, 1992); orchardgrass (*Dactylis glomerata*; Horn et al., Plant Cell Rep., 7: 469, 1988); rice (*Oryza sativa*, including indica and japonica varieties, Toriyama et al., Bio/Technology, 6: 10, 1988; Zhang et al., Plant Cell Rep., 7: 379, 1988; Luo and Wu, Plant Mol. Biol. Rep., 6: 165, 1988; Zhang and Wu, Theor. Appl. Genet. 76: 835, 1988; Christou et al., Bio/Technology, 9: 957, 1991); sorghum (*Sorghum bicolor*; Casas et al., Proc. Natl. Acad. Sci. U.S.A., 90: 11212, 1993); sugar cane (Saccharum spp.; Bower and Birch, Plant J., 2: 409, 1992); tall fescue (*Festuca*

*arundinacea*; Wang et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks et al., Plant Physiol., 102: 1077, 1993; Becker et al., Plant, J. 5: 299, 1994), and alfalfa (Masoud et al., Transgen. Res. 5: 313, 1996). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including but not limited to cDNA library preparation, genomic library preparation, sequencing, sequence analyses, PCR technologies, vector construction, transient assays, and plant transformation methods are well known to those of skill in the art and are carried out using standard techniques or modifications thereof.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Plant Material, DNA Isolation and Library Construction

The target maize cDNA library was library 3279 made from maize anthers that were collected prior to the microspore mother cells undergoing meiosis. The background cDNA libraries included cDNA libraries prepared from leaf, root, embryo, callus, shoot, seedling, endosperm, culm ear and silk Plant Growth Conditions Seeds are planted at a depth of about 3 cm in soil into 2"-3" pots containing Metro 200 growing medium and transplanted into larger 10" pots containing the same soil after 2-3 weeks. Plants are fertilized as needed. A total of about 900 mg Fe is added to each pot. Corn plants are grown in the greenhouse in 15 hr day/9 hr night cycles. The daytime temperature is 26.7° C. and the night temperature is 21.1° C. 1000 W sodium vapor lamps are provided for lighting.

Tissue Isolation

The corn early anther cDNA library (LIB3279) is generated from maize (H99 USDA Maize Genetics Stock Center, Urbana, Ill. U.S.A.) from about 1-2 mm anther tissue harvested from plants 37 days after germination. At this stage, the anthers are green, 1-2 mm long and enclosed in staminate spikelets. The developing anthers are dissected away from the plants and immediately frozen in liquid nitrogen. The harvested tissue is stored at −80° C. until RNA preparation.

The RNA is purified using Trizol reagent available from Life Technologies (Gaithersburg, Md.) essentially as recommended by the manufacturer. Poly A+ RNA (mRNA) is purified using magnetic oligo dT beads essentially as recommended by the manufacturer (Dynabeads, Dynal Corporation, Lake Success, N.Y.). Two modifications to the Trizol protocol include centrifuging the ground tissue samples at 12,000×g for 10 minutes at 4° C. after the addition of Trizol to remove insoluble material, and precipitating the RNA with 0.25 mL isopropanol and 0.25 mL 0.8M NaCl per 1.0 mL Trizol used. All the samples are precipitated with 0.1 volume of 3M NaOAc and 3.0 volumes of ethanol. RNAs are resuspended in distilled water at a concentration of 2 µg/µL. The RNAs are treated for 10 minutes at room temperature with RNase free DNase (BMB, Indianapolis, Ind.) and samples are extracted with phenol/chloroform and isopropanol precipitated as described, and resuspended in distilled water at a concentration of 1 µg/µL.

Construction of cDNA libraries is well known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md.) is used, following the conditions suggested by the manufacturer.

The cDNA libraries are plated on LB agar containing the appropriate antibiotics for selection and incubated at 37° C. for a sufficient time to allow the growth of individual colonies. Single colonies are individually placed in each well of a 96-well microtiter plate containing LB liquid including selective antibiotics. The plates are incubated overnight at approximately 37° C. with gentle shaking to promote growth of the cultures. The plasmid DNA is isolated from each clone using Qiaprep Plasmid Isolation kits, using the conditions recommended by the manufacturer (Qiagen Inc., Santa Clara, Calif.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif.).

Example 2

Promoter Lead Identification and Isolation Methodologies

The database of EST sequences derived from the cDNA libraries prepared from various corn tissues is used to identify the genes with the correct expression profile from which promoter candidates can be isolated for expression of operably linked DNA sequences in male reproductive tissues. The sequences are also used as query sequences against GenBank databases that contain previously identified and annotated sequences and searched for regions of homology using BLAST programs. The selection of expressed sequence tags (ESTs) for subsequent promoter isolation is reflective of the presence of one or more sequences among the representative ESTs from a random sampling of an individual cDNA library or collection of cDNA libraries. To identify regulatory sequences that regulate the expression of transcripts in the target tissues of interest from EST sequences in the database, a subsetting function is done, requesting ESTs found in target libraries such as LIB3279 and EST clones in all other libraries are subtracted. The background or non-target libraries are listed in Table 1. The cDNA clones identified from the subsetting are candidates for tissue-enhanced/specific genes and are further pursued.

TABLE 1

The background or non-target libraries

| Libraries | Usable | Descriptions |
|---|---|---|
| SATMON013 | 8202 | corn (Zea mays), meristem |
| SATMON020 | 3867 | corn (Zea mays), initiated callus, Hi II Type II |
| SATMON022 | 4440 | corn (Zea mays), immature ear |
| SATMON023 | 4554 | corn (Zea mays), ear (growing silks) |
| SATMON025 | 7460 | corn (Zea mays), callus, regenerating, HI II type II |
| SATMON004 | 3472 | corn (Zea mays), leaf |
| SATMON009 | 3698 | corn (Zea mays), leaf, V8 stage GH |
| SATMON011 | 13409 | corn (Zea mays), leaf, undeveloped |
| SATMON016 | 8984 | corn (Zea mays), sheath |
| SATMON026 | 2901 | corn (Zea mays), leaf, juvenile adult shift |
| SATMON027 | 3290 | corn (Zea mays), leaf, water-stressed 6 days |
| SATMON031 | 4377 | corn (Zea mays), leaf, V4 stage |
| SATMONN01 | 7193 | corn (Zea mays), leaf, NORM |
| SATMON003 | 12533 | corn (Zea mays), root |
| SATMON007 | 9910 | corn (Zea mays), primary root |
| SATMON010 | 11231 | corn (Zea mays), root, V8 stage GH |
| SATMON028 | 3271 | corn (Zea mays), root, water-stressed 6 days |
| SATMON030 | 4944 | corn (Zea mays), root, V4 stage |
| SATMONN05 | 4401 | corn (Zea mays), root, NORM |
| SATMON014 | 4465 | corn (Zea mays), endosperm, 14-DAP |
| SATMON017 | 7472 | corn (Zea mays), embryo, 21-DAP |
| SATMON033 | 3634 | corn (Zea mays), embryo, 13 DAP |
| SATMON036 | 6250 | corn (Zea mays), endosperm, 22-DAP |
| SATMONN04 | 3765 | corn (Zea mays), embryo, 21-DAP, NORM |
| SATMONN06 | 2673 | corn (Zea mays), embryo, 21-DAP, NORM |
| SATMON008 | 3892 | corn (Zea mays), primary shoot |
| SATMON012 | 4819 | corn (Zea mays), seedling, 2 days post-germination |
| SATMON019 | 3833 | corn (Zea mays), culm |
| SATMON029 | 3329 | corn (Zea mays), seedling, etiolated 4 days |
| SATMON034 | 3713 | corn (Zea mays), seedling, cold stressed |

Methodologies Used for Identifying Each Promoter Lead for Isolation

Electronic Subsetting

Electronic subsettings were performed using the corn Maizeseq database to identify clones represented in library 3279 and not represented in library that was not derived from male tissue. These libraries were listed in Table 1. The resulting cDNA's were candidates for tissue-specific/enhanced genes and were further pursued. Electronic translation of the EST sequence and similarities to known proteins were used to identify a potential translation initiation codon (ATG). Twelve EST clones met this criteria. Promoter fragments were isolated using the Genome Walker protocol. Upon isolation, the genomic fragments were cloned into the pGEM-T-easy cloning vector kit (Promega, Madison, Wis., Cat. No. A1360), were sequenced at the both the 5' end and 3' end, and were placed into a reporter gene construct to assay promoter activity in vivo and/or in planta.

Subtracted Libraries

Subtracted libraries were made by first synthesizing cDNA using the SMART kit (Clonetech, Palo Alto, Calif., Cat. No. K1052-1) and then subtracting non-anther specific cDNAs from the tester population using the PCR Select kit (Clonetech, Palo Alto, Calif., Cat. No. K1804-1). With both kits, the manufacturer's protocol was followed. The tissues used for the RNA isolation was from OSLO wheat and the RNA was isolated using the Trizol reagent (Life Technologies) following their protocol. The tester RNA was from anther isolated from Feekes stage 10+ plants. The driver RNA was from root (stage 6), leaf (stage 6), and etiolated seedling (3 day) RNA.

Transcriptional Profiling

Approximately 6,000 randomly chosen clones from library 3279 (corn early anther cDNA library) were picked into 50 μL of LB amp plus glycerol, grown overnight at 37 C, then stored frozen at −80 C. The clones were thawed, rearrayed into 50 μL of LB amp in a 384 well plate, keeping 1 row blank (to be used for controls), and grown overnight at 37 C. The resulting cultures were pelleted for 15 minutes and the media removed. The pellet was resuspended in 20 μL Qiagen buffer P1 (QiagenPlasmid Maxi Kit, Cat. No. 12262) by vortexing. The cells were lysed by adding 20 μL of Qiagen buffer P2 (Qiagen, Plasmid Maxi Kit, Cat. No. 12262) and vortexing

TABLE 2

Methodologies used for identifying each promoter lead for isolation

| Clone ID | SEQ ID NO | Organism | Annotation | Strategies for identifying genes |
|---|---|---|---|---|
| 1674-10 | 56 | wheat | actin depolymerizing factor | subtracted library |
| 1674-19 | 57 | wheat | novel | subtracted library |
| 16883-3 | 49 | corn | lipid transfer protein from Helianthus annuus | transcriptional profiling |
| 3253-1 | 50 | corn | none | transcriptional profiling |
| 3279-052-A12 | 52 | corn | none | transcriptional profiling |
| 41140-1 | 43 | corn | mtn3 gene | electronic subsetting |
| 41291-1 | 36 | corn | UDP-glucose-4-epimerase | electronic subsetting |
| 41292-1 | 44 | corn | wheat rubisco subunit binding protein alpha subunit precursor | electronic subsetting transcriptional profiling |
| 41786-1 | 47 | corn | Arabidopsis F17L21.12 | electronic subsetting |
| 42672-1 | 37 | corn | putative dimethyladenosine transferase | electronic subsetting |
| 73224d06b2 | 54 | corn | alpha tubulin 1 {Eleusine indica} | transcriptional profiling |
| 985-1 | 40 | corn | none | electronic subsetting | slowly. Lysates were spotted on Hybond N+ membranes (Amhersham) in a 3×3 grid using the Genome Systems Flexys Robot fitted with a 384 well pin. Each spot was imprinted 3 times per filter. The controls consisted of the tetracycline gene that was amplified from the plasmid pBR322 (Life Technologies) and a vector control (pET, Stratagene, La Jolla, Calif.). After spotting, membranes were allowed to dry before treating for 3-5 minutes in 0.4N NaOH. It was followed by 3-5 minutes in 1M Tris 7.4 and then 2 minutes in 2×SSC. The filters were allowed to dry on between Whatman 3 mm paper.

Labeled cDNA was used to probe the filters. The cDNA was derived from poly A+ RNA isolated per the manufacturer's protocol using the Qiagen Oligotex mRNA Midi Kit (Qiagen, Cat. No. 70042) from total RNA isolated using the Trizol reagent (Life Technologies) described above. RNA was isolated from the following corn tissues (genotype LH172): premicrospore anthers, anthers with microspore mother cells or tetrads, anthers with developing pollen at the 1N or 2N stage, anthers with near mature pollen at the 3N stage, leaf, root, and prepollinated kernals from 3.5 cm ears. A half microgram of polyA+ RNA plus 25 ng of tetracycline RNA were mixed, ethanol precipitated, and resuspended in 9 µL of water plus 2 µL of Oligo dT (Life Technologies)(1 µg/µL). The solution was heated to 70 C for 2 minutes and placed on ice. While on ice, 5 µL of 5× superscript buffer (Life Technologies), 2.5 µL 0.1M DTT, 0.8 µL dNTP mix (10 mM dATP, dGTP, dTTP, 0.1 mM dCTP), 5 µL 33P-alpha dCTP, and 1 µL superscript II reverse transcriptase (Life Technologies) were added. The mixtures were incubated at 42 C. for 4 hours then purified on a chromaspin 30 columns (Clonetech) following manufacturer's instructions. The probe was denatured by adding 1/10 volume of 0.5N NaOH, 1/10 volume EDTA, equal volume water and incubating 65 C for 10 minutes. Probes were added to the above filters which were pre-hybridizing in 20 mL of the following buffer: 7% SDS, 0.25 M NaPO4, pH. 7.2, 1 mM EDTA, 0.5% dry milk, 100 µg/mL salmon sperm DNA. The filters with probe added, were incubated at 68 C overnight. The filters were then washed once in 2×SSC, 1% SDS at 68 C for 15 minutes and twice in 0.2×SSC 1% SDS at 68 C for 30 minutes each. The filters were allowed to dry and exposed to a phospho-imager screen (Molecular Dynamics, Sunnyvale, Calif.) for 20 hours before detection in a Molecular Dynamics 860 Phosphoimager.

Example 3

Genomic Library Construction, PCR Amplification and Promoter Isolation

A number of methods are known to those skilled in the art for genomic library preparation. For genomic libraries of the present invention, corn DNA (Maize hybrid Fr27×FrMo17) is isolated by a CsCl purification protocol according to Ausubel et al. (1992) or by a CTAB purification method (Rogers and Bendich, Plant Mol. Biol., 5:69, 1988). Reagents are available commercially (see, for example Sigma Chemical Co., St. Louis, Mo.). The libraries are prepared according to manufacturer instructions (GENOME WALKER, a trademark of CLONTECH Laboratories, Inc, Palo Alto, Calif.). In separate reactions, genomic DNA is subjected to restriction enzyme digestion overnight at 37° C. with the following blunt-end endonucleases: EcoRV, ScaI, DraI, PvuII, or StuI (CLONTECH, Inc., Palo Alto, Calif.). The reaction mixtures are extracted with phenol:chloroform, ethanol precipitated, and resuspended in Tris-EDTA buffer. The purified blunt-ended genomic DNA fragments are then ligated to the GenomeWalker™ adaptors and ligation of the resulting DNA fragments to adaptors are done according to manufacturer protocol. The GenomeWalker™ sublibraries are aliquoted and stored at −20° C.

Genomic DNA ligated to the GenomeWalker™ adaptor (above) is subjected to a primary round of PCR amplification with gene-specific primer 1 (GSP1) and a primer that anneals to the Adaptor sequence, adaptor primer 1 (AP1) (5'GTAATACGACTCACTATAGGGC3', SEQ ID NO: 1). A diluted (1:50) aliquot of the primary PCR reaction is used as the input DNA for a nested round of PCR amplification with gene-specific primer 2 (GSP2) and adaptor primer 2 (AP2) (5'ACTATAGGGCACGCGTGGT3', SEQ ID NO: 2), or adaptor primer 3 (AP3) (5'AGGGCAAGCTTGGTCGACG-GCCCGGGCTGGT3', SEQ ID NO: 3). The annealing temperatures of the GenomeWalker™ primary primer (AP1) and nested primer (AP2) are 59° C. and 71° C., respectively. Generally, gene specific primers are designed to have the following characteristics: 26-30 nucleotides in length, GC content of 40-60% with resulting temperatures for most of the gene specific primers in the high 60° C. range or about 70° C. The Taq polymerase used is Amplitaq Gold™ or Expand HiFidelity (Boehringer Mannheim) available through Perkin-Elmer Biosystems (Branchbury, N.J.). A number of temperature cycling instruments and reagent kits are commercially available for performing PCR experiments and include those available from PE Biosystems (Foster City, Calif.), Stratagene (La Jolla, Calif.), and MJ Research Inc. (Watertown, Mass.). Following the primary PCR reaction, an aliquot is taken (10-15 µL) for agarose gel analysis. Isolation of each unknown sequence required amplification from 5 sub-genomic libraries and a negative control (without DNA).

The PCR components and conditions generally used are outlined below:

Primary PCR

| Component | Amount/Volume required |
|---|---|
| Sub-library aliquot | 1 µL |
| Gene-specific primer 1 | 1 µL (100 pmol) |
| Genome Walker ™ Adaptor primer 1 (AP1) | 1 µL |
| dNTP mix (10 mM of each dNTP) | 1 µL |
| DMSO | 2.5 µL (or 2-5% final concentration) |
| 10X PCR buffer (containing MgCl₂) | 5 µL (final concentration of 1X) |
| Amplitaq Gold ™ or Expand HiFidelity | 0.5 µL |
| Distilled Water | For final reaction volume of 50 µL |

Reaction Conditions for Primary PCR:

A. 1 minutes at 95° C.;

B. 94° C. for 2 seconds, 70° C. for 3 minutes; repeat 94° C./70° C. cycling for total of 7 times;

C. 94° C. for 2 seconds, 65° C. for 3 minutes; repeat 94° C./65° C. cycling for total of 36 times;

D. 65° C. for 4 minutes as a final extension; and

E. 10° C. for an extended incubation.

Nested PCR (Secondary PCR Reaction)

| Component | Amount/Volume Required |
| --- | --- |
| 1:50 dilution of the primary PCR reaction | 1 µL |
| Gene-specific primer 2 | 1 µL (100 pmol) |
| Genome Walker ™ Adaptor primer 2 or 3 (AP2 or AP3)) | 1 µL |
| dNTP mix (10 mM of each dNTP) | 1 µL |
| DMSO | 2.5 µL |
| 10X PCR buffer (containing $MgCl_2$) | 5 µL (final concentration of 1X) |
| Amplitaq Gold ™ | 0.5 µL |
| Distilled water | to final reaction volume of 50 µL |

Reaction Conditions for Nested PCR:

A. 1 minutes at 95° C.;

B. 94° C. for 2 seconds, 70° C. for 3 minutes; repeat 94° C./70° C. cycling for total of 5 times;

C. 94° C. for 2 seconds, 65° C. for 3 minutes; repeat 94° C./65° C. cycling for total of 24 times;

D. 65° C. for 4 minutes as a final extension; and

E. 10° C. for an extended incubation.

3a. 41291-1 Clone ID Analysis and Promoter Isolation

For the isolation of the clone ID 41291-1 promoter, gene specific primer SEQ ID NO: 4 (5'CTCATGCCTATGGA-CATAGTCTAATCGC3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 µL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 µL of the primary reaction was used with gene specific primer SEQ ID NO: 5 (5'GGATCCAGATCTTGGTTAGAGGACAAC-CGTTGGAAGGAG3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and a band of approximately 720 bp, called 41291-720, and a band approximately 1500 bp, called 41291-1500, were cut out, purified using Supelco Genelute columns (Sigma, St. Louis, Mo., Cat No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 1500 bp promoter for clone ID 41291-1 is SEQ ID NO: 35. The 720 bp promoter fragment is SEQ ID NO: 36.

3b. 42672-1 Clone ID Analysis and Promoter Isolation

For the isolation of the clone ID 42672-1 promoter, gene specific primer SEQ ID NO: 6 (5'GCCCAGAGAGCG-GAGACGGCTCGCTTC3') was used in combination with adapter primer SEQ ID NO: 1 in a standard Genome Walker PCR reaction (see SOP) with the following conditions: Expand Hi Fidelity DNA Polymerase (BMB Indianapolis, Ind. Cat. No. 1759078) was used in conjunction with the supplied buffer No. 2, 2 µL of a 1:2 dilution of Genome Walker libraries made according to the manufacturer's protocol (Clontech, Palo Alto, Calif., Cat No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 µL of the primary reaction was used with gene specific primer SEQ ID NO: 7 (5'GGATCCAGATCTCTCGACTGCAGAGCT-GCTTGGTTGGCC3') and adapter primer SEQ ID NO: 3 in a standard Genome Walker PCR reaction (see SOP) using Expand Hi Fidelity DNA Polymerase (BMB Indianapolis, Ind. Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and a band of approximately 820 bp, called 42672-820, and a band approximately 2700 bp, called 42672-2700, were cut out, purified using Supelco Genelute columns (Sigma, St. Louis, Mo., Cat No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 2700 bp promoter for clone ID 42672-1 is SEQ ID NO: 37. The 820 bp promoter fragment is SEQ ID NO: 38.

3c. 985-1 Clone ID Analysis and Promoter Isolation

For the isolation of the clone ID 985-1 promoter, gene specific primer SEQ ID NO: 8 (5'GTAGTGCCCTGTC-CCGACCCTCAAGCC3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 µL of a 1:2 dilution of Genome Walker libraries made according to the manufacturer's protocol (Clontech, Palo Alto, Calif., Cat No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 µL of the primary reaction was used with gene specific primer SEQ ID NO: 9 (5'GGATCCAGATCTTCGCCTGCTAGGGC-CTAGGGCTCGCTC3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and 4 bands of approximately 500 bp, called 985-500, 720 bp, called 985-720, 1020 bp, called 985-1020, 2000 bp, called 985-2000, were cut out, purified using Supelco Genelute columns (Sigma, St. Louis, Mo., Cat No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 2000 bp promoter for clone ID 985-1 is SEQ ID NO: 39. The 500 bp promoter fragment is SEQ ID NO: 40, the 720 bp promoter fragment is SEQ ID NO: 41, and the 1020 bp promoter fragment is SEQ ID NO: 42.

3d. 41140-1 Clone ID Analysis and Promoter Isolation

For the isolation of the clone ID 41140-1 promoter, gene specific primer SEQ ID NO: 10 (5'TCGCCTCCAGGAG-GACGACTGCAATGC3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 µL of a 1:2 dilution of Genome Walker libraries made according to the manufacturer's protocol (Clontech, Palo Alto, Calif. Cat No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 µL of the primary reaction was used with gene specific primer SEQ ID NO: 11 (5'GGATCCAGATCTCGCTTTTCTCTTTCAG-CAAGATGGCTGGCC3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and a band of approximately 420 bp, called 41140-420, and a band approximately 520 bp, called 41140-520, were cut out, purified using Supelco Genelute columns (Sigma, St. Louis, Mo., Cat No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 520 bp promoter for clone ID 41140-1 is SEQ ID NO: 43.

3e. 41292-1 Clone ID Analysis and Promoter Isolation

For the isolation of the clone ID 41292-1 promoter, gene specific primer SEQ ID NO: 12 (5'ACAATCACCAGGGC-CAAGGTGGTGGAG3') was used in combination with adapter primer SEQ ID NO: 3 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 µL of a 1:2 dilution of Genome Walker libraries made according to the manufacturer's protocol (Clontech, Palo Alto, Calif., Cat No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 µL of the primary reaction was used with gene specific primer SEQ ID NO: 13 (5'GGATCCAGATCTCCAATAGCTCGATGCT-CAGGCGCTGAC3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and a band of approximately 680 bp, called 41292-680, was cut out, purified using Supelco Genelute columns (Sigma, St. Louis, Mo., Cat No. 5-6500). Three microliters of the purified band was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 680 bp promoter for clone ID 41929-1 is SEQ ID NO: 44.

3f. 41786-1 Clone ID Analysis and Promoter Isolation

For the isolation of the clone ID 41786-1 promoter, gene specific primer SEQ ID NO: 14 (5'CCGACTACGT-TGCGGGCTGCGTCCAGG3') was used in combination with adapter primer SEQ ID NO: 1 in a standard Genome Walker PCR reaction (see SOP) with the following conditions: Expand Hi Fidelity DNA Polymerase (BMB Indianapolis, Ind. Cat. No. 1759078) was used in conjunction with the supplied buffer No. 2, 2 µL of a 1:2 dilution of Genome Walker libraries made according to the manufacturer's protocol (Clontech, Palo Alto, Calif., Cat No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 minutes, and 33 cycles 94 C 4 seconds, 68 C 3 minutes. For the nested, secondary PCR reaction, 1 µL of the primary reaction was used with gene specific primer SEQ ID NO: 15 (5'GGATCCAGATCTTCGCCGGGGTG-GCGTCGGCGGCTACGC3') and adapter primer SEQ ID NO: 3 in a standard Genome Walker PCR reaction (see SOP) using Expand Hi Fidelity DNA Polymerase (BMB Indianapolis, Ind. Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and 4 bands of approximately 1400 bp, called 41786-1400, 800 bp, called 41786-800, 1800 bp, called 41786-1800, and 1000 bp, called 41786-1000, were cut out, purified using Supelco Genelute columns (Sigma, St. Louis, Mo., Cat No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 1800 bp promoter for clone ID 41786-1 is SEQ ID NO: 40. The 1400 bp promoter fragment is SEQ ID NO: 46. The 1000 bp promoter fragment is SEQ ID NO: 47.

3g. 16883-3 Clone ID Analysis and Promoter Isolation

For the isolation of the clone ID 16883-3 promoter, gene specific primer SEQ ID NO: 16 (5'CCGCCGGAGCT-GATCTCACAGGAGACGG3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 µL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 minutes, and 34 cycles 94 C 4 seconds, 68 C 3 minutes. For the nested, secondary PCR reaction, 1 µL of the primary reaction was used with gene specific primer SEQ ID NO: 17 (5'GGATCCAGATCTGCAAGCGGGGCG-GAGAGGAACGAGGATC3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliters of the secondary PCR reaction was analyzed by agarose gel electrophoresis and 2 bands of approximately 1500 bp, called 16883-1500, and 400 bp, called 16883-400, were cut out, purified using Supelco Genelute columns (Sigma, St. Louis, Mo. Cat. No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 1500 bp promoter for clone ID 16883-3 is SEQ ID NO: 48. The 400 bp promoter fragment is SEQ ID NO: 49.

3h. 3253-1 Clone ID Analysis and Promoter Isolation

For the isolation of the clone ID 3253-1 promoter, gene specific primer SEQ ID NO: 18 (5'TGCCTGGTGGTCA-GAATGGTGGCCTAGG3') was used in combination with adapter primer SEQ ID NO: 1 in a standard Genome Walker PCR reaction (see SOP) with the following conditions: Expand Hi Fidelity DNA Polymerase (BMB Indianapolis, Ind. Cat. No. 1759078) was used in conjunction with the supplied buffer No. 2, 2 µL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 µL of the primary reaction was used with gene specific primer SEQ ID NO: 19 (5'GGATCCAGATCTGTTGGCGGCTG-GATCTGGCCTCTGGCTG3') and adapter primer SEQ ID NO: 3 in a standard Genome Walker PCR reaction (see SOP) using Expand Hi Fidelity DNA Polymerase (BMB Indianapolis, Ind. Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliters of the secondary PCR reaction was analyzed by agarose gel electrophoresis and 2 bands of approximately 1400 bp, called 3253-1400, and 1100 bp, called 3253-1100, were cut out, purified using Supelco Genelute columns (Sigma, St. Louis, Mo. cat No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 1400 bp promoter for clone ID 3253-1 is SEQ ID NO: 50. The 1100 bp promoter fragment is SEQ ID NO: 51.

3i. 3279-052-A12 Clone ID Analysis and Promoter Isolation

For the isolation of the clone ID 3279-052-A12 promoter, gene specific primer SEQ ID NO: 20 (5'TGAAGAGGCGCT-TGACGATGTGCCGGTC3') was used in combination with adapter primer SEQ ID NO: 1 in a standard Genome Walker PCR reaction (see SOP) with the following conditions: Expand Hi Fidelity DNA Polymerase (BMB Indianapolis, Ind. Cat. No. 1759078) was used in conjunction with the supplied buffer No. 2, 2 µL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 µL of the primary reaction was used with gene specific primer SEQ ID NO: 21 (5'AAATGTTGAGGCTGCTTTGCATGCGGTC3') and adapter primer SEQ ID NO: 3 in a standard Genome Walker PCR reaction (see SOP) using Expand Hi Fidelity DNA, Polymerase (BMB Indianapolis, Ind. Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliters of the secondary PCR reaction was analyzed by agarose gel electrophoresis and 2 bands of approximately 2000 bp, called 3279-052-A12-2000, and 3000 bp, 3279-052-A12-3000, were cut out, purified using Supelco Genelute columns (Sigma, St. Louis, Mo., Cat No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center.

Sequence analysis tools indicated a potential translational start site and TATA box sequence. To obtain a promoter fragment upstream of the predicted translational start codon, 1 µL of the isolated DNA is amplified under standard GenomeWalker™ PCR conditions using Expand Hi Fidelity DNA Polymerase (BMB, Indianapolis, Ind.) with the supplied buffer No. 2 in combination with primers SEQ ID NO: 22 (5'GGATCCAGATCTCGCTTGTTTCAGCT-GAGTGCAGAGC3') and AP3-H3. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C. The 3000 bp promoter of clone ID, 3279-052-A12 is SEQ ID NO: 52. The 2000 bp promoter fragment is SEQ ID NO: 53.

3j. 73224d06b2 Clone ID Analysis and Promoter Isolation

For the isolation of the clone ID 73224d06b2 promoter, gene specific primer SEQ ID NO: 23 (5'GTCGTCG-TACGGGTGGAGCGGCGGCCGG3') was used in combination with adapter primer SEQ ID NO: 1 in a standard Genome Walker PCR reaction (see SOP) with the following conditions: Expand Hi Fidelity DNA Polymerase (BMB Indianapolis, Ind. Cat. No. 1759078) was used in conjunction with the supplied buffer No. 2, 2 μL of a 1:2 dilution of a Genome Walker libraries made according to the manufacturer's protocol (Clontech, Palo Alto, Calif. cat No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 μL of the primary reaction was used with gene specific primer SEQ ID NO: 24 (5'GGATCCAGATCTGCCGCGGAGGTAGGC-GAGTACGAAGACG3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliters of the secondary PCR reaction was analyzed by agarose gel electrophoresis and 2 bands of approximately 2000 bp, called 73224d06b2-2000, and 3000 bp, called 73224d06b2-3000, were cut out, purified using Supelco Genelute columns (Sigma, St. Louis, Mo., Cat. No. 5-6500). Three microliters of each of the purified bands was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The 3000 promoter for clone ID 73224d06b2 is SEQ ID NO: 54. The 2000 bp promoter fragment is SEQ ID NO: 55.

3k. 1674-10 Clone ID Analysis and Promoter Isolation

To determine the distribution of the clone ID 1674-10 transcripts in wheat, RT-PCR is performed using primers SEQ ID NO: 25 (5'GTGCTTCATTAGTCAGC3') and SEQ ID NO: 26 (5'CAAGAACAAGGAGCAAG3') following the RT-PCR protocol using cDNA derived from glume/lemma/palea, gynoecium, leaf, microspores, mature anther/pollen, and root. Taq DNA polymerase from BMB (Indianapolis, Ind., Cat. No. 1435094) was used in combination with the supplied reaction buffer. Cycling parameters, using an MJR DNA engine programmed, are as follows: 95 C. for 1 minute, then 35 cycles of 95 C 15 seconds, 55 C. for 30 seconds, 72 C. for 2 minutes. Bands were detected only with mature anther/pollen and microspore cDNA samples.

For the isolation of the clone ID 1674-10 promoter, gene specific SEQ ID NO: 27 (5'GCCGTAACTGGTCTCAC-CGAGCCTCTC3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 μL of a 1:2 dilution of Genome Walker libraries made according to the manufacturer's protocol (Clontech, Palo Alto, Calif., Cat No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 ul of the primary reaction was used with gene specific SEQ ID NO: 28 (5'GAAGCT-TCGTCTCGCCTTCAGGTCCGA3') and adapter primer SEQ ID NO: 2 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliters of the secondary PCR reaction was analyzed by agarose gel electrophoresis and 1 band of approximately 900 bp, called 1674-10-1 was cut out, purified using Supelco Genelute columns (Sigma, St. Louis, Mo. cat No. 5-6500). Three microliters of the purified band was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center.

Sequence analysis tools indicated a potential translational start. To obtain a promoter fragment upstream of the predicted translational start codon, 1 μL of the isolated DNA is amplified under standard GenomeWalker™ PCR conditions using Expand Hi Fidelity DNA Polymerase (BMB, Indianapolis, Ind.) with the supplied buffer No. 2 in combination with primers SEQ ID NO: 29 (5'TTTTGTAGATCTTCAAAGC-CCCCTACACAACGTG 3') and SEQ ID NO: 3. The reactions are carried out under the following cycling conditions: 94° C. 1 minute, 20 cycles of 94° C. 5 seconds, 50° C. 15 seconds, 72° C. 2 minutes. The 900 bp promoter of clone ID, 1674-10 is SEQ ID NO: 56.

3l. 1674-19 Clone ID Analysis and Promoter Isolation

To determine the distribution of the clone ID 1674-19 transcripts in wheat, RT-PCR was performed using primers SEQ ID NO: 30 (5'GCTTGTAATGCTTGATG3') and SEQ ID NO: 31 (5'GACCGGACTGTTGCCTC3') following the RT-PCR protocol using cDNA derived from glume/lemma/palea, gynoecium, leaf, microspores, mature anther/pollen, and root. Taq DNA polymerase from BMB (Indianapolis, Ind., Cat. No. 1435094) was used in combination with the supplied reaction buffer. Cycling parameters, using an MJR DNA engine programmed, are as follows: 95 C for 1 minute, then 35 cycles of 95 C 15 seconds, 55 C for 30 seconds, 72 C for 2 minutes. Bands were detected only with mature anther/pollen cDNA samples.

For the isolation of the clone ID 1674-19 promoter, gene specific SEQ ID NO: 32 (5'CGGGCGTCGCACGAG-GAGAGGAGAAGG3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 μL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 34 cycles 94 C 4 seconds, 68 C 3 minutes. For the nested, secondary PCR reaction, 1 μL of the primary reaction was used with gene specific SEQ ID NO: 33 (5'CGGGCGTCGCACGAGGAGAGGAGAAGG3') and adapter primer SEQ ID NO: 2 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 66 C 3 minutes.

Twenty five microliters of the secondary PCR reaction was analyzed by agarose gel electrophoresis and a band of approximately 1000 bp, called 1674-19-1, was cut out, purified using Supelco Genelute columns (Sigma, St. Louis, Mo., Cat. No. 5-6500). Three microliters of the purified band was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center.

Sequence analysis tools indicated a potential translational start. To obtain a promoter fragment upstream of the predicted translational start codon, 1 µL of the isolated DNA is amplified under standard GenomeWalker™ PCR conditions using Expand Hi Fidelity DNA Polymerase (BMB, Indianapolis, Ind.) with the supplied buffer No. 2 in combination with primers SEQ ID NO: 34 (5'GCGTGCAGATCTGGAGGAG-GCTAGCTACACTT3') and SEQ ID NO: 3. The reactions are carried out under the following cycling conditions: 94° C. 1 minute, 20 cycles of 94° C. 5 seconds, 50° C. 15 seconds, 72° C. 2 minutes. The 1000 bp promoter of clone ID, 1674-19 is SEQ ID NO: 57.

3m. 17603-1 Clone ID Analysis and Promoter Isolation

For the isolation of the clone ID 17603-1 promoter, gene specific primer SEQ ID NO: 63 (5'TGTGCGCGGCGT-TGGGCGCCAGCCCAG3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 µL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 µL of the primary reaction was used with gene specific primer SEQ ID NO: 64 (5'GGATCCAGATCTGCCGGTGGTGGTGGTA-GAGGGAACAGG3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and a band of approximately 1500 bp, called 17603-1-1500, was cut out and purified using Supelco Genelute columns (Sigma, St. Louis, Mo., Cat No. 5-6500). Three microliters of the purified band was ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The ~1500 bp promoter for clone ID 17603-1 is SEQ ID NO: 58.

3n. 41551-1 Clone ID Analysis and Promoter Isolation

For the isolation of the clone ID 41551-1 promoter, gene specific primer SEQ ID NO: 65 (5'TCGGAGAGGCGGAG-GCCGCCGTGTCTG3') was used in combination with adapter primer SEQ ID NO: 1 in a standard Genome Walker PCR reaction (see SOP) with the following conditions: Expand Hi Fidelity DNA Polymerase (BMB Indianapolis, Ind., Cat. No. 1759078) was used in conjunction with the supplied buffer No. 2, 2 µL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 µL of the primary reaction was used with gene specific primer SEQ ID NO: 66 (5'GGATCCAGATCTGGTAGGTCCAGGAGTC-CAAAGCGTTGG3') and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and bands of approximately 1800 bp, called 41551-1-1800, and approximately 810 bp, called 41551-1-810, were cut out and purified using Supelco Genelute columns (Sigma, St. Louis, Mo., Cat No. 5-6500). Three microliters of the purified bands were ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The ~1800 bp promoter for clone ID 41551-1 is SEQ ID NO: 59. The ~810 bp promoter is SEQ ID NO: 60.

3o. 43069-1 Clone ID Analysis and Promoter Isolation

For the isolation of the clone ID 43069-1 promoter, gene specific primer SEQ ID NO: 67 was used in combination with adapter primer SEQ ID NO: 1 in a standard Genome Walker PCR reaction (see SOP) with the following conditions: Expand Hi Fidelity DNA Polymerase (BMB Indianapolis, Ind., Cat: No. 1759078) was used in conjunction with the supplied buffer No. 2, 2 µL of a 1:2 dilution of Genome Walker libraries made according to the manufacturer's protocol (Clontech, Palo Alto, Calif., Cat. No. K1807-1) and made with maize genomic DNA (see SOP). The following cycling parameters were used in an MJR Tetrad thermocycler with a ramp time of 1 C/sec: 94 C 1 minute, 7 cycles of 94 C 4 seconds, 72 C 3 min, and 33 cycles 94 C 4 seconds, 68 C 3 minutes. For the nested, secondary PCR reaction, 1 L of the primary reaction was used with gene specific primer SEQ ID NO: 68 and adapter primer SEQ ID NO: 3 in a standard Genome Walker PCR reaction (see SOP) using Expand Hi Fidelity DNA Polymerase (BMB Indianapolis, Ind., Cat. No. 1759078) with the supplied buffer No. 2. The reactions were carried out under the following cycling conditions in an MJR Tetrad thermocycler with a ramp time of 1 C/sec: 94 C 1 minute, 5 cycles of 94 C 4 seconds, 72 C 3 minutes, and 25 cycles of 94 C 4 seconds and 68 C 3 minutes.

Twenty five microliters of the secondary PCR reaction was analyzed by agarose gel electrophoresis and bands of approximately 1300 bp, called 43069-1-1300, and approximately 720 bp, called 43069-1-720, were cut out and purified using Supelco Genelute columns (Sigma, St. Louis, Mo., Cat No. 5-6500). Three microliters of the purified bands were ligated to 50 ng of pGEM-T-Easy vector (Promoga, Madison, Wis., Cat. No. A1360). DNA from individual clones was isolated using the Qiagen Plasmid Mini kit (Qiagen, Valencia, Calif., Cat. No. 12125) and sequenced by the Genome Sequencing Center. The ~1300 bp promoter for clone ID 43069-1 is SEQ ID NO: 61. The ~720 bp promoter is SEQ ID NO: 62.

Example 4

Promoter Isolation and Cloning

The DNA fragments resulting from the nested PCR amplification described above are isolated and gel purified. A 25 µL aliquot of the secondary PCR is run on an agarose gel. The DNA fragment of the secondary PCR product is purified from the agarose gel using the Qiagen Kit following the conditions suggested by the manufacturer. The purified DNA is ligated to pGEM-T Easy vector (pGEM-T Easy Vector System I, Promega Corp., Madison, Wis.) following the conditions recommended by the manufacturer. An aliquot of the ligation reaction is transformed into a suitable *E. coli* host such as DH5alpha and the cells plated on selection medium (for DH5alpha, 100 g/mL carbenicillin). Bacterial transformants are selected, grown in liquid culture, and the plasmid DNA isolated using a commercially available kit such as the Qiaprep Spin Microprep Kit (Qiagen Corp., Valencia, Calif.). Purified plasmid containing the predicted insert size based on restriction enzyme analysis are sequenced using the dye terminator method in both directions using the M13 forward and reverse primers (Promega, Madison, Wis., Cat. NOs Q5391 and Q5401, respectively). Restriction enzymes are available from a number of manufacturers (see, for example, Boehringer Mannheim (Indianapolis, Ind.). The 5' flanking regions containing the promoter sequences are determined and shown in SEQ ID NOs: 35-62. Engineering restriction sites for cloning into suitable vectors is done using standard molecular biology techniques known to those skilled in the art.

Example 5

Transient Analysis of Promoter Activity in Protoplasts and Microspores

For transient expression, promoter fragments are cloned into expression vectors such as pMON19469 shown in FIG. 1. Plasmid pMON19469 is an expression vector consisting of the following genetic components: P-e35S is the promoter for the 35S RNA from CaMV containing a duplication of the −90 to −300 region; HSP70 intron is the intervening sequence of the maize heat shock protein as described in U.S. Pat. Nos. 5,593,874 and 5,859,347; GUS: 1 is the coding region for beta-glucuronidase; nos 3' is the termination signal from the nopaline synthase gene; ori-M13 and ori-pUC are origins of replication; AMP is the coding region for ampicillin selection. If a translational start codon of a target promoter is identified, the fragment is cloned into pMON19469 in place of the P-e35S genetic element. If an AUG is not identified, the promoter fragment is cloned into an expression vector modified to enable translational fusions with a reporter gene such as β-glucuronidase (GUS) (Jefferson et al., EMBO J. 6: 3901, 1987) or green fluorescent protein (GFP) as described in Pang et al. (Plant Physiol. 112: 893, 1996).

The expression constructs are tested in a transient plant assay. A number of assays are available and known to those skilled in the art. Analysis of reporter genes in a protoplast system can be used to assess the activity of a regulatory element, such as a promoter operably linked to the reporter gene. A leaf protoplast isolation and electroporation protocol is followed essentially as described by Sheen (The Plant Cell 3: 225-245, 1991) with the following modifications: the seed used is FR27RHM×FRMo17RHM from Illinois Foundation Seeds. The seed is surface sterilized for 2 minutes in 95% ethanol, rinsed twice with sterile water, 30 minutes in 50% bleach (Clorox) plus 2 drops of Tween-20, three rinses in sterile water followed by a 5-minute soak in benlate/captan solution to prevent fungal growth. The seeds are germinated in phytotrays containing 100 ml ½ MS media (2.2 g/L MS salts, 0.25% gelrite), 7 seeds per phytotray. The seeds are grown 5 days at 26° C. in 16/8 hour day/night photoperiod and 7 days in the dark at 28° C. The second leaf from each plant is sliced longitudinally using Feather No. 11 surgical blades. Digestion time is two hours and 10 minutes in the light at 26° C. After digestion, the plates are swirled two times at 80-100 rpm for 20 seconds each and the protoplast/enzyme solution is pipetted through a 190 µm tissue collector. Protoplasts are counted using a hemacytometer counting only protoplasts that are intact and circular. Ten to fifty micrograms of DNA containing the vector of interest is added per cuvette. Final protoplast densities at electroporation range from $3 \times 10^6$/mL to $4.5 \times 10^6$/mL. Electroporations are performed in the light using Bio-Rad Gene pulser cuvettes (Bio-Rad Hercules, Calif.) with a 0.4 cm gap and a maximum volume of 0.8 mL at 125 µFarads capacitance and 260 volts. The protoplasts are incubated on ice after resuspension in electroporation buffer and are kept on ice in cuvettes until 10 minutes after electroporation. The protoplasts are kept at room temperature for ten minutes before adding 7 mL of protoplast growth medium. The protoplast culture medium has been described (Fromm et al., Meth. Enzymol. 153: 351-366, 1987). Culture plates are layered with the growth medium and 1.5% Sea-Plaque agarose (FMC BioProducts, Rockland, Me.) to prevent protoplast loss. Samples are cultured in the light at 26° C., 16/8 day/night cycle, until harvested for the assay (typically 18-22 hours after electroporation). Samples are pipetted from the petri plates to 15 mL centrifuge tubes and harvested by centrifugation at 800-1000 rpm. The supernatant is removed and samples are assayed immediately for the gene of interest. Samples can also be frozen for later analysis.

For analysis of promoter activity in a wheat protoplast system, the method for isolation and preparation of wheat protoplasts is performed as described by Zhou et al. (Plant Cell Reports 12: 612, 1993). The electroporation buffer used has been described (Li et al., 1995). The culture medium used is MS1 MSM (4.4 g Gibco MS salts/L, 1.25 ml Thiamine HCL (0.4 mg/mL), 1 mL 2,4-D (1 mg/mL), 20 g/L sucrose, 0.15 mL asparagine (15 mg/mL), 0.75 g MgCl$_2$. 109 g/L 0.6M mannitol, pH5.5. Mustang protoplasts are used for protoplast isolation about four days after subculture. Briefly, 8 g of wheat cell suspension is poured into a culture tube, the cells are allowed to settle. The medium is removed and remaining cells are resuspended with 40 mL enzyme solution, transferred to a petri plate, wrapped in foil, and incubated at 26° C. for 2 hours on a rotator at 40 rpm. The suspension is centrifuged at 200 g for 8 min., washed twice with centrifugation between each wash, resuspended in 10 mL wash solution and stored on ice. The number of protoplasts is determined and the volume adjusted to a final concentration of $4 \times 10^6$ protoplasts/ml. About 0.75 mL of protoplasts is added to each electroporation cuvette and up to about 50 µg plasmid DNA of the vector in 50 µL solution is added to the protoplasts. The electroporation conditions are 960 µFarads and 160 volts using a Bio-Rad Gene Pulser (Bio-Rad Laboratories, Hercules, Calif.). The samples remain on ice for 10 minutes prior to and during electroporation. After electroporation, the samples are left on ice for about 10 minutes and removed and allowed to warm to room temperature for 10 minutes. The electroporated cells are pipetted into MS1 WSM medium and incubated in the dark for 18-22 hours at 24° C. The cells are harvested by centrifugation at 200-250 g for 8 minutes and frozen on dry ice for subsequent analysis of expression of the gene of interest.

In another transient assay system, barley microspores are used. For this assay shoots are collected and spikes are removed from the sheath and placed in 15×100 mm plates. Fifteen microliters of 0.3 M ice-cold mannitol is added into each plate containing 10 spikes. The plates are sealed with parafilm and kept at 4° C. for 3-4 days. Pre-treated spikes are cut about 1-2 cm into a chilled blender cup (about 10 two-rowed spikes needed/plate). The spikes are covered with enough cold mannitol to create slurry and blended at low speed in a Waring blender for 6-10 seconds. The slurry is filtered through cheesecloth or a nylon membrane and the filtrate is filtered through a 100 μm mesh nylon membrane into a 50 mL centrifuge tube. The mixture is spun for 5 minutes at 900 rpm and the liquid is decanted and microspore pellet resuspended in 2 mL liquid FHG medium. The microspores are filtered through three layers of Whatman No. 2 filter paper into a filtering flask under vacuum. About 2 mL microspores are dropped on each filter set and the uppermost filter paper is transferred to solid medium (FHG+0.25 M mannitol+0.25 M sorbitol on a 15×100 mm plate). The plates are sealed with parafilm and incubated in the dark at 25° C. for 3-4 hours prior to particle bombardment. A number of methods of particle bombardment can be used (see, for example, Klein et al., Bio/Technology 6: 559, 1988; Christou, Particle Bombardment for Genetic Engineering of Plants, Academic Press, 1996). After bombardment, the plates are sealed and kept at 25° C. for 20-24 hours. 0.3 M mannitol solution is used to wash microspores from the filter paper and the microspores are collected by centrifugation and analyzed for expression of the gene of interest. The FHG medium recipe is as follows: Macroelements (mg/L) include, 1900 mg KNO, 165 mg $NH_4NO_3$, 170 mg $KH_2PO_4$, 370 mg $MgSO_47H_2O$, 440 mg $CaCl_22H_2O$; Microelements (mg/L) include 40 mg FeNa.EDTA, 22.3 mg $MnSO_4.5H_2O$, 6.2 mg $H_3B0_3$, 8.6 mg $ZnSO_4$, 0.025 $CuSO_4.5H_2O$, 0.25 mg $NaM004.2H_2O$.

Example 6

Transient Analysis of Promoter Activity in Wheat Reproductive Tissues

For analysis of promoter activity in wheat reproductive tissues such as wheat anthers and ovaries, constructs containing the potential promoter, the HSP70 intron and the GUS gene are bombarded into wheat anthers and ovaries from wheat spikes in which the boot is just beginning to open. One spike of anthers and ovaries is dissected per plate (1 liter plate media: 4.4 g MS salt, 40 g maltose, 40 g raffinose, 22.78 g mannitol, 1.95 g MES, 4 g phytagel at pH 5.8). Two and a half micrograms of each DNA sample (1 μg/μL) to be tested is precipitated with 12.5 μL tungsten, 5.0 μL 0.1M spermidine and 12.5 μL 1.0M calcium chloride for 40 minutes at room temperature. For gunpowder bombardments, 12.5 μL of the supernatant is removed and remainder of sample is sonicated before each shot. 2.5 μL of the DNA precipitant is bombarded per shot. For the helium gun bombardments, the precipitated DNA is spun down, washed with 70% EtOH, washed with 100% EtOH and resuspended in 40 μL 100% EtOH. Five microliters of the DNA is bombarded per plate. For either gun, each plate is shot twice, and two plates are assayed per DNA sample. After bombardment, the plates are incubated overnight at 24° C. in the dark. The next day the anther and ovaries are transferred to a GUS staining solution. To increase the penetration of the staining solution, the samples are put in a vacuum chamber for 10 minutes. Anthers and ovaries are incubated in the staining solution at 37° C. for 16-24 hours. The staining solution is replaced with 70% EtOH, and the tissues are stored at 4° C. Staining is strictly qualitative, either there is expression or not. The staining indicates nothing of the tissue specificity of the potential promoters in stable plates, because the wheat ovary is a very promiscuous tissue that allows many active promoters to be expressed in this transient system.

Example 7

Promoter Activity from Transient Assay Analysis

In general, transcriptional regulatory elements necessary for promoter activity are located within a few hundred bases of the transcriptional start site. In many plant promoters, regulatory elements sufficient for driving heterologous gene expression in a spatial and temporal pattern that mimics the expression of the endogenous gene are located within 1000 base pairs 5' of the transcriptional start site (i.e., AP3, pi, lat52, lat59). There are some genes, however, where transcriptional regulatory elements can be located kilobases away, 5' or 3' to the transcriptional start site.

The transient assay is a system well suited to determining if sufficient regulatory elements are present for transcription initiation. As described in Examples 5 and 6, a DNA fragment is operationally linked to a reporter gene of interest and that construct is "placed" (through particle bombardments, electroporation, etc) into cells, protoplasts or tissues. Expression of the reporter gene in the recipient cells indicates that enough regulatory sequences reside in the DNA fragment to initiate transcription. Thereby, the DNA fragment can be considered a promoter. The transient assay does not provide any data regarding the pattern of gene expression the promoter fragment would provide in vivo. A prediction of the promoter's activity can be made based on the pattern of the endogenous gene's activity, but the accuracy of this prediction is dependent on whether the promoter fragment contains all the necessary regulatory elements responsible for the proper expression of the endogenous gene.

A negative result in a transient assay does not necessarily indicate that a tested DNA fragment has no promoter activity. In addition to experimental error, some of the conditions that could result in a negative result are: 1). a translational start codon is located within the DNA fragment thereby blocking expression of the reporter gene; 2). the DNA fragment contains a transcriptional start site and a splice donor site, but lacks a splice acceptor site. Therefore, the reporter gene is not expressed because the message is not properly spliced; 3). transcription factors specific to the function of the promoter region may not be present in the tissues used for the transient assay; or 4). the level of transcription is below the limits of detection of the assay.

To test the DNA fragments contained in Example 3 for promoter activity, SEQ ID NOs: 35-49 and SEQ ID NOs: 56-62 are assayed by particle bombardment of wheat reproductive tissue (see Example 9). As described in Examples 5, the experimental cassette used to test each putative promoter fragment contains the fragment operationally linked to the hsp70 intron and the GUS gene. The data is summarized in Table 2. The experiment for each, construct is carried out at least 2 times. A construct containing the rice actin promoter operationally linked to the hsp70 intron and GUS gene is used as a positive control and a no-DNA bombardment is used as a negative control.

Table 3. Summary of transient assay data testing for promoter activity of the DNA fragments containing SEQ ID NOs: 35-49 and SEQ ID NOs: 56-62. In the first column are the Clone IDs of the EST sequences used to isolate the promoter fragments (see Example 3). In the second column are the SEQ ID numbers of the fragments tested in the transient assay. The construct names are listed in the third column. Each construct contains a fragment operably linked to the hsp70 intron and GUS gene. The Fourth column indicates the organism in which the assay is conducted. The fifth column is the level of GUS activity detected based on a qualitative evaluation of the number and intensity of positively staining cells in the assay. Low indicates much lower than 35S, medium indicates slightly lower than 35S, and high indicates greater than or equal to 35S.

| Clone ID | SEQ ID NO | pMON number | Organism | Level of Activity |
|---|---|---|---|---|
| 1674-10 | 56 | 48102 | wheat reproductive tissue | low |
|  | 56 | 48102 | lily | low |
| 1674-19 | 57 | 48101 | wheat reproductive tissue | low |
| 16883-3 | 49 | 58914 | wheat reproductive tissue | med |
| 16883-3 | 48 | 58915 | wheat reproductive tissue | low |
| 3253-1 |  |  | not tested |  |
| 3279-052-A12 |  |  | not tested |  |
| 41140-1 | 43 | 54729 | wheat reproductive tissue | med |
| 41291-1 | 36 | 54772 | wheat reproductive tissue | not detected |
| 41291 | 35 | 54777 | wheat reproductive tissue | not detected |
| 41292-1 | 44 | 54733 | wheat reproductive tissue | low |
| 41786-1 | 47 | 54769 | wheat reproductive tissue | low |
| 41786-1 | 46 | 54770 | wheat reproductive tissue | med |
| 41786-1 | 45 | 54771 | wheat reproductive tissue | med |
| 42672-1 | 37 | 54736 | wheat reproductive tissue | low |
| 42672-1 | 38 | 54741 | wheat reproductive tissue | med |
| 73224d06b2 |  |  | not tested |  |
| 985-1 | 40 | 54730 | wheat reproductive tissue | med |
| 985-1 | 42 | 54731 | wheat reproductive tissue | med |
| 985-1 | 39 | 54732 | wheat reproductive tissue | med |
| 985-1 | 41 | 54740 | wheat reproductive tissue | med |
| 17603-1 | 58 | 54734 | wheat reproductive tissue | low |
| 41551-1 | 60 | 54735 | wheat reproductive tissue | med |
| 43069-1 | 62 | 54742 | wheat reproductive tissue | med |

7a. 1674-10

SEQ ID NO: 56 is operably linked to the hsp70 intron and the GUS gene to generate the construct pMON48102. This construct is tested in the wheat reproductive tissue transient assay. GUS activity is detected at a level of expression much lower than seen with the rice actin promoter but greater than that seen with the no DNA bombardments indicating that SEQ ID NO: 56 has promoter activity.

7b. 1674-19

SEQ ID NO: 57 is operably linked to the hsp70 intron and the GUS gene to generate the construct pMON48101. This construct is tested in the wheat reproductive tissue transient assay. GUS activity is detected at a level of expression much lower than seen with the rice actin promoter but greater than that seen with the no DNA bombardments indicating that SEQ ID NO: 57 have promoter activity.

7c. 16883-3

SEQ ID NO: 49 is a smaller version of the putative promoter SEQ ID NO: 48. SEQ ID 49 is operably linked to the hsp70 intron and the GUS gene to generate the construct pMON58914. SEQ ID NO: 48 is operably linked to the hsp70 intron and the GUS gene to generate the constructs pMON58915. Both the constructs are tested in the wheat reproductive tissue transient assay. With SEQ ID NO: 49 GUS activity is detected at a level slightly below that seen with the rice actin promoter positive control and with SEQ ID 48, GUS activity is detected at a level of expression much lower than seen with the rice actin promoter but greater than that seen with the no DNA bombardments indicating that SEQ ID NO: 48 and SEQ ID NO: 49 have promoter activity.

7d. 41140-1

SEQ ID NO: 43 is operably linked to the hsp70 intron and the GUS gene to generate the construct pMON54729. This construct is tested in the wheat reproductive tissue transient assay. GUS activity is detected at a level slightly below that seen with the rice actin promoter positive control indicating that SEQ ID NO: 43 have promoter activity.

7e. 41291

SEQ ID NO: 36 is a smaller version of the putative promoter SEQ ID NO: 35. SEQ ID 36 is operably linked to the hsp70 intron and the GUS gene to generate the construct pMON54722. SEQ ID NO: 35 is operably linked to the hsp70 intron and the GUS gene to generate the constructs pMON54777. Both the constructs are tested in the wheat reproductive tissue transient assay. GUS activity is not detected which could be due to any of the reasons described above.

7f. 41292-1

SEQ ID NO: 44 is operably linked to the hsp70 intron and the GUS gene to generate the construct pMON54733. This construct is tested in the wheat reproductive tissue transient assay. GUS activity is detected at a level of expression much lower than seen with the rice actin promoter but greater than that seen with the no DNA bombardments indicating that SEQ ID NO: 44 have promoter activity.

7g. 41786-1

SEQ ID NO: 46 and SEQ ID NO: 47 are smaller versions of the putative promoter SEQ ID NO: 45. SEQ ID 46 is operably linked to the hsp70 intron and the GUS gene to generate the construct pMON54770. SEQ ID NO: 47 is operably linked to the hsp70 intron and the GUS gene to generate the constructs pMON54769. SEQ ID NO: 45 is operably linked to the hsp70 intron and the GUS gene to generate the construct pMON54771. The constructs are tested in the wheat reproductive tissue transient assay. With SEQ ID NO: 45 and SEQ ID NO: 46, GUS activity is detected at a level slightly below that seen with the rice actin promoter positive control and with SEQ ID 47, GUS activity is detected at a level of expression much lower than seen with the rice actin promoter but greater than that seen with the no DNA bombardments indicating that SEQ ID NO: 45, SEQ ID NO: 46, and SEQ ID NO: 47 have promoter activity.

7h. 42672-1

SEQ ID NO: 38 is a smaller version of the putative promoter SEQ ID NO: 37. SEQ ID 38 is operably linked to the hsp70 intron and the GUS gene to generate the construct pMON54741. SEQ ID NO: 37 is operably linked to the hsp70 intron and the GUS gene to generate the constructs pMON54736. Both the constructs are tested in the wheat reproductive tissue transient assay. With SEQ ID NO: 38 GUS activity is detected at a level slightly below that seen with the rice actin promoter positive control and with SEQ ID 37, GUS activity is detected at a level of expression much lower than seen with the rice actin promoter but greater than that seen with the no DNA bombardments indicating that SEQ ID NO: 37 and SEQ ID NO: 38 have promoter activity.

7i. 985-1

SEQ ID NO: 40, SEQ ID NO: 41, and SEQ ID NO: 42 are smaller versions of the putative promoter SEQ ID NO: 39. SEQ ID 40 is operably linked to the hsp70 intron and the GUS gene to generate the construct pMON54730. SEQ ID NO: 41 is operably linked to the hsp70 intron and the GUS gene to generate the constructs pMON54740. SEQ ID NO: 42 is operably linked to the hsp70 intron and the GUS gene to generate the construct pMON54731. SEQ ID NO: 39 is operably linked to the hsp70 intron and the GUS gene to generate the construct pMON54732. These constructs are tested in the wheat reproductive tissue transient assay. GUS activity is detected at a level slightly below that seen with the rice actin promoter positive control indicating that SEQ ID NO: 39, SEQ ID NO: 40 SEQ ID NO: 41, and SEQ ID NO: 42 have promoter activity.

7j. 17603-1

SEQ ID NO: 58 is operably linked to the hsp70 intron and the GUS gene to generate the construct pMON54734. This construct is tested in the wheat reproductive tissue transient assay. GUS activity is detected at a level of expression much lower than seen with the rice actin promoter but greater than that seen with the no DNA bombardments indicating that SEQ ID NO: 58 have promoter activity.

7k. 41551-1

SEQ ID NO: 60 is a smaller version of the putative promoter SEQ ID NO: 59. SEQ ID NO: 60 is operably linked to the hsp70 intron and the GUS gene to generate the construct pMON547345 and the construct was tested in the wheat reproductive tissue transient assay. GUS activity is detected at a level slightly below that seen with the rice actin promoter positive control indicating that SEQ ID NO: 60 have promoter activity. Because SEQ ID NO: 60 is a smaller version of SEQ ID NO: 59, it is presumed that SEQ ID NO: 59 has promoter activity as well.

7l. 43069-1

SEQ ID NO: 62 is a smaller version of the putative promoter SEQ ID NO: 61. SEQ ID NO: 62 is operably linked to the hsp70 intron and the GUS gene to generate the construct pMON547345 and the construct was tested in the wheat reproductive tissue transient assay. GUS activity is detected at a level slightly below that seen with the rice actin promoter positive control indicating that SEQ ID NO: 62 have promoter activity. Because SEQ ID NO: 62 is a smaller version of SEQ ID NO: 61, it is presumed that SEQ ID NO: 61 has promoter activity as well.

Example 8

Promoter Activity Analysis in Stably Transformed Plants

Figure 2:
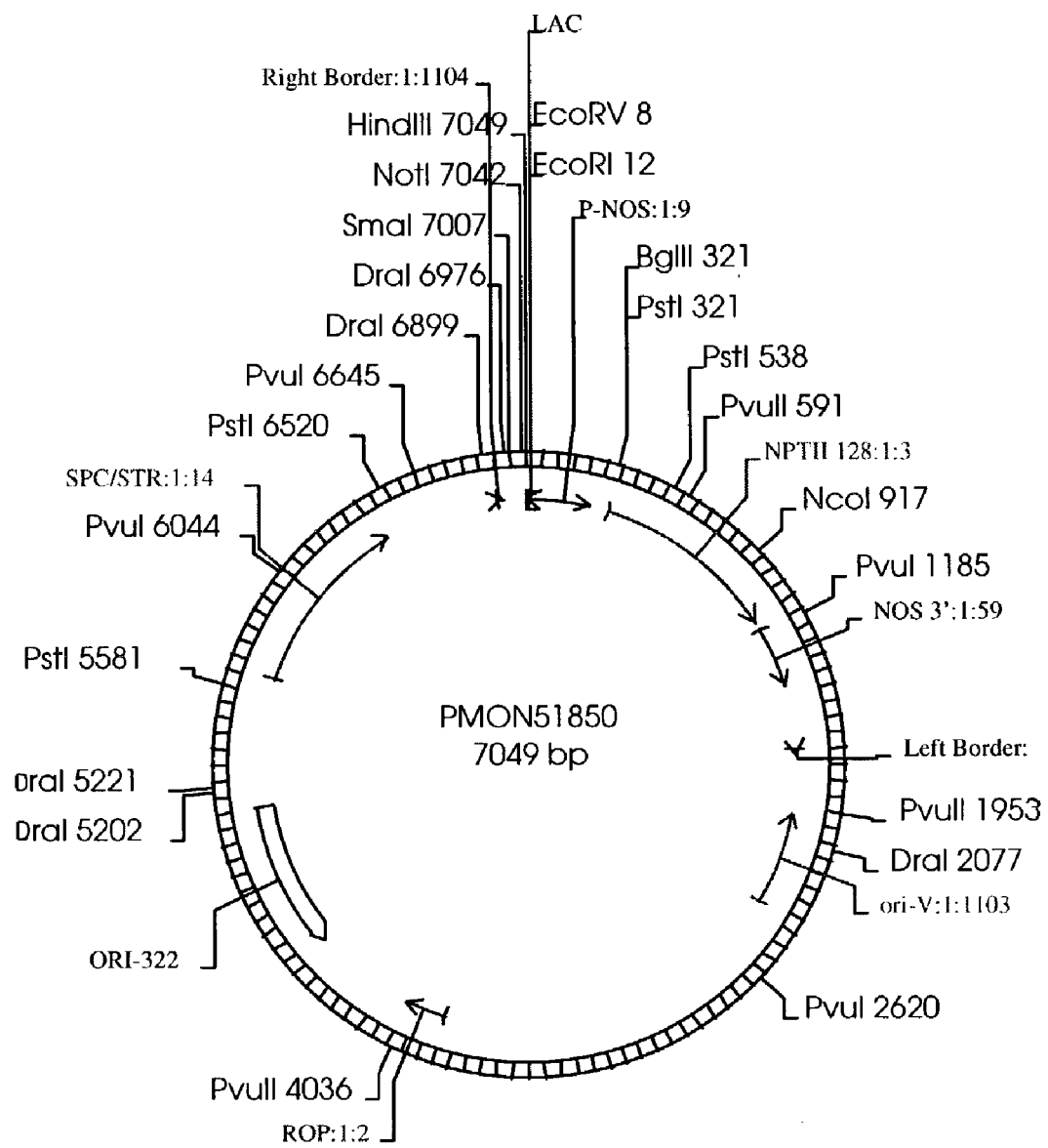
FIG. 2 is a plasmid map of pMON51850.

For stable plant transformation the 5' regulatory sequences are cloned into a plant transformation vector such as shown in FIG. 2. Plasmid pMON51850 is a double border (right and left T-DNA borders) plant transformation vector and contains the following genetic components: NOs 3' is the termination signal from the nopaline synthase gene; ori-322 and ori-V are origins of replication; kan is the coding region for kanomycin selection.

The promoter is operably linked to any gene of interest such as a glyphosate tolerance gene along with other regulatory sequences including, but not limited to, non-translated leaders and terminators as described above, and transformed into a target crop of interest via an appropriate delivery system such as Agrobacterium-mediated transformation (see, for example, U.S. Pat. Nos. 5,569,834, 5,416,011, 5,631,152, 5,159,135 and 5,004,863) or particle bombardment methods (see, for example, PCT Pat. publications WO 92/15675 and WO 97/48814, European Patent Application EP586,355, and U.S. Pat. Nos. 5,120,657, 5,503,998, 5,830,728 and 5,015, 580). A large number of transformation and regeneration systems and methods are available and well known to those skilled in the art. The stably transformed plants and progeny are subsequently analyzed for expression of the gene in tissues of interest by any number of molecular, immunodiagnostic, biochemical, and/or field evaluation methods known to those skilled in the art.

The transient assay test described in Example 7 gives qualitative data regarding the promoter activity of the DNA fragments tested. The transient assay does not indicate whether the isolated promoters will act as predicted in vivo. To determine the promoter activity in male reproductive tissues, the promoter fragments are cloned upstream of a gene of interest (either GUS or the MS2 coat protein), placed in a plant transformation vector and transformed into plants (as described in Example 6). Tissue from R0 plants are harvested and assayed for the gene of interest.

Detection of GUS activity in male reproductive tissues is referenced in Example 5. For the detection of the MS2 coat protein, anther extracts are analyzed by immunodetection on Western blots or ELISA analysis. For Western blots, the T7 tag monoclonal and horseradish peroxidase conjugated antibody (Novagen) is used to detect MS2 protein expression in anther tissues. Total protein is extracted (extraction buffer: 1×PBS and 0.01% Tween-20) from anther, 10 µg of total protein sample is separated on a 10-20% polyacrylamide gradient gel (BioRAD) and transferred onto ECL nitrocellulose membrane (Amersham). A 1:5000 dilution of primary antisera is used to detect ACOX protein using the ECL detection system (Amersham). A 15 Kd protein is detected.

For ELISA quantification of MS2 coat protein levels in anthers, crude anther extracts containing 1 µg total protein is added a 96-well Nunc-lmmuno MaxiSorb plate coated with 100 µL of purified polyclonal anti-MS2 coat protein IgG antibody (0.1 ng/µl) in coating buffer (15 mM $Na_2CO_3$, 35 mM $NaHCO_3$, pH 9.6). The plate is sealed and incubated at 37° C. for one hour. The plate is then rinsed three times with PBT (1×PBS, 0.05%, and Tween 20, pH7.4). Fifty microliters of the anther extract containing 1 µg of total protein is added to a well, followed by addition of 50 µL of a 1:10,000 dilution of anti-T7 tag monoclonal and HSP conjugated antibody (Novagen). The loaded plate is incubated at 37° C. for one hour then rinsed three times with PBT. To develop the plate, 100 µL of substrate (a 1:1 mixture of $H_2O_2$ and TMB (3,3'-5, 5'-tetra methyl benzidine), Kirgeggard and Perry, No. 50-76-03, Gaithersburg, Md.) is added to each well and the plate is incubated at room temperature for 3-5 min. One hundred microliters of stop solution (3M $H_3PO_4$) is added to terminate the reaction. The plate is read on a Spectra Max 340 (Molecular Devices, Sunnyvail, Calif. 94089) at 450 nm.

Plasmids can be transformed into two types of angiosperms: monocots or dicots. The promoter fragments are derived from *Zea mays* (corn), a monocot plant. Therefore, activity in a dicot plant would indicate a broad spectrum of plants in which the promoter is active. The dicot plant *Arabidopsis thaliana* offers several advantages as a model system to study promoter systems: ease of transformation, quick life cycle, and multiple stages of floral development on each plant. Promoters that are active in Arabidopsis anthers are likely to be active in many monocot and dicot species. To test this, some promoters that are active in Arabidopsis are also tested in monocot plants. As shown below and summarized in Table 3, all promoter fragments tested that are active in Arabidopsis are also active in monocots. Therefore, if the corn promoter fragment is active in Arabidopsis, it is likely to be active in monocots as well.

Table 4. Summary of promoter activity in stably transformed plants. In the first column are the Clone IDs of the EST sequences used to isolate the promoter fragments (see Example 3). The second column shows the SEQ ID numbers of the fragments tested in the transient assay. The third column lists the introns used in the constructs. No introns are used in constructs for dicot transformation. The fourth column lists the pMON number of each vector constructed. The fifth column lists the reporter genes used in the constructs. In the sixth column are the organisms transformed. The seventh column shows the type of assay used to detect the reporter gene. The eighth column shows the number of plants assayed. The ninth column shows the number of plants showing male expression and the last column lists any other tissues in which the reporter protein is detected.

pendent events. These data indicate that SEQ ID NO: 57 can act as an anther-enhanced promoter in dicots. To test for anther activity in monocots, SEQ ID NO: 57 is placed upstream of the hsp70 intron/MS2 coat protein gene cassette and put into a plant transformation vector resulting in the constructs pMON42934 and pMON52001. These construct are used to transform wheat, rice and/or corn. Wheat anthers tested positive for MS2 coat protein in 4 of 6 independent R0 wheat plants as assayed by Western blot for MS2 coat protein with pMON42934 and 2 of 3 independent wheat lines with pMON52001. Corn anthers tested positive for MS2 coat protein in 4 of 11 independent R0 corn plants as assayed by Western blot for MS2 coat protein with pMON42934. Rice anthers tested positive for MS2 coat protein in 3 of 6 independent R0 rice plants as assayed by Western blot for MS2 coat protein with pMON52001. These data indicate that SEQ ID NO: 57 can act as an anther-enhanced promoter in both monocot and dicot plants.

8c. 16883-3

To test for anther activity in dicot plants SEQ ID NO: 48 is placed upstream of the GUS gene and put into a plant transformation vector resulting in the construct pMON58948. This construct is used to transform *Arabidopsis thaliana*. Three of

| Clone ID | SEQ ID NO | Intron | pMON number | Exp. Gene | Organism | Assay | No. Plants assayed | Male positive | Other |
|---|---|---|---|---|---|---|---|---|---|
| 1674-10 | 56 | hsp70 | 48109 | GUS | wheat | X-Gluc | 16 | 7 | female tissue |
| 1674-19 | 57 | hsp70 | 48112 | GUS | wheat | X-Gluc | 4 | 3 | |
| | 57 | none | 48182 | GUS | *Arabidopsis* | X-Gluc | 6 | 5 | |
| | 57 | hsp70 | 42934 | MS2 | corn | Western | 11 | 4 | |
| | 57 | hsp70 | 42934 | MS2 | wheat | Western | 6 | 4 | |
| | 57 | hsp70 | 52001 | MS2 | wheat | Western | 3 | 2 | |
| | 57 | hsp70 | 52001 | MS2 | rice | Western | 6 | 3 | |
| 16883-3 | 48 | none | 58948 | GUS | *Arabidopsis* | X-Gluc | 4 | 3 | |
| 3253-1 | 51 | none | 58966 | GUS | *Arabidopsis* | X-Gluc | 1 | 1 | 1/1 in leaf trichomes |
| 3279-052-A12 | 53 | none | 58970 | GUS | *Arabidopsis* | X-Gluc | 9 | 8 | 3/9 in leaf |
| 41140-1 | 43 | none | 54757 | GUS | *Arabidopsis* | X-Gluc | 7 | 4 | |
| 41291-1 | 35 | none | 54783 | GUS | *Arabidopsis* | X-Gluc | 2 | 1 | |
| 41292-1 | 44 | none | 54758 | GUS | *Arabidopsis* | X-Gluc | 8 | 1 | |
| 41786-1 | 47 | none | 54779 | GUS | *Arabidopsis* | X-Gluc | 9 | 2 | |
| 41786-1 | 46 | none | 54780 | GUS | *Arabidopsis* | X-Gluc | 9 | 8 | |
| 41786-1 | 45 | none | 54781 | GUS | *Arabidopsis* | X-Gluc | 5 | 4 | |
| 42672-1 | 38 | none | 54768 | GUS | *Arabidopsis* | X-Gluc | 7 | 1 | |
| 42672-1 | 37 | none | 54767 | GUS | *Arabidopsis* | X-Gluc | 7 | 1 | |
| 73224d06b2 | 55 | none | 58971 | GUS | *Arabidopsis* | X-Gluc | 4 | 4 | 1/4 in leaf |
| 985-1 | 40 | none | 54760 | GUS | *Arabidopsis* | X-Gluc | 8 | 1 | |
| 41551-1 | 60 | none | 54754 | GUS | *Arabidopsis* | GUS | 8 | 0 | |

8a. 1674-10

To test for anther activity in monocot plants, SEQ ID NO: 56 is placed upstream of the hsp70 intron/GUS gene cassette and put into a plant transformation vector resulting in the construct pMON48109. This construct is used to transform wheat. Anthers from 16 R0 wheat plant are assayed for GUS expression. These data indicate that SEQ ID NO: 56 can act as an anther and female enhanced promoter in monocots.

8b. 1674-19

To test for anther activity in dicot plants SEQ ID NO: 57 is placed upstream of the GUS gene and put into a plant transformation vector resulting in the construct pMON48182. This construct is used to transform *Arabidopsis thaliana*. Gus expression is detected in anther tissue in five out of six indefour independent events show expression in the male reproductive tissues. These data indicate that SEQ ID NO: 48 can act as an anther-enhanced promoter in dicots. Because it is monocot-derived promoter, it is likely to be active in monocot anthers as well.

8d. 3253-1

To test for anther activity in dicot plants SEQ ID NO: 51 is placed upstream of the GUS gene and put into a plant transformation vector resulting in the construct pMON58966. This construct is used to transform *Arabidopsis thaliana*. One of one independent event shows expression in the male reproductive tissues. GUS expression is detected in the leaf trichomes. These data indicate that SEQ ID NO: 51 can act as an anther-enhanced promoter in dicots. Because it is monocot-derived promoter, it is likely to be active in monocot anthers as well.

8e. 3279-052-a12

To test for anther activity in dicot plants SEQ ID NO: 53 is placed upstream of the GUS gene and put into a plant transformation vector resulting in the construct pMON58970. This construct is used to transform *Arabidopsis thaliana*. Eight of nine independent events show expression in the male reproductive tissues. GUS expression is detected in three of nine events in the leaf. These data indicate that SEQ ID NO: 53 can act as an anther-enhanced promoter in dicots. Because it is monocot-derived promoter, it is likely to be active in monocot anthers as well.

8f. 41140-1

To test for anther activity in dicot plants SEQ ID NO: 43 is placed upstream of the GUS gene and put into a plant transformation vector resulting in the construct pMON54757. This construct is used to transform *Arabidopsis thaliana*. Four of seven independent events show expression in the male reproductive tissues. These data indicate that SEQ ID NO: 43 can act as an anther-enhanced promoter in dicots. Because it is monocot-derived promoter, it is likely to be active in monocot anthers as well.

8g. 41291-1

To test for anther activity in dicot plants SEQ ID NO: 35 is placed upstream of the GUS gene and put into a plant transformation vector resulting in the construct pMON54783. This construct is used to transform *Arabidopsis thaliana*. One of two independent events shows expression in the male reproductive tissues. These data indicate that SEQ ID NO: 35 can act as an anther-enhanced promoter in dicots. Because it is monocot-derived promoter, it is likely to be active in monocot anthers as well.

8h. 41292-1

To test for anther activity in dicot plants SEQ ID NO: 44 is placed upstream of the GUS gene and put into a plant transformation vector resulting in the construct pMON54758. This construct is used to transform *Arabidopsis thaliana*. One of eight independent events shows expression in the male reproductive tissues. These data indicate that SEQ ID NO: 44 can act as an anther-enhanced promoter in dicots. Because it is monocot-derived promoter, it is likely to be active in monocot anthers as well.

8i. 41786-1

To test for anther activity in dicot plants SEQ ID NOs: 45-47 are placed upstream of the GUS gene and put into a plant transformation vector resulting in the constructs pMON54781, pMON54780, and pMON54779, respectively. These constructs are used to transform *Arabidopsis thaliana*. Four of five independent events show expression in the male reproductive tissues with pMON54781, eight of nine independent events show expression in the male reproductive tissues with pMON54780, and two of nine independent events show expression in the male reproductive tissues with pMON54779. These data indicate that SEQ ID NOs: 45-47 can act as an anther-enhanced promoter in dicots. Because it is monocot-derived promoter, it is likely to be active in monocot anthers as well.

8j. 42672-1

To test for anther activity in dicot plants SEQ ID NOs: 37-38 are placed upstream of the GUS gene and put into a plant transformation vector resulting in the constructs pMON54767 and pMON54768, respectively. These constructs are used to transform *Arabidopsis thaliana*. One of seven independent events shows expression in the male reproductive tissues with pMON54767, and one of seven independent events show expression in the male reproductive tissues with pMON54768. These data indicate that SEQ ID NOs: 37-38 can act as an anther-enhanced promoter in dicots. Because it is monocot-derived promoter, it is likely to be active in monocot anthers as well.

8k. 73224d06b2

To test for anther activity in dicot plants SEQ ID NO: 55 is placed upstream of the GUS gene and put into a plant transformation vector resulting in the construct pMON58971. This construct is used to transform *Arabidopsis thaliana*. Four of four independent events show expression in the male reproductive tissues. One of four independent events shows expression in the leaf. These data indicate that SEQ ID NO: 55 can act as an anther-enhanced promoter in dicots. Because it is monocot-derived promoter, it is likely to be active in monocot anthers as well.

8l. 985-1

To test for anther activity in dicot plants SEQ ID NO: 40 is placed upstream of the GUS gene and put into a plant transformation vector resulting in the construct pMON54760. This construct is used to transform *Arabidopsis thaliana*. One of eight independent events shows expression in the male reproductive tissues. These data indicate that SEQ ID NO: 40 can act as an anther-enhanced promoter in dicots. Because it is monocot-derived promoter, it is likely to be active in monocot anthers as well.

8m. 41551-1

To test for anther activity in dicot plants SEQ ID NO: 60 is placed upstream of the GUS gene and put into a plant transformation vector resulting in the construct pMON58948. This construct is used to transform *Arabidopsis thaliana*. GUS activity was not detected in any of the eight independent events tested that could be due to any of the reasons described above.

Example 9

Identification of Cis Elements and Engineering Novel Promoters

Cis acting regulatory elements necessary for proper promoter regulation can be identified by a number of means. In one method, deletion analysis is carried out to remove regions of the promoter and the resulting promoter fragments are assayed for promoter activity. DNA fragments are considered necessary for promoter regulation if the activity of the truncated promoter is altered compared to the original promoter fragment. Through this deletion analysis, small regions of DNA can be identified which are necessary for positive or negative regulation of transcription. Promoter sequence motifs can also be identified and novel promoters engineered to contain these cis elements for modulating expression of operably linked transcribable sequences. See for example U.S. Pat. Nos. 5,223,419, 4,990,607, and 5,097,025.

An alternative approach is to look for similar sequences between promoters with similar expression profiles. Promoters with overlapping patterns of activity can have common regulatory mechanisms. Several computer programs can be used to identify conserved, sequence motifs between promoters, including, but not limited to, MEME, SIGNAL SCAN, or GENE SCAN. These motifs can represent binding sites for transcription factors which act to regulate the promoters.

Once the sequence motifs are identified, their function can be assayed. For example, the motif sequences can be deleted from the promoter to determine if the motif is necessary for proper promoter function. Alternatively, the motif can be added to a minimal promoter to test whether it is sufficient to activate transcription. Suspected negative regulatory elements can be tested for sufficiency by adding to an active promoter and testing for a reduction in promoter activity. Some cis acting regulatory elements may require other elements to function. Therefore, multiple elements can be tested in various combinations by any number of methods known to those skilled in the art.

Once functional promoter elements have been identified, promoter elements can be modified at the nucleotide level to affect protein binding. The modifications can cause either higher or lower affinity binding that would affect the level of transcription from that promoter.

Promoter elements can act additively or synergistically to affect promoter activity. In this regard, promoter elements from different 5' regulatory regions can be placed in tandem to obtain a promoter with a different spectrum of activity or different expression profile. Accordingly, combinations of promoter elements from heterologous sources or duplication of similar elements or the same element can confer a higher level of expression of operably linked transcribable sequences. For example, a promoter element can be multimerized to increase levels of expression specifically in the pattern affected by that promoter element.

The technical methods needed for constructing expression vectors containing the novel engineered 5' regulatory elements are known to those of skill in the art. The engineered promoters are tested in expression vectors and tested transiently by operably linking the novel promoters to a suitable reporter gene such as GUS and testing in a transient plant assay. The novel promoters are operably linked to one or more genes of interest and incorporated into a plant transformation vector along with one or more additional regulatory elements and transformed into a target plant of interest by a suitable DNA delivery system. The stably transformed plants and subsequent progeny are evaluated by any number of molecular, immunodiagnostic, biochemical, phenotypic, or field methods suitable for assessing the desired agronomic characteristic(s).

The above describe the inventions. All publications and patents mentioned in this specification are herein incorporated by reference by their whole entireties as if each individual publication or patent is specially and individually stated to be incorporated by reference by its entirety.

What is claimed is:

1. A nucleic acid molecule selected from the group consisting of:
(a) a nucleic acid sequence comprising SEQ ID NO:57;
(b) a nucleic acid sequence comprising a fragment of SEQ ID NO:57 with promoter activity in plant male reproductive tissue;
(c) a nucleic acid sequence comprising at least 95% sequence identity to SEQ ID NO: 57 and promoter activity in plant male reproductive tissue; and
(d) a nucleic acid sequence comprising at least 99% sequence identity to SEQ ID NO: 57 and promoter activity,
wherein the nucleic acid molecule is operably linked to a heterologous, transcribable DNA sequence.

2. A cell comprising a recombinant DNA construct comprising the nucleic acid molecule of claim 1.

3. A transgenic plant comprising a DNA construct comprising the nucleic acid molecule of claim 1.

4. The isolated nucleic acid molecule of claim 1, wherein the nucleic acid molecule comprises SEQ ID NO:57.

5. The isolated nucleic acid molecule of claim 1, wherein the nucleic acid molecule comprises at least 95% sequence identity to SEQ ID NO: 57 and promoter activity in plant male reproductive tissue.

6. The cell of claim 2, wherein the nucleic acid molecule comprises SEQ ID NO:57.

7. The cell of claim 2, wherein the nucleic acid molecule comprises a polynucleotide sequence with at least 95% sequence identity to SEQ ID NO: 57 and promoter activity in plant male reproductive tissue.

8. The transgenic plant of claim 3, wherein the nucleic acid molecule comprises SEQ ID NO:57.

9. The transgenic plant of claim 3, wherein the nucleic acid molecule comprises at least 95% sequence identity to SEQ ID NO: 57 and promoter activity in plant male reproductive tissue.

10. The isolated nucleic acid molecule of claim 1, wherein the nucleic acid molecule comprises at least 99% sequence identity to SEQ ID NO: 57 and promoter activity.

11. The cell of claim 2, wherein the nucleic acid molecule comprises at least 99% sequence identity to SEQ ID NO: 57 and promoter activity.

12. The transgenic plant of claim 3, wherein the nucleic acid molecule comprises at least 99% sequence identity to SEQ ID NO: 57 and promoter activity.

* * * * *

SEQUENCE LISTING

```
<160> NUMBER OF SEQ ID NOS: 68

<210> SEQ ID NO 1
<211> LENGTH: 22
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(22)
<223> OTHER INFORMATION:

<400> SEQUENCE: 1
gtaatacgac tcactatagg gc                                             22

<210> SEQ ID NO 2
<211> LENGTH: 19
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(19)
<223> OTHER INFORMATION:

<400> SEQUENCE: 2
actatagggc acgcgtggt                                                 19

<210> SEQ ID NO 3
<211> LENGTH: 31
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(31)
<223> OTHER INFORMATION:
```

```
<400> SEQUENCE: 3
agggcaagct tggtcgacgg cccgggctgg t                              31

<210> SEQ ID NO 4
<211> LENGTH: 28
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(28)
<223> OTHER INFORMATION:

<400> SEQUENCE: 4
ctcatgccta tggacatagt ctaatcgc                                  28

<210> SEQ ID NO 5
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(39)
<223> OTHER INFORMATION:

<400> SEQUENCE: 5
ggatccagat cttggttaga ggacaaccgt tggaaggag                      39

<210> SEQ ID NO 6
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 6
gcccagagag cggagacggc tcgcttc                                   27

<210> SEQ ID NO 7
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(39)
<223> OTHER INFORMATION:

<400> SEQUENCE: 7
ggatccagat ctctcgactg cagagctgct tggttggcc                      39

<210> SEQ ID NO 8
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:
```

```
<400> SEQUENCE: 8
gtagtgccct gtcccgaccc tcaagcc                                              27

<210> SEQ ID NO 9
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(39)
<223> OTHER INFORMATION:

<400> SEQUENCE: 9
ggatccagat cttcgcctgc tagggcctag ggctcgctc                                 39

<210> SEQ ID NO 10
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 10
tcgcctccag gaggacgact gcaatgc                                              27

<210> SEQ ID NO 11
<211> LENGTH: 42
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(42)
<223> OTHER INFORMATION:

<400> SEQUENCE: 11
ggatccagat ctcgcttttc tctttcagca agatggctgg cc                             42

<210> SEQ ID NO 12
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 12
acaatcacca gggccaaggt ggtggag                                              27

<210> SEQ ID NO 13
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(39)
```

<223> OTHER INFORMATION:

<400> SEQUENCE: 13
ggatccagat ctccaatagc tcgatgctca ggcgctgac                39

<210> SEQ ID NO 14
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 14
ccgactacgt tgcgggctgc gtccagg                27

<210> SEQ ID NO 15
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(39)
<223> OTHER INFORMATION:

<400> SEQUENCE: 15
ggatccagat cttcgccggg gtggcgtcgg cggctacgc                39

<210> SEQ ID NO 16
<211> LENGTH: 28
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(28)
<223> OTHER INFORMATION:

<400> SEQUENCE: 16
ccgccggagc tgatctcaca ggagacgg                28

<210> SEQ ID NO 17
<211> LENGTH: 40
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(40)
<223> OTHER INFORMATION:

<400> SEQUENCE: 17
ggatccagat ctgcaagcgg ggcggagagg aacgaggatc                40

<210> SEQ ID NO 18
<211> LENGTH: 28
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature

```
<222> LOCATION: (1)..(28)
<223> OTHER INFORMATION:

<400> SEQUENCE: 18
tgcctggtgg tcagaatggt ggcctagg                                         28

<210> SEQ ID NO 19
<211> LENGTH: 40
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(40)
<223> OTHER INFORMATION:

<400> SEQUENCE: 19
ggatccagat ctgttggcgg ctggatctgg cctctggctg                            40

<210> SEQ ID NO 20
<211> LENGTH: 28
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(28)
<223> OTHER INFORMATION:

<400> SEQUENCE: 20
tgaagaggcg cttgacgatg tgccggtc                                         28

<210> SEQ ID NO 21
<211> LENGTH: 28
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(28)
<223> OTHER INFORMATION:

<400> SEQUENCE: 21
aaatgttgag gctgctttgc atgcggtc                                         28

<210> SEQ ID NO 22
<211> LENGTH: 37
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(37)
<223> OTHER INFORMATION:

<400> SEQUENCE: 22
ggatccagat ctcgcttgtt tcagctgagt gcagagc                               37

<210> SEQ ID NO 23
<211> LENGTH: 28
<212> TYPE: DNA
<213> ORGANISM: artificial sequence
<220> FEATURE:
<223> OTHER INFORMATION: a fully synthesized primer
<220> FEATURE:
```

```
<221> NAME/KEY: misc_feature
<222> LOCATION: (1)..(28)
<223> OTHER INFORMATION:

<400> SEQUENCE: 23
gtcgtcgtac gggtggagcg gcggccgg                                              28

<210> SEQ ID NO 24
<211> LENGTH: 40
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(40)
<223> OTHER INFORMATION:

<400> SEQUENCE: 24
ggatccagat ctgccgcgga ggtaggcgag tacgaagacg                                 40

<210> SEQ ID NO 25
<211> LENGTH: 17
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(17)
<223> OTHER INFORMATION:

<400> SEQUENCE: 25
gtgcttcatt agtcagc                                                         17

<210> SEQ ID NO 26
<211> LENGTH: 17
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(17)
<223> OTHER INFORMATION:

<400> SEQUENCE: 26
caagaacaag gagcaag                                                         17

<210> SEQ ID NO 27
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 27
gccgtaactg gtctcaccga gcctctc                                              27

<210> SEQ ID NO 28
<211> LENGTH: 27
<212> TYPE: DNA
<213> ORGANISM: artificial sequence
<220> FEATURE:
<223> OTHER INFORMATION: a fully synthesized primer
```

```
<220> FEATURE:
<221> NAME/KEY: misc_feature
<222> LOCATION: (1)..(27)
<223> OTHER INFORMATION:

<400> SEQUENCE: 28
gaagcttcgt ctcgccttca ggtccga                                          27

<210> SEQ ID NO 29
<211> LENGTH: 34
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(34)
<223> OTHER INFORMATION:

<400> SEQUENCE: 29
ttttgtagat cttcaaagcc ccctacacaa cgtg                                  34

<210> SEQ ID NO 30
<211> LENGTH: 17
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(17)
<223> OTHER INFORMATION:

<400> SEQUENCE: 30
gcttgtaatg cttgatg                                                     17

<210> SEQ ID NO 31
<211> LENGTH: 17
<212> TYPE: DNA
<213> ORGANISM: artificial sequence
<220> FEATURE:
<223> OTHER INFORMATION: a fully synthesized primer
<220> FEATURE:
<221> NAME/KEY: promoter
<222> LOCATION: (1)..(17)
<223> OTHER INFORMATION:

<400> SEQUENCE: 31
gaccggactg ttgcctc                                                     17

<210> SEQ ID NO 32
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 32
cgggcgtcgc acgaggagag gagaagg                                          27

<210> SEQ ID NO 33
<211> LENGTH: 27
<212> TYPE: DNA
<213> ORGANISM: artificial sequence
<220> FEATURE:
```

```
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 33
cgggcgtcgc acgaggagag gagaagg                                           27

<210> SEQ ID NO 34
<211> LENGTH: 32
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(32)
<223> OTHER INFORMATION:

<400> SEQUENCE: 34
gcgtgcagat ctggaggagg ctagctacac tt                                     32

<210> SEQ ID NO 35
<211> LENGTH: 1484
<212> TYPE: DNA
<213> ORGANISM: Zea mays
<220> FEATURE:
<221> NAME/KEY: promoter
<222> LOCATION: (1)..(1484)
<223> OTHER INFORMATION:

<400> SEQUENCE: 35
actatagggc gaattgggcc cgacgtcgca tgctcccggc cgccatggcg gccgcgggaa        60
ttcgattagg gcaagcttgg tcgacggccc gggctggtcc tatgtgggat tcagcccact       120
gtaacgggcc ccgcgtggat aagcatgtta caggtcgtgt ctgtaatagc cttttctata       180
atgacggtct gtaacctcct cttgtgagaa tattctggag atagtctggg tacccgaggg       240
cataaacgtc cttgccagag gacggtggtc actcgggtgt ctataaatac cctcgtacag       300
tgcccttgag aggccagatt aatagagcta ttgccattcc ccgttgaact ttgcaaacac       360
tctctccact tccctgtttg atctacttgc ccaggaaggc aagttccaac atttggcgtc       420
aaccgttcgt gctacgaaca ataacccgt gatggcaccc aagcgagcta gttcgaaggc        480
agccccatcc atcgacgaag cagcgaaggc agcgctgctg gctgagaaaa aaggcaaggc       540
cctcgcagac aacaaacccc aagaagcctc cgaagacgaa gctgtcggca acactatcc        600 actcttccgt tggatctact agcccaggaa ggcaagttcc aacacaaata ccagcaacac       660
aaaaataaaa atcggtttct tatttggatg cgttaatcaa gcgagacgtc aactggtact       720
gttatgatct ggataatgcg atatttaaaa tctcaggtac tagtatttgg atcagtaacc       780
ggtttggacc ctctgatgtg agcggcgatc tgtatccact ccgacttcct caacatgaag       840
gcttttcagg caggcatcct ccacagcgtc cttatggcac caatgcctcg gccatcctgc       900
tacttcacaa attctccagt cgttttccta aggctgctgc tcacgcatgc tccgtcgatc       960
atgtcgcctg ggctctcttg cactccatca gggtcttccg atcgagtccc atgcatttca      1020
agtggagtac atcaattaca cgcacacgca tgtacattat aaaaagtaag ctctatgtaa      1080
tttcaaatcg ggtacatata tgttcaatca gttcttttt tttggtttag taaacatgta       1140 ggtattttt tatttggatg ataaagcttg atagcatgaa tctcacccgt tagtctcagg       1200
aacaaattta attattcatc gctttgttgc tcttcctttg tgaaagtaag atgttcttct      1260
```

```
agttctcttt atcatgatag tgtaccacaa cattcacgta gtttgtgtgt ttatcatgct    1320
ttcctcatga ccatacctaa tactttgttt atttaactca acttttggct tctgtgtact    1380
ttcaaatgtc tttacttgtg tgttatgtac tccttccaac ggttgtcctc taaccaagat    1440
ctggatccaa tcactagtga attcgcggcc gcctgcaggt cgac                    1484

<210> SEQ ID NO 36
<211> LENGTH: 732
<212> TYPE: DNA
<213> ORGANISM: Zea mays
<220> FEATURE:
<221> NAME/KEY: promoter
<222> LOCATION: (1)..(732)
<223> OTHER INFORMATION:

<400> SEQUENCE: 36
tcaggtacta gtatttggat cagtaaccgg tttggaccct ctgatgtgag cggcgatctg      60
tatccactcc gacttcctca acatgaaggc ttttcaggca ggcatcctcc acagcgtcct     120
tatggcacca atgcctcggc catcctgcta cttcacaaat tctccagtcg ttttcctaag     180
gctgctgctc acgcatgctc cgtcgatcat gtcgcctggg ctctcttgca ctccatcagg     240
gtcttccgat cgagtcccat gcatttcaag tggagtacat caattacacg cacacgcatg     300
tacattataa aaagtaagct ctatgtaatt tcaaatcggg tacatatatg ttcaatcagt     360 tcttttttt tggtttagta aacatgtagg tattttttta tttggatgat aaagcttgat      420
agcatgaatc tcacccgtta gtctcaggaa caaatttaat tattcatcgc tttgttgctc     480
ttcctttgtg aaagtaagat gttcttctag ttctctttat catgatagtg taccacaaca     540
ttcacgtagt ttgtgtgttt atcatgcttt cctcatgacc atacctaata ctttgtttat     600
ttaactcaac ttttggcttc tgtgtacttt caaatgtctt tacttgtgtg ttatgtactc     660
cttccaacgg ttgtcctcta accaagatct ggatccaatc actagtgaat tcgcggccgc     720
ctgcaggtcg ac                                                         732

<210> SEQ ID NO 37
<211> LENGTH: 2100
<212> TYPE: DNA
<213> ORGANISM: Zea mays
<220> FEATURE:
<221> NAME/KEY: promoter
<222> LOCATION: (1)..(2100)
<223> OTHER INFORMATION:

<400> SEQUENCE: 37
ggtcgacctg caggcggccg cgaattcact agtgattagg gcaagcttgg tcgacggccc      60
gggctggtat ctggaaggat ggtgtggacg aagtttgatt tctcctaatt ccgtcactgc     120
catctccaac atagctcctc cagttcttaa atatttgttg tctctgctag ttcatctttg     180
aattaaaaca cggcaaataa aaagaaagg agttgtactg tcttaatttt ggatacctac      240
acatggaaat tggaatcagg tatcaacaca ttctttctgg tgtagagtag agtagttggg     300
tgtgcggtgc ggtgcggccg aatgaataat tggagctctg aatttgatgc gtgactcact     360
ggacacatga caccggctaa catccagccg tgtcaggttc aggctcaggc caggcgtggg     420
tggtacggcc gccgtggcga atactgttac cacgccacgt acggggcacc ggcgcggccc     480
ggggtcttgg aactcatcac cgcgcgcgtg cacagcatcc tcctgtttgg atgcttcgga     540
aaggaaagca gcttagaaga aattaacagc aaataaaaca gtagtcgtag ctagataaaa     600
```

-continued

```
acaagtttgc cgccgaaaac aaacacataa aaaaacgaga aaacagggtg ggagctaggc      660
acgagagtca tttttgggcac gcatgcatta cacacacaca ggcacacaca gcggatgttg    720
ggtggccttg ctgccatgcc tagtagctga ggcctgagga gtgagggacg ccacagtgtg    780
cctcgtcagt cactgccaaa acccggccgg ttctctgcgc acccaccacc aacacgaaca    840
cgatcgtggg cctgccgcgg cttttcatc gccgcgaatg atgggggtgg aggagacgcg     900
gcccaaccgg gccaccgcct cagaaggtgg gtcgcagtcg cagcagcttc cgcctgggcc    960
cctgcatgca ccgtaccggt cagcatgcat gcgatgcgcg ccgccggcgc cccctcccct   1020
gctctcctgc tagacagtca ctcttgacta gcgtcccaag acgcccacgg cgagtcggcg   1080
actgaacaaa acaaaggcac agcgccagca tcaattaccg ggcgacgatg acactgaaac   1140
tgacatgtcg tcccagggcg gagccgacat ggcgacatgt cacacaatcc cctccgcccg   1200
gcgccttact catcggcccc gcccactaga agcggtcgcg ctcagctcag gcagtcaggc   1260
ctcgtattcc ccggagattc tcgggtcact agcgcctcac ccatccatcc acagccgctg   1320
cttctgctgc tgccaccgca tgatcgacag agcatggcct cccactagtg gtagtggatg   1380
tatatgaagt agtagtacag gtacaagtgc ctcgtcagtc agcccacgga ttttggtgca   1440
tttgaagggt taatgtttgt cagaaatttt atctttttta gctgatagag taagataaat   1500
tttaccataa aataaaattt tatgtataga tgaacttagc tgagatgtat attattttt    1560 tcagatattt tcaaaaaaaa aaatagtaga tttacacatg atttgtacca aaaacgtatt   1620
tgcattcgat atgctcccaa taaatatggc ctaaatagca gtagcgtgta gtcgtgtata   1680
acagaaccat cagaccagtg cggcaaacga ttttgcatac atacaccaga caccacagta   1740
gtcaccctca aaccattcac tcagggtaag cactacgaac ctgcaggccg gccacagtaa   1800
gcaatctcaa acattatcca tcctgtacta ctccaaaaaa aaaaaaccga tgcgggcaga   1860
gtcgcctgac acaaacattt taggatcgcg cgtcggccag gaagcaatca acggggaaag   1920
cgcaggggcg aagcctgaca caggcaaaca ccacgaaact gagagtgggt cgaccgtggc   1980
gcgcggacct ggtgctgccg atacacgccg gggacatcga gcgcctctgc agtcgtacaa   2040
gcaggccaac caagcagctc tgcagtcgag agatctggat ccaatcgaat tcccgcggcc   2100
```

<210> SEQ ID NO 38
<211> LENGTH: 841
<212> TYPE: DNA
<213> ORGANISM: Zea mays
<220> FEATURE:
<221> NAME/KEY: promoter
<222> LOCATION: (1)..(841)
<223> OTHER INFORMATION:

<400> SEQUENCE: 38

```
cctcgtattc cccggagatt ctcgggtcac tagcgcctca cccatccatc cacagccgct      60
gcttctgctg ctgccaccgc atgatcgaca gagcatggcc tcccactagt ggtagtggat     120
gtatatgaag tagtagtaca ggtacaagtg cctcgtcagt cagcccacgg attttggtgc    180
atttgaaggg ttaatgtttg tcagaaattt tatcttttt agctgataga gtaagataaa     240
ttttaccata aaataaaatt ttatgtatag atgaacttag ctgagatgta tattattttt    300
ttcagatatt tcaaaaaaa aaaatagtag atttacacat gatttgtacc aaaaacgtat    360
ttgcattcga tatgctccca ataaatatgg cctaaatagc agtagcgtgt agtcgtgtat    420
aacagaacca tcagaccagt gcggcaaacg attttgcata catacaccag acaccacagt    480
agtcaccctc aaaccattca ctcagggtaa gcactacgaa cctgcaggcc ggccacagta    540
```

| | | |
|---|---|---|
| agcaatctca aacattatcc atcctgtact actccaaaaa aaaaaaaccg atgcgggcag | 600 | |
| agtcgcctga cacaaacatt ttaggatcgc gcgtcggcca ggaagcaatc aacggggaaa | 660 | |
| gcgcaggggc gaagcctgac acaggcaaac accacgaaac tgagagtggg tcgaccgtgg | 720 | |
| cgcgcggacc tggtgctgcc gatacacgcc ggggacatcg agcgcctctg cagtcgtaca | 780 | |
| agcaggccaa ccaagcagct ctgcagtcga gagatctgga tccaatcgaa ttcccgcggc | 840 | |
| c | 841 | |

<210> SEQ ID NO 39
<211> LENGTH: 1819
<212> TYPE: DNA
<213> ORGANISM: Zea mays
<220> FEATURE:
<221> NAME/KEY: promoter
<222> LOCATION: (1)..(1819)
<223> OTHER INFORMATION:

<400> SEQUENCE: 39

| | | |
|---|---|---|
| gaattcacta gtgattaggg caagcttggt cgacggcccg ggctggtgag aaaagaaaag | 60 | |
| caagaacacc gtggtattca agttgatcat tggatcactt gagaggagtt gagtgcaact | 120 | |
| ctcgtccgtt gggacgccac aacgtggagt aggcaagttt tgtacttggc cgaaccacgg | 180 | |
| gataaccact gtgtcatctc tgtgattgga ttcttgtggt tattgtgttt tgactcctct | 240 | |
| ctagccactt ggtataaact gtgctaacgc ctaatcaagt tttgtggcta taagtttaag | 300 | |
| ttttttacagg atcacctatt cacccccccc ccctctagg tgctctcaaa ggtccatcac | 360 | |
| tgttgcctga ccgtcggcca tgcactagag tagaaaattg ggccaaaacc atcaggcccc | 420 | |
| cgccgcactc atcttgttca ttgagcggac cactgtaatt gcttctttgt tagataacaa | 480 | |
| tcctattaga ttgtcataag catagggtct cccattataa atttctttta tgttgaaggt | 540 | |
| ccatgttgag gtgcctggtt ctcccatcat cttggaggaa tagtttgtga tgtgttgctt | 600 | |
| ccaatatgca acaatttctt tgatgtgttg gtggagacaa gattggcata attctctgac | 660 | |
| ctgcatttct gtgttagaca gtatcctata ttcttctagg aagtcaagca ttagaatgat | 720 | |
| aaacttgcgg ttgggtacaa aaagtggagg cgccaacctt tgctgcagct ctggtgttct | 780 | |
| ttgaggcagc ttgctaggcg agcaacgaca tcaacaaaat tggttatagt ttgccatgat | 840 | |
| gggagtatgg ccataaggga gtcttggttt ttgagccaag cattttcaaa taggatgact | 900 | |
| atagactttg ggattgtggt gccatggttg caaaaatgga tttatggcca acatggttc | 960 | |
| tgaacgaaga gttaagtgag gcagatggat atgaagagtt gatgtcctca tttgtgaagg | 1020 | |
| cacgatcaag tcttgcaaga gtttgagtgc gacgtttgtt agtccaggca tagagacaat | 1080 | |
| caagtagagg tagctcgaca agtcctagct catggacaat atcattaaac atgttgcaaa | 1140 | |
| gctgatgatt cgtcattatt tttctcatta gcctcccta caagattgaa gtctccaatg | 1200 | |
| aggatccatg gacccacaat gttagagcga atgtctacca agatgttgag gaagttttga | 1260 | |
| gtgcacatgt tactttgagg tggttgccat gcttcgatct ataaatgtat atgcatgttg | 1320 | |
| tgtcatggcg gtatcaactt tttgggttca aaatttgtct cgttttttga aatgtatgca | 1380 | |
| aatcttgttg agttaaacag ggataagatc acaaagtcaa tagaaaatta gagacaaatc | 1440 | |
| cacatgagca aaatgtccat ttgaagatga attacggagt caaatccatt taccacggca | 1500 | |
| gaacgaaaac cgactctagt acgtttaaaa aaaacagga gcaatatcaa ataattttt | 1560 | |
| tttttaaaaa aaagcaaat tcaccgccag ctggcgctga ggcttctagg acatggggca | 1620 | |

-continued

| | |
|---|---|
| caaaacccac tgaactgcct gaacatctcc ctcccaccca tccggccatc cgcctataaa | 1680 |
| aagttgcgag tctcctggct ggcaccaacc actcgcactg gcatagcatc tggtctcgtc | 1740 |
| tctctccgat ccctctcctc tccctccccc tagccactac ccacttgagc gagccctagg | 1800 |
| ccctagcagg cgaagatct | 1819 |

<210> SEQ ID NO 40
<211> LENGTH: 487
<212> TYPE: DNA
<213> ORGANISM: Zea mays
<220> FEATURE:
<221> NAME/KEY: promoter
<222> LOCATION: (1)..(487)
<223> OTHER INFORMATION:

<400> SEQUENCE: 40

| | |
|---|---|
| atcaactttt tgggttcaaa atttgtctcg ttttttgaaa tgtatgcaaa tcttgttgag | 60 |
| ttaaacaggg ataagatcac aaagtcaata gaaaattaga gacaaatcca catgagcaaa | 120 |
| atgtccattt gaagatgaat tacggagtca atccatttta ccacggcaga acgaaaaccg | 180 |
| actctagtac gtttaaaaaa aaacaggagc aatatcaaaa taatttttttt tttaaaaaaa | 240 |
| aagcaaattc accgccagct ggcgctgagg cttctaggac atggggcaca aaacccactg | 300 |
| aactgcctga acatctccct cccacccatc cggccatccg cctataaaaa gttgcgagtc | 360 |
| tcctggctgg caccaaccac tcgcactggc atagcatctg gtctcgtctc tctccgatcc | 420 |
| ctctcctctc cctcccccta gccactaccc acttgagcga gccctaggcc ctagcaggcg | 480 |
| aagatct | 487 |

<210> SEQ ID NO 41
<211> LENGTH: 697
<212> TYPE: DNA
<213> ORGANISM: Zea mays
<220> FEATURE:
<221> NAME/KEY: promoter
<222> LOCATION: (1)..(697)
<223> OTHER INFORMATION:

<400> SEQUENCE: 41

| | |
|---|---|
| cattaaacat gttgcaaagc tgatgattcg tcattatttt tctcattagc ctcccttaca | 60 |
| agattgaagt ctccaatgag gatccatgga cccacaatgt tagagcgaat gtctaccaag | 120 |
| atgttgagga agttttgagt gcacatgtta ctttgaggtg gttgccatgc ttcgatctat | 180 |
| aaatgtatat gcatgttgtg tcatggcggt atcaactttt tgggttcaaa atttgtctcg | 240 |
| ttttttgaaa tgtatgcaaa tcttgttgag ttaaacaggg ataagatcac aaagtcaata | 300 |
| gaaaattaga gacaaatcca catgagcaaa atgtccattt gaagatgaat tacggagtca | 360 |
| atccatttta ccacggcaga acgaaaaccg actctagtac gtttaaaaaa aaacaggagc | 420 |
| aatatcaaaa taatttttttt tttaaaaaaa aagcaaattc accgccagct ggcgctgagg | 480 |
| cttctaggac atggggcaca aaacccactg aactgcctga acatctccct cccacccatc | 540 |
| cggccatccg cctataaaaa gttgcgagtc tcctggctgg caccaaccac tcgcactggc | 600 |
| atagcatctg gtctcgtctc tctccgatcc ctctcctctc cctcccccta gccactaccc | 660 |
| acttgagcga gccctaggcc ctagcaggcg aagatct | 697 |

<210> SEQ ID NO 42
<211> LENGTH: 1010
<212> TYPE: DNA
<213> ORGANISM: Zea mays

```
<220> FEATURE:
<221> NAME/KEY: promoter
<222> LOCATION: (1)..(1010)
<223> OTHER INFORMATION:

<400> SEQUENCE: 42
atcaacaaaa ttggttatag tttgccatga tgggagtatg gccataaggg agtcttggtt      60
tttgagccaa gcattttcaa ataggatgac tatagacttt gggattgtgg tgccatggtt     120
gcaaaaatgg atttatggcc aaacatggtt ctgaacgaag agttaagtga ggcagatgga     180
tatgaagagt tgatgtcctc atttgtgaag gcacgatcaa gtcttgcaag agtttgagtg     240
cgacgtttgt tagtccaggc atagagacaa tcaagtagag gtagctcgac aagtcctagc     300
tcatggacaa tatcattaaa catgttgcaa agctgatgat tcgtcattat ttttctcatt     360
agcctcccctt acaagattga agtctccaat gaggatccat ggacccacaa tgttagagcg     420
aatgtctacc aagatgttga ggaagttttg agtgcacatg ttactttgag gtggttgcca     480
tgcttcgatc tataaatgta tatgcatgtt gtgtcatggc ggtatcaact ttttgggttc     540
aaaatttgtc tcgttttttg aaatgtatgc aaatcttgtt gagttaaaca gggataagat     600
cacaaagtca atagaaaatt agagacaaat ccacatgagc aaaatgtcca tttgaagatg     660
aattacggag tcaaatccat ttaccacggc agaacgaaaa ccgactctag tacgtttaaa     720
aaaaaacagg agcaatatca aaataatttt tttttttaaaa aaaaagcaaa ttcaccgcca     780
gctggcgctg aggcttctag gacatggggc acaaaaccca ctgaactgcc tgaacatctc     840
cctcccaccc atccggccat ccgcctataa aaagttgcga gtctcctggc tggcaccaac     900
cactcgcact ggcatagcat ctggtctcgt ctctctccga tccctctcct ctccctcccc     960
ctagccacta cccacttgag cgagccctag gccctagcag gcgaagatct                1010

<210> SEQ ID NO 43
<211> LENGTH: 593
<212> TYPE: DNA
<213> ORGANISM: Zea mays
<220> FEATURE:
<221> NAME/KEY: promoter
<222> LOCATION: (1)..(593)
<223> OTHER INFORMATION:

<400> SEQUENCE: 43
ggaattcgat tagggcaagc ttggtcgacg gcccgggctg gaataaaatc ttttagcat      60
aaaaaaatga gcagagggag cagttcacta gatatgcatg atctttaaca gctgctgctg     120
gattgtgcgg tttcttttgg cgcaaatggc atgaacagag taatccggga cgcgccatca     180
gtgtgggtgt gtcatccgtg ggagacgcgg gtgcggcgca tgagcctggg atacaggggc     240
cagtgtgagg agcagctacc agaccagggc acctagttat ttttttctcag atgtcaagct     300
aataactgaa caagttcatg agcaaggacc ctgcaccgac caccaaagtt caacgattca     360
cacgctttgg aactagaaca actgctgttg gaaacctcct ggtgaaatct caccctatta     420
ataccatgct gatgagccaa tagcagaagc atcacacact aatcaacaag caggaccagc     480
tagctagctc ctcccactgc tatcacccgg gccccggcca gccatcttgc tgaaagagaa     540
aagcgagatc tggatccaat cactagtgaa ttcgcggccg cctgcaggtc gac            593

<210> SEQ ID NO 44
<211> LENGTH: 717
<212> TYPE: DNA
<213> ORGANISM: Zea mays
<220> FEATURE:
```

<221> NAME/KEY: promoter
<222> LOCATION: (1)..(717)
<223> OTHER INFORMATION:

<400> SEQUENCE: 44

| | | |
|---|---|---|
| gaattcacta gtgattaggg caagcttggt cgacggcccg ggctggtaaa gcaccagttt | 60 |
| taatggtcgt cctatactcc tatgtcacac accaagcaaa catctgttac catctcctcg | 120 |
| cttctcgtct atccgtaaac cgttcactca catatatgtc tgtttctctt caccatttct | 180 |
| catttaccag ttggtcgtta tcccacagat ggcctatgag aattcatcca atcccaacac | 240 |
| gacaggaaga cgcacgtagc gtagcgtttc cacgtagtaa caccccgtta actaacagag | 300 |
| aacgagagag ctgtaaaaaa agtcagactt tttttaattc atacatttct cagtctttta | 360 |
| gctaaaacaa agtgtaatat ttattcttat cagtttaata tatctattat gtatattata | 420 |
| tattcacttt gatattaaat ttattttttg tggctatttt ttgtgggagg ttccactaca | 480 |
| ctgtcgtgac gagagattgt tgtttttgtg tgtgtccaca gtccacacag accgacgatc | 540 |
| tcttcctgtt ggcggcctat ataaagatgg ccatggaaga atgccataag gccattaaga | 600 |
| attctctcgg tctctaccaa aaaaacagcg acctctaacg cttagctagc tctttgtgtc | 660 |
| agcgcctgag catcgagcta ttggagatct ggatccaatc gaattcccgc ggccgcc | 717 |

<210> SEQ ID NO 45
<211> LENGTH: 1572
<212> TYPE: DNA
<213> ORGANISM: Zea mays
<220> FEATURE:
<221> NAME/KEY: promoter
<222> LOCATION: (1)..(1572)
<223> OTHER INFORMATION:

<400> SEQUENCE: 45

| | | |
|---|---|---|
| aagctatgca tccaacgcgt tgggagctct cccatatggt cgacctgcag gcggccgcga | 60 |
| attcactagt gattagggca agcttggtcg acggcccggg ctggtaaacg tgaccggctt | 120 |
| aaacgacaga ttctgtcatt caacagtcta cttgaatcaa tttgaccaac tccagaatcc | 180 |
| ttctcatttt gctctccatc cccattttat gtgctctagg atactgttca gccgttacta | 240 |
| tcatgcaacg caaaatggag gcctccatt gcactctctt tttctccgag ttccctctct | 300 |
| ttcgtgcaaa tcaactatcg cgttcacggt tcatctatgc ctcatccttg attaattaaa | 360 |
| ggttcatgat ggagatactg tccaccattt agtagtccta ccgtgcaaaa tggaggcctt | 420 |
| ttattttact ctcttctccg ttctctcttt ctgggcaacc gtcttttgat tggttgaagg | 480 |
| ttcacggtgg catgtaaggt gatacacgcc cattctacgc gtcactgtgc atacggagga | 540 |
| atggggactt ggtctaaagg gtccggaaac agctctgccg cgcatgcgtc ttccagaaaa | 600 |
| aataaaatac atgcatgtgt cgtgatgcat cactgcatgg cttcttcatg ccaatagtgt | 660 |
| gtaaccccag aaacgacact cgcggcatgc caatcgcgtt tgcatgattg gtgttcgctt | 720 |
| cgtgttttgc ctgtatcccc tcgtagacag ccaactgtcg gtttaatttg aactcgctct | 780 |
| tgctaaaacg atcgacgccg agttcttaag ccagttttta gcaacataaa agatagtcaa | 840 |
| agccttttgt catgcacatc tagctcggct cttaatgttg gccaggctg ccgggctgag | 900 |
| tggaatagta tgtctggact ctggcccggt ctagctcgaa ctagcccaac caccccaaaa | 960 |
| actagcaagc gatttgttac attgtgcaaa taaaataaaa ttaagaaaga ttgacgttgc | 1020 |
| ataatgagac tacagatcaa taataattcc caaatcaggg tttcgatatc tcacacgaga | 1080 |
| cacatgattt tgattggacg acgtatacaa ctagtattat gcaacgagac tttaaccgta | 1140 |

| | | | | |
|---|---|---|---|---|
| tacaagctag | attgtagatt | ggtttattta | gattataatc | tgctcaaatc atctaatcta | 1200 |
| acttcacaaa | caaacataca | gcctctatcg | caacaataac | cgagattaag ggagatgtga | 1260 |
| tgtgtccatc | catgcatcca | tccggttcca | tcaggataag | actacacgcg ccgccgccca | 1320 |
| cgcgatcagg | gactcgcggt | tcgtggcggc | cctggccaga | gtctgcgccc gctcctgccc | 1380 |
| ccgcccggg | ccaggccacc | ctcgcctcct | cgcgcctata | aagtgcgggc atacggcgta | 1440 |
| cccgattgcc | ccaagccgca | accgcaaccg | caaccaccctt | cccaaatctc agtagtcgcc | 1500 |
| tctcgtcgtc | ttcgtctagc | ccggcccgtt | ccaaaacctc | cgtagccgcc gacgccaccc | 1560 |
| cggcgaagat | ct | | | | 1572 |

<210> SEQ ID NO 46
<211> LENGTH: 1150
<212> TYPE: DNA
<213> ORGANISM: Zea mays
<220> FEATURE:
<221> NAME/KEY: promoter
<222> LOCATION: (1)..(1150)
<223> OTHER INFORMATION:

<400> SEQUENCE: 46

| | | | | |
|---|---|---|---|---|
| ttttactctc | ttctccggtt | ctctcttctg | ggcaaccgtc | ttttgattgg ttgaaggttc | 60 |
| acggtggcat | gtaaggtgat | acacgcccat | tctacgcgtc | actgtgcata cggaggaatg | 120 |
| gggacttggt | ctaaagggtc | cggaaacagc | tctgccgcgc | atgcgtcttc cagaaaaaat | 180 |
| aaaatacatg | catgtgtcgt | gatgcatcac | tgcatggctt | cttcatgcca atagtgtgta | 240 |
| accccagaaa | cgacactcgc | ggcatgccaa | tcgcgtttgc | atgattggtg ttcgcttcgt | 300 |
| gttttgcctg | tatcccctcg | tagacagcca | actgtcggtt | taatttgaac tcgctcttgc | 360 |
| taaaacgatc | gacgccgagt | tcttaagcca | gttttagca | acataaaaga tagtcaaagc | 420 |
| cttttgtcat | gcacatctag | ctcggctctt | aatgttgggc | caggctgccg ggctgagtgg | 480 |
| aatagtatgt | ctggactctg | gcccggtcta | gctcgaacta | gcccaaccac cccaaaaact | 540 |
| agcaagcgat | ttgttacatt | gtgcaaataa | aataaaatta | agaaagattg acgttgcata | 600 |
| atgagactac | agatcaataa | taattcccaa | atcagggttt | cgatatctca cacgagacac | 660 |
| atgattttga | ttggacgacg | tatacaacta | gtattatgca | acgagactt aaccgtatac | 720 |
| aagctagatt | gtagattggt | ttatttagat | tataatctgc | tcaaatcatc taatctaact | 780 |
| tcacaaacaa | acatacagcc | tctatcgcaa | caataaccga | gattaaggga gatgtgatgt | 840 |
| gtccatccat | gcatccatcc | ggttccatca | ggataagact | acacgcgccg ccgcccacgc | 900 |
| gatcagggac | tcgcggttcg | tggcggccct | ggccagagtc | tgcgcccgct cctgcccccg | 960 |
| ccccgggcca | ggccacccctc | gcctcctcgc | gcctataaag | tgcgggcata cggcgtaccc | 1020 |
| gattgcccca | agccgcaacc | gcaaccgcaa | ccaccttccc | aaatctcagt agtcgcctct | 1080 |
| cgtcgtcttc | gtctagcccg | gcccgttcca | aaacctccgt | agccgccgac gccaccccgg | 1140 |
| cgaagatctc | | | | | 1150 |

<210> SEQ ID NO 47
<211> LENGTH: 866
<212> TYPE: DNA
<213> ORGANISM: Zea mays
<220> FEATURE:
<221> NAME/KEY: promoter
<222> LOCATION: (1)..(866)
<223> OTHER INFORMATION:

```
<400> SEQUENCE: 47
attggtgttc gcttcgtgtt ttgcctgtat cccctcgtag acagccaact gtcggtttaa      60
tttgaactcg ctcttgctaa aacgatcgac gccgagttct taagccagtt tttagcaaca     120
taaaagatag tcaaagcctt ttgtcatgca catctagctc ggctcttaat gttgggccag     180
gctgccgggc tgagtggaat agtatgtctg gactctggcc cggtctagct cgaactagcc     240
caaccacccc aaaaactagc aagcgatttg ttacattgtg caaataaaat aaaattaaga     300
aagattgacg ttgcataatg agactacaga tcaataataa ttcccaaatc agggtttcga     360
tatctcacac gagacacatg attttgattg gacgacgtat acaactagta ttatgcaacg     420
agactttaac cgtatacaag ctagattgta gattggttta tttagattat aatctgctca     480
aatcatctaa tctaacttca caaacaaaca tacagcctct atcgcaacaa taaccgagat     540
taagggagat gtgatgtgtc catccatgca tccatccggt tccatcagga taagactaca     600
cgcgccgccg cccacgcgat cagggactcg cggttcgtgg cggccctggc cagagtctgc     660
gcccgctcct gccccgccc cgggccaggc caccctcgcc tcctcgcgcc tataaagtgc      720
gggcatacgg cgtacccgat tgccccaagc cgcaaccgca accgcaacca ccttcccaaa     780
tctcagtagt cgcctctcgt cgtcttcgtc tagcccggcc cgttccaaaa cctccgtagc     840
cgccgacgcc accccggcga agatct                                          866
```

```
<210> SEQ ID NO 48
<211> LENGTH: 1500
<212> TYPE: DNA
<213> ORGANISM: Zea mays
<220> FEATURE:
<221> NAME/KEY: misc_feature
<222> LOCATION: (609)..(992)
<223> OTHER INFORMATION: a or g or c or t
<220> FEATURE:
<221> NAME/KEY: misc_feature
<222> LOCATION: (455)..(455)
<223> OTHER INFORMATION: a or g or c or t
<220> FEATURE:
<221> NAME/KEY: misc_feature
<222> LOCATION: (570)..(570)
<223> OTHER INFORMATION: a or g or c or t
<220> FEATURE:
<221> NAME/KEY: misc_feature
<222> LOCATION: (574)..(574)
<223> OTHER INFORMATION: a or g or c or t

<400> SEQUENCE: 48
tagggcaagc ttggtcgacg gcccggggct ggtacctctt cttttctctt ctctttccct      60
tcttgtcgtc gcccctgtca ctatcactag acaaaggaca tttagcgata aaatgaccgg     120
gcttaccaca tttgtagcaa accttcttgg agcggggttt gaaatccttc cccctccttt     180
gcttgaggat ttggcggaag ctcttgatga tgagcgccat ttcctcattg tcgagcttgg     240
aggcgtcgat gggaatacta cttggtgtag aatccttctt ttcttcttcc gttgccttga     300
atgcgacggg ttacacctca ggtgttgagg tggcgccttg ctcgatgatt ttcttggagc     360
ctttgatcat caattcaaag ctcacaaatt ttcctatcac ttcctcggga gacattagtt     420
tataccttgg atcaccacga attaattgaa cttgngtagg ggttatgaaa aacgaagtga     480
tctaagaata accttgacca tctcatgggc atcccattgg tgctccgagg ttgccacttg     540
gttcaccaag gtcttgaccg gtggacatgn ttgngctcct cccttgggaa catgaacgac     600
cgactccctn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
```

```
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnccaaccaa gatagaatta gtcataatcg   1020
ggcaagacat tcaaaaattt tgagcttcaa ttttgaaact atccaatcta tctttcattc   1080
tatctgctat tttaaacttc attatataaa caaagcaatt tttaatataa aataatattt   1140
ttgatggccg ctsgacatgg ctttgagaag ccattgatcg ttcttttttct gagacgataa  1200 aaatgcctca aatcttataa atatcgagga aaacaaatgc tatgcagcgt tctacctatg   1260
aaaacgatga caaacactgc aagacagtgt attccaagcg cgaatctcga tcggtaacga   1320
aaggtccctg ttccgtggac cgtcaggtat gccacccaat agtatcccgc catgtcagcc   1380
tggccacgtc ctaaatcagc atgtcaggta taagagggaa ccttgcataa aaccccctcac 1440 gttatcgcgc acatctcctg atcctcgttc ctctccgccc cgcttgcaga tctggatcca  1500
```

```
<210> SEQ ID NO 49
<211> LENGTH: 508
<212> TYPE: DNA
<213> ORGANISM: Zea mays
<220> FEATURE:
<221> NAME/KEY: promoter
<222> LOCATION: (1)..(508)
<223> OTHER INFORMATION:

<400> SEQUENCE: 49
ccaaccaaga tagaattagt cataatcggg caagacattc aaaaattttg agcttcaatt    60
ttgaaactat ccaatctatc tttcattcta tctgctattt taaacttcat tatataaaca   120 aagcaattt taatataaaa taatattttt gatggccgct sgacatggct ttgagaagcc    180
attgatcgtt cttttttctga gacgataaaa atgcctcaaa tcttataaat atcgaggaaa   240
acaaatgcta tgcagcgttc tacctatgaa acgatgaca aacactgcaa gacagtgtat    300
tccaagcgcg aatctcgatc ggtaacgaaa ggtccctgtt ccgtggaccg tcaggtatgc   360
cacccaatag tatcccgcca tgtcagcctg gccacgtcct aaatcagcat gtcaggtata   420
agagggaacc ttgcataaaa ccccctcacgt tatcgcgcac atctcctgat cctcgttcct  480 ctccgcccccg cttgcagatc tggatcca                                     508
```

```
<210> SEQ ID NO 50
<211> LENGTH: 1328
<212> TYPE: DNA
<213> ORGANISM: Zea mays
<220> FEATURE:
<221> NAME/KEY: promoter
<222> LOCATION: (1)..(1328)
<223> OTHER INFORMATION:

<400> SEQUENCE: 50
atcccccggg tccactaaaa gagtaaagga cctcacgaaa ggcccaaggg cccaataaat    60
cgtaaggtca ttctttcgtg ggcctgggga gaaacaaccg gcaaagcaga acgacatgag   120
gctggattgg tgcaaacccg gacggcccac agcgtcgagc gaatggctgc aacagagatc   180
cgactttccc gcgctggagt ctccatgcaa cgaagccatg cgaggataag tcggcaaggg   240
ttacgtaggg ataatctcaa gaggttcact atcttttagc tacttgttgt tatcttaccc   300
```

```
acgtgtactg ccccacggtc gagtatataa ggcctagggg gcacccctc agaacgatcg      360 accctatccg acttagccac ccacgtaaac tctctgtgcc ttcaacccag agagccctct     420
tgtaaccaca gccgaattct catcaggacg tagggtgtta cgcatctcta agcggcccga     480
acctgtaaat cttgttcact gtctctcgtg cgatcggcac gaaccatttt gctacagtcg     540
tggacaccgt cctactccta gaaaacacct tgagggcaa ccccgggtgt gcggtcggac      600
ccaaaacacc gacatactca actctagttc gaattagagt taaagtcatg ccaaagagag     660
tgactaacct atactagcag cttcaatgag ccagttatct agcccaagca aattgcatgg     720
gagaaaagca aactgtgcaa atcagccggc cttggcatgc cagccattat tcggactgat     780
aggatgcttc ggttttttt ttgtgaaaat attttgttgg aaactagaga tatatcgcta      840
accaggtagg agcatgagca tgtaaaatat aaaatagcta gacaatatag gccatgtttg     900
ttttagactt tttagctttt gcccatcaaa aactgctgta tactataaaa cacttagctt     960
ttcagactgc ttctataata atcgatttgg taaactatct aaaatcaata tgaatataaa    1020
atcgatcgag tcgttataat aataaaaaat tgtcactttc tagatcctga actcatagat    1080
acatttattt tgatccctac gacatttaga ttttctccac aatcagatta agattatgat    1140
cagttgctac tttcaaaaag ctgaaccata cggatccact tagccttata ctgacaggat    1200
gattcgctgg aatgttctag aaagaagggt cgctttggtt gcgtacagta ccctctagaa    1260
gcctccgggt cgctcggtgt gggttgctaa ctactcgcag cagccagagg ccagatccag    1320
ccgccaac                                                             1328
```

<210> SEQ ID NO 51
<211> LENGTH: 996
<212> TYPE: DNA
<213> ORGANISM: Zea mays
<220> FEATURE:
<221> NAME/KEY: promoter
<222> LOCATION: (1)..(996)
<223> OTHER INFORMATION:

<400> SEQUENCE: 51

```
cctagggggc acccctcag aacgatcgac cctatccgac ttagccaccc acgtaaactc      60
tctgtgcctt caacccagag agccctcttg taaccacagc cgaattctca tcaggacgta    120
gggtgttacg catctctaag cggcccgaac ctgtaaatct tgttcactgt ctctcgtgcg    180
atcggcacga accattttgc tacagtcgtg gacaccgtcc tactcctaga aaacaccttg    240
aggggcaacc ccgggtgtgc ggtcggaccc aaaacaccga catactcaac tctagttcga    300
attagagtta aagtcatgcc aaagagagtg actaacctat actagcagct tcaatgagcc    360
agttatctag cccaagcaaa ttgcatggga gaaaagcaaa ctgtgcaaat cagccggcct    420
tggcatgcca gccattattc ggactgatag gatgcttcgg ttttttttt gtgaaaatat     480 tttgttggaa actagagata tatcgctaac caggtaggag catgagcatg taaaatataa    540
aatagctaga caatataggc catgtttgtt ttagactttt tagcttttgc ccatcaaaaa    600
ctgctgtata ctataaaaca cttagctttt cagactgctt ctataataat cgatttggta    660
aactatctaa atcaatatg aatataaaat cgatcgagtc gttataataa taaaaaattg     720
tcactttcta gatcctgaac tcatagatac atttattttg atccctacga catttagatt    780
ttctccacaa tcagattaag attatgatca gttgctactt tcaaaaagct gaaccatacg    840
gatccactta gccttatact gacaggatga ttcgctggaa tgttctagaa agaagggtcg    900
ctttggttgc gtacagtacc ctctagaagc ctccgggtcg ctcggtgtgg gttgctaact    960
```

```
actcgcagca gccagaggcc agatccagcc gccaac                                996
```

```
<210> SEQ ID NO 52
<211> LENGTH: 1821
<212> TYPE: DNA
<213> ORGANISM: Zea mays
<220> FEATURE:
<221> NAME/KEY: promoter
<222> LOCATION: (1)..(1821)
<223> OTHER INFORMATION:

<400> SEQUENCE: 52
cctgcctctc tgcgactgat ctccggcggc gaggcgccgc accggggtat gggccaggat      60
gtggtcgcgc acgtctacga cgtcgccacc gccggctccg acaccaccgt gctccacatc     120
aaccgcttct ttaaggacgc catcggcctc ggcggcatct tccacaccgc catccaggtc     180
atccgtttct ccaaatccca ccaccatttt ttgaatgcct gcaacgcccg caaagattgg     240
atctcgacgc cagcggttta gtgttcgaga gaatcgtttc ttttatatat agtggcgttg     300
gttaatgcgt ccaatcagtt tttaaccccc aaatcttaat tcaatgctgt tgctactgaa     360
tgaatggggg cgattatctt tttattgctc ctgtgaataa tctaacttga tctttccttg     420
ggattgacaa actgtgcttc tgatacgtgt atgtaactgc tagccatagt taccatttag     480
cctgataccg tgccctgga agagggtgtg acttcaaagt tcaaactgta attctcaatg      540
ggagcttgga gatttcctat gaggccacta gggttgaatg cagccttgtg gtaaaagaga     600
tccctgtatc gtcctaagga tgatgccacg gattgtgaaa gaaaaaaatt ctttattctt     660
tatagccatt ctgctccttg ttctgcgaac tgcttgttag gctgctttac tgctctagaa     720
tgggcactga ttattaggct cgtttactgc tctctttaac gaaaaatgtg tagattcatc     780
ccacaaaact agtcctttat ggtatcaatg agcttatttg tgattggatt cctagcaact     840
ggctaatcat tagtaggtgc ttatagttga ggctctgttg tgatcaactc ctgagcatct     900
cggctaacag gtctacggtg atgaagaatg gtcctttggc tactgtgaac gtggcactgg     960
ggtttttagc tgtcccccat gcaaaaatcc catgtacact tatcgcgagt ccatagtgct    1020
ggggaagacc aactgctgta tcctcaaggt aaatcagata ctaagggagc tgagctggga    1080
gtggcctgga cattcatatg aactcctgtc aagaaactgc aatcacttct gcaatacctt    1140
ctgcgaaaag cttgaagtat cgaagcttcc aggttcttat gatttcttac catttgacta    1200
aacaaattat ttcctcgttc cttatctgta atggctactg aaactaaacc ctttatttg     1260
aactgaaggc caatcatgaa acttattcaa aattaaactg ttttatgact ccaaagtgat    1320
tggttatatg caggttgggt caatcgcttt gcaaatgcgg gtgacgctgc tctagaggtc    1380
actgaaacca cagcaggaaa ggtatgcatt ctgaactttt ctgctagttt tgcgttttc     1440
tcttttattt ttgtcatctc ctgttgtagc attggaattt taagtatttc cccttaagtt    1500
atgtgtatct tctagacttt tgtgttcagc atcacactct ttgcaaactc gatagcaagt    1560
ggaccatgcc atcttgttaa ccatctgaaa cagaatgaag aagacccaga aactaacctt    1620
ctttatagca ctgtcagtgt cagattgtgt tggaaatata tatttcttag aaatctttat    1680
gcaaaggaat ttatgccatt atgtgaaaca gtagcgatag cctttatccat cggcaatact   1740
gtccaaacta aattagtttg taaaattggc acatatttga ttccatcatt cttttttgctc   1800
tgcactcagc tgaaacaagc g                                              1821

<210> SEQ ID NO 53
```

```
<211> LENGTH: 1028
<212> TYPE: DNA
<213> ORGANISM: Zea mays
<220> FEATURE:
<221> NAME/KEY: promoter
<222> LOCATION: (1)..(1028)
<223> OTHER INFORMATION:

<400> SEQUENCE: 53
cctttatggt atcaatgagc ttatttgtga ttggattcct agcaactggc taatcattag      60
taggtgctta tagttgaggc tctgttgtga tcaactcctg agcatctcgg ctaacaggtc     120
tacggtgatg aagaatggtc ctttggctac tgtgaacgtg gcactggggt ttttagctgt     180
cccccatgca aaaatcccat gtacacttat cgcgagtcca tagtgctggg aagaccaac     240 tgctgtatcc tcaaggtaaa tcagatacta agggagctga gctgggagtg gcctggacat     300
tcatatgaac tcctgtcaag aaactgcaat cacttctgca ataccttctg cgaaaagctt     360
gaagtatcga agcttccagg ttcttatgat ttcttaccat ttgactaaac aaattatttc     420
ctcgttcctt atctgtaatg gctactgaaa ctaaacccct tattttgaac tgaaggccaa     480
tcatgaaact tattcaaaat taaactgttt tatgactcca aagtgattgg ttatatgcag     540
gttgggtcaa tcgctttgca aatgcgggtg acgctgctct agaggtcact gaaaccacag     600
caggaaaggt atgcattctg aacttttctg ctagttttgc gttttctct tttattttg      660 tcatctcctg ttgtagcatt ggaattttaa gtatttcccc ttaagttatg tgtatcttct     720 agactttgt gttcagcatc acactctttg caaactcgat agcaagtgga ccatgccatc     780
ttgttaacca tctgaaacag aatgaagaag acccagaaac taaccttctt tatagcactg     840
tcagtgtcag attgtgttgg aaatatatat ttcttagaaa tctttatgca aaggaattta     900
tgccattatg tgaaacagta gcgatagcct tatccatcgg caatactgtc caaactaaat     960
tagtttgtaa aattggcaca tatttgattc catcattctt tttgctctgc actcagctga    1020
aacaagcg                                                             1028

<210> SEQ ID NO 54
<211> LENGTH: 1876
<212> TYPE: DNA
<213> ORGANISM: Zea mays
<220> FEATURE:
<221> NAME/KEY: promoter
<222> LOCATION: (1)..(1876)
<223> OTHER INFORMATION:

<400> SEQUENCE: 54
ctgtctgtgg ccgagatcac caacagcgcc ttcgagccat cctccatgat ggccaagtgc      60
gatccccgcc atggtaagta catggcctgc tgcctcatgt accgtggtga tgtggtcccc     120
aaggatgtga atgctgctgt ggccaccatc aagaccaagc gcaccatcca gtttgtggac     180
tggtgcccaa ctggctttaa gtgcggcatt aactaccagc tccaagtgt ggtgcctggt      240 ggtgacctgg ccaaggtgca gcgcgctgtg tgcatgatct ccaactccac cagtgttgtg     300
gaggtgttct cccgcatcga ccacaagttc gacctcatgt acgccaagcg tgccttcgtg     360
cactggtatg tcggtgaggg tatggaggag ggcgagttct ctgaggcccg tgaggatctg     420
gcagcgctcg agaaggacta cgaggaggtt ggtgctgagt tgatgaggg tgaggaaggt      480 gatgatggtg atgagtacta gaagtatcct gatgcggtca tcgtcaggct tgtgtgctgc     540
tcttgtcccc gttgtggttt gcaacacctg atgttgtaag actttctggt tatgtccgcc     600
ccgctgtgcc actgggttat taagaacgtc gttatggatg gttgtctaca ctacattatt     660
```

```
gcttctcgat attggaaaac tgttatgcgc ctcggtggat tgtgttgttg tcgtaatgtc      720
atcactcata cgccgctggg aattttgagg cctgtcaagc atcaggattg cgttatgagt      780
taaatgcttc agcgacgttt aaacttgtct aaggtgccat ctagatcatg aacttgtcaa      840
gggttgccac ttagatcatg aacttcgtaa atatgttttt ggatccaaaa tatgtttttg      900
atccttaagg gtgtgtttgg ttgaatgtat aagaagggat gaaagaggaa tgtcataatt      960
tctatagtgt ttggttgaga gacaagtgag gacgagataa atacctaaga agggatgaaa     1020
gaggaatgcc acaatttcta tagtgtttgg ttcagagaca agtgacaatt tctatagtgt     1080
ttggttgaga gacaagtgag ggcgagtaaa taccgcaata attttttggt ggcaccgaat     1140
ttttgtgaag ttgtatacat tttggacacc aatagaaaat agaattaaaa aaatataaaa     1200
ctggtgtcat ttaaatcagt gtcacgttat taaaatttaa aactatcaac taaaattgtc     1260
taatggatta tttatgtggt tttgtaaagt tgtggagatt aaacaaccag ttttgaagat     1320
aagtaagtga aatagtcaaa tataaaacta ggttaagaat ttaggtacac ttacgactag     1380
tttagatgcc gcaaaatggg ttaaattttt cttcttattc aaaattaaat aataaggtga     1440
atttaactac tctaatttcc tctgtttttt taactcccaa actatccctt attcgtaata     1500
ataggaagcg gtgacagttt ggtggtgaga actcaggtat caacaaaaag aaatgtattt     1560
ttgaaatatt ttgctcgtaa tgccctgcaa ggtttcgatt ccgtagcca gtacatgtcc      1620 gctcttgacc caggtactgt gtcacgaacc aaccgaccgt tgaacggacg tggagcacga     1680
accattaaaa caatcaaaat ctcaggggct caaacgaaaa acaccgccc cttccctcg       1740 cttgcgctgg cactccatcg tgggctcgtg gcccaggctg tcgttctgtt ctataaagcg     1800
agacgagtgg gagcaggcgt aaccctaatt gagcatcgca gagataggcg tcttcgtact     1860
cgcctacctc cgcggc                                                     1876

<210> SEQ ID NO 55
<211> LENGTH: 1126
<212> TYPE: DNA
<213> ORGANISM: Zea mays
<220> FEATURE:
<221> NAME/KEY: promoter
<222> LOCATION: (1)..(1126)
<223> OTHER INFORMATION:

<400> SEQUENCE: 55
cctgtcaagc atcaggattg cgttatgagt taaatgcttc agcgacgttt aaacttgtct       60
aaggtgccat ctagatcatg aacttgtcaa gggttgccac ttagatcatg aacttcgtaa      120
atatgttttt ggatccaaaa tatgtttttg atccttaagg gtgtgtttgg ttgaatgtat      180
aagaagggat gaaagaggaa tgtcataatt tctatagtgt ttggttgaga gacaagtgag      240
gacgagataa atacctaaga agggatgaaa gaggaatgcc acaatttcta tagtgtttgg      300
ttcagagaca agtgacaatt tctatagtgt ttggttgaga gacaagtgag ggcgagtaaa      360
taccgcaata attttttggt ggcaccgaat ttttgtgaag ttgtatacat tttggacacc      420
aatagaaaat agaattaaaa aaatataaaa ctggtgtcat ttaaatcagt gtcacgttat      480
taaaatttaa aactatcaac taaaattgtc taatggatta tttatgtggt tttgtaaagt      540
tgtggagatt aaacaaccag ttttgaagat aagtaagtga aatagtcaaa tataaaacta      600
ggttaagaat ttaggtacac ttacgactag tttagatgcc gcaaaatggg ttaaattttt      660
cttcttattc aaaattaaat aataaggtga atttaactac tctaatttcc tctgtttttt      720
```

```
taactcccaa actatccctt attcgtaata ataggaagcg gtgacagttt ggtggtgaga    780
actcaggtat caacaaaaag aaatgtattt ttgaaatatt ttgctcgtaa tgccctgcaa    840
ggtttcgatt tccgtagcca gtacatgtcc gctcttgacc caggtactgt gtcacgaacc    900
aaccgaccgt tgaacggacg tggagcacga accattaaaa caatcaaaat ctcagggct    960 caaacgaaaa acaccgcccc cttccctcg cttgcgctgg cactccatcg tgggctcgtg    1020
gcccaggctg tcgttctgtt ctataaagcg agacgagtgg gagcaggcgt aaccctaatt    1080
gagcatcgca gagataggcg tcttcgtact cgcctacctc cgcggc                   1126
```

<210> SEQ ID NO 56
<211> LENGTH: 776
<212> TYPE: DNA
<213> ORGANISM: Triticum aestivum
<220> FEATURE:
<221> NAME/KEY: promoter
<222> LOCATION: (1)..(776)
<223> OTHER INFORMATION:

<400> SEQUENCE: 56

```
aactccaccc tcactctctt tcatccccat cgtgtacgcc gatggatcct tctatagtgg     60
ctgcgcctcc taagcctatt acctagctat cttttcttgtc aagctcttct ctgatacctc   120
cgcaagaaag aagagatctg atttatacct ttttcaacat cataggaaaa aagaatgaat   180
ataaatttcc gtatgactat ctctgcagag agattataat gcggaatgcg gggcaatgtt   240
tatgtttctt cttttcataa catttattct cttgggtgcc taaggtcatg tccaatgcaa    300
gaacacttat atagacacct aaagaaagag aacaatgtaa gtttcacaag ctttaataca    360
aaatattatt ttagaggagc ctagacacct aaaaagcact aagaatttac ttaaacgttg   420
aacctcgaat taagaaacaa tatcatgatt tgcattgagc aatcatgctt tggatgggaa    480
taactctcgt acaagctaaa cggtctaaac gtaaaaaacg agggaccaag tcaagaatag    540
ccttgcttgt cgagtggtcg accccccatg gccaagaggt gcgcatggcc tcaaaccgag    600
tgctaatttc ttttcaacct attttttccct ctaccttccc ttgtttctcg ctcctcccca   660
tgacattcct ctcgcgcaaa ccttctccct cccccctgca gctagcatct ctctccttct    720
cctctctccc ctccaagctc catttccggt ttcccacgtt gtgtaggggg ctttga         776
```

<210> SEQ ID NO 57
<211> LENGTH: 517
<212> TYPE: DNA
<213> ORGANISM: Triticum aestivum
<220> FEATURE:
<221> NAME/KEY: promoter
<222> LOCATION: (1)..(517)
<223> OTHER INFORMATION:

<400> SEQUENCE: 57

```
aaaattcagg aactctttc aaattcacaa actttttttt ggcatcgtga acttttttca     60
aattgatgga agtcttaaaa atttcctaac attttgagaa ccaacgtttt cttctatttg   120
ttcaactatt tcaaaatcaa aggaggcgag agatggtttt ctcccttgcc gagcagacag    180
gaagagccga ggtgaagtgt acgaggcgat gaaaaaacta acaaatggat gcctgtcatc   240
aggcgctagc tttccatttc aggcgccggt taggagcccc ccagatttgg atcactgttc   300
aaagaaaaac agatttggac catgcatttg gtgtgagggt gattgaaact tggaaggaac    360
gacagttagg caacatgcca tgctcatgat cgagtagaac tcttcgccaa agtactatat    420
atagagagaa gagcgacgcg gacaatactc ctatatcaac acacaacgaa ggcaacaact    480
```

```
gtagtacgta ggtacgtaag tgtagctagc ctcctcc                              517

<210> SEQ ID NO 58
<211> LENGTH: 1290
<212> TYPE: DNA
<213> ORGANISM: Zea mays
<220> FEATURE:
<221> NAME/KEY: promoter
<222> LOCATION: (1)..(1290)
<223> OTHER INFORMATION:

<400> SEQUENCE: 58
aaagaagagt cttacatgca atttcttttg tttgaataat gttttaact taaatttatt       60 tttttgcatg cgcgacattt attcttcgta atattttttc catgatctaa cttgtgagtc     120 atttcataa atcaacgtca agtatgaatc catgtttctt acttggaaac tctgaacaaa      180
cattactagc aggaggcgct cgcgttggcg tcactcatcg acgacgagaa aaagcttggt     240
aactgacaat tcgacctcta aaagcagtcc tacgtggccg cttgcgcacc tgtggacgaa     300
aagttctggc gctgtcgccg cttggacgtg gtccaaagcg gctgtaccac tctgttcatc     360
gtcaagcagg ggtatctcat gttcgtcggc aactccgacg actctcgggt tgttctgggc     420
accacattca cgacggcgc catcacgccg tccagctcat cgtccacatg aagcccaacc      480
agccacttaa gtcgctattg accggccatg aattcttgtg cactgggtga cgggcgttgc     540
tgatgttgtg tgagtacttc aaacatgatg tatgcggagg agtagcgcat acggtggtgc     600
aacgtccagt tgtactacct cgctgataag ccaggggtgc acttcgtctg gcagcccgac    660
caagaatcgt cgtgactcgt catgtcacgc gcgttcgacg attactatat aaaggattat     720
ggtgtcatct cggcgccgga ggtgacgcgg aggaggaccg acagcaatga ccagttcgcc    780
attctcgcca ccatcagggt agttttgtg tctgcctacg tttaattctc ttcgcaaaca     840
tacacacttg tcttttgtt taagcaagtg catatggtgg tgcgtgcctg ataactgatg     900
acatacgaga gaacttcttc cggtaggtgt aggacgtgct ctccattgac gagaccatac    960
aaattatagt atatattgaa gactgcatga tagtgatggt tacaatatag tgatgaaaca    1020
gctagattaa ataataaaa atttatatat acgtagaatt ataaatagat tataattttt    1080
ttatcgtatc agtataatac atatttata tataaattat catatgtttc cgtccgtcgc    1140
tcaccgggac acaccgtgat ggaagcatgg agcacccacg catggatcaa aatcctcccc    1200
caaaacgcga cgaaattctc cgcgagcaaa atataaagtt tataaaccca ctcctcccct    1260 tccctgttc cctctaccac caccaccggc                                      1290

<210> SEQ ID NO 59
<211> LENGTH: 2126
<212> TYPE: DNA
<213> ORGANISM: Zea mays
<220> FEATURE:
<221> NAME/KEY: promoter
<222> LOCATION: (1)..(2126)
<223> OTHER INFORMATION:

<400> SEQUENCE: 59
aaaaaaattg tctgagccca ggttcgaact ggggaccttt agtgtgtgag actaacgtga     60
taaccaacta caccacccag actgtgtgat atgagatcat gaaagtaatt acttagtaac   120
acgatttaca tgctgcaaat gcatagagcg tgaatcggga tcatttatgt tggaacgaac   180
tgcatgcaga tgatatgata atgatatgac ctcgtcctga tccattctac tctctctgaa    240
```

```
catccgtgaa tagctgaaca gaacagggtc gaagtcaagg tttcgaaaag atctggttac      300
ggttgaacgg tgatgctgcc aacttactga tttagtgtat gatggtgttt ttgaggtgct      360
ccagtggctt ctgtttctat cagctgtccc tcctgttcag ctactgacgg ggtggtgcgt      420
aacggcaaaa gcaccgccgg acatcagcgc tatctctgct ctcactgccg taaaacatgg      480
caactgcagt tcacttacac cgcttctcaa cccggtacgc accagaaaat cattgatatg      540
gccatgaatg gcgttggatg ccgggcaaca gcccgcatta tgggcgttgg cctcaacacg      600
attttacgtc acttaaaaaa ctcaggccgc agtcggtaac ctcgcgcata cagccgggca      660
gtgacgtcat cgtctgcgcg gaaatggacg aacagtgggg ctatgtcggg gctaaatcgc      720
gccagcgctg gctgttttac gcgtatgaca gtctccggaa gacggttgtt gcgcacgtat      780
tcggtgaacg cactatggcg acgctggggc gtcttatgag cctgctgtca cccttgacg      840 tggtgatatg gatgacggat ggctggccgc tgtatgaatc ccgcctgaag ggaaagctgc      900
acgtaatcag caagcgatat acgcagcgaa ttgagcggca taacctgaat ctgaggcagc      960
acctggcacg gctgggacgg aagtcgctgt cgttctcaaa atcggtggag ctgcatgaca     1020
aagtcatcgg gcattatctg aacataaaac actatcaata agttggagtc attacccggt     1080
tgaacttaaa actattattt tgtgtgggca gatatattca aaaaacattc atggaacgct     1140
ttgctaatat atataaagta agattattat tattattaac tagggtttct cgtagaagac     1200
ggacgaactt tggagtggtc gtgccgtcgt ggtggtgtgg ctattattgc ttcagcggca     1260
tgctaaatca aacgtttaac tttgcgtccg agtcgtggag cctggaggaa cttttgcatta     1320 attagcccag ctgactgcgt acgccagcca acgtatttct gatcgagacc gtcgcatgca     1380
cgcatagcgt acactgtcac tgtgtgcaat ataatataat acgcagatta acattatgat     1440
aatataatac gcaacaagct agaccgttcc cgtccgactg cccatttagt taaaacttgc     1500
gttacatgtc agtcacgttc attcgtctga ttgagacgct agctagcttg tgatccggaa     1560
aaaggtctct gcatgcatta ttattggtaa ggtcgtcagc gccgtatata tatgcgtgat     1620
gcatgtgtta taataatatg acaagtaaat tagagattga tgcacgcagt agtaattaag     1680
acaggcatcg taatcccccc ttgttttttgg tttagtagta aatctgcctg ctgctctaag     1740
tagtagttaa aaaaacagag aagcggggtg ggctgcgtat aaatagccgg ccggaaaggg     1800
ggaaacgggc aggcaaacaa caacacacac tcgcgagtcg cgagcacaga tcgaacaggc     1860
aggcggcctc cgatctgtcg ccattgtctc gttgtgttgt cccggaggag cagcagcagg     1920
agcaggagcg atcaggtggg ggtgatgcgc tgatccgttt ctcccttcc ccgccgcgat     1980 ttcctcctct gcttttgttg tccttgtcgc tgctgttcac cccgcctcc tcctgctgcc     2040 gcggcggtgg attctgttct cgtatgctta accagtacca cggaccttct tcccgcaggc     2100
caacgctttg gactcctgga cctacc                                          2126
```

<210> SEQ ID NO 60
<211> LENGTH: 807
<212> TYPE: DNA
<213> ORGANISM: Zea mays
<220> FEATURE:
<221> NAME/KEY: promoter
<222> LOCATION: (1)..(807)
<223> OTHER INFORMATION:

<400> SEQUENCE: 60

```
aattagccca gctgactgcg tacgccagcc aacgtatttc tgatcgagac cgtcgcatgc       60
acgcatagcg tacactgtca ctgtgtgcaa tataatataa tacgcagatt aacattatga      120
```

-continued

```
taatataata cgcaacaagc tagaccgttc ccgtccgact gcccatttag ttaaaacttg      180
cgttacatgt cagtcacgtt cattcgtctg attgagacgc tagctagctt gtgatccgga      240
aaaaggtctc tgcatgcatt attattggta aggtcgtcag cgccgtatat atatgcgtga      300
tgcatgtgtt ataataatat gacaagtaaa ttagagattg atgcacgcag tagtaattaa      360
gacaggcatc gtaatccccc cttgtttttg gtttagtagt aaatctgcct gctgctctaa      420
gtagtagtta aaaaaacaga gaagcggggt gggctgcgta taaatagccg gccggaaagg      480
gggaaacggg caggcaaaca acaacacaca ctcgcgagtc gcgagcacag atcgaacagg      540
caggcggcct ccgatctgtc gccattgtct cgttgtgttg tcccggagga gcagcagcag      600
gagcaggagc gatcaggtgg gggtgatgcg ctgatccgtt tctccccttc ccgccgcga      660 tttcctcctc tgcttttgtt gtccttgtcg ctgctgttca cccccgcctc ctcctgctgc      720
cgcggcggtg gattctgttc tcgtatgctt aaccagtacc acggaccttc ttcccgcagg      780
ccaacgcttt ggactcctgg acctacc                                          807
```

<210> SEQ ID NO 61
<211> LENGTH: 1271
<212> TYPE: DNA
<213> ORGANISM: Zea mays
<220> FEATURE:
<221> NAME/KEY: promoter
<222> LOCATION: (1)..(1271)
<223> OTHER INFORMATION:

<400> SEQUENCE: 61

```
aaatatggtg ttcacatgtg atggtaaata gatactacac atataaataa aggaaatata      60
tttttctcct tttatattat cacttacaaa gtgggtatta cacttgattt caaataaata     120 aaggggtta tttatataaa aatgacgcag catgatcatt gaaattgttg ttttaatata     180
gtaaagatga actgcagtct gccttaaagc tcggtgcatc tgagcatcga ttgcaccgaa      240
gaaagccaca gaaaaagaa agagggaga tggaagaatc tggatagaac attgaactct      300
atttatttct gattttttt catgaacaat ttgagggtgt actgtgctca gcttttgtat      360
aatttggaaa gagagatctg gaatgttttg cgcacacaac tcatgccccg tcctcggatg      420
ctagtagcag catcattttt atgtcacggt gctaataatg acaagggcgg gtagaggatc      480
gatgtgggtt ggaagcagga tgtgtagaag ggaaatgggg tgggggtggg gtgggtggg      540 gtggggttt agggtgggtg cgcatagaga cgagggcgcc tgcgaatgtg atgggttttg      600
tcaaggccgg caggggacag aggttctacc ccaggctggt agtggccggg gttggactcc      660
ccaaccccac acgggcggcc tctgaacctg tacccaaaga aaaaaaaac aacaaaaaca      720 aatctgtgca aattctctcc ctcctcctct ctctttctat ctggaattct ggatgcagtc      780
tgcaaggatg acacaagaac aagaacaacg cgcagtctct ctcctctcta cccttctgct      840
gccatcgatc tcaaagcaag ggaagggaag ggaagccgcc tgaaagccca accaaaccaa      900
accaatcgca tctcccactc gaaaaggca ggcatccaaa acccatccag ggtagaaaga      960
gagagggaga gaacgaggag gttacccatc aatcaatcaa caagagacct actgtatata     1020
gagcagagaa gggggatact aatttgttag taaaactcaa acaaggaagc acttattttg     1080
tgcttgttta gttgcgatca attagcccgc cgccgcgccg ccgcctcctc ctcctatatt     1140
agcccacttc ccttccttcc tttgcagcag caagaactaa ggcttgtccc tttccctctc     1200
ttctcctccc ctccctccg tctcccttcc ccatcttctc tcctggaagc cgcctcggtc     1260
```

```
ggacccggac a                                                           1271

<210> SEQ ID NO 62
<211> LENGTH: 732
<212> TYPE: DNA
<213> ORGANISM: Zea mays
<220> FEATURE:
<221> NAME/KEY: promoter
<222> LOCATION: (1)..(732)
<223> OTHER INFORMATION:

<400> SEQUENCE: 62 ggtggggtt tagggtgggt gcgcatagag acgagggcgc ctgcgaatgt gatgggtttt        60
gtcaaggccg gcaggggaca gaggttctac cccaggctgg tagtggccgg ggttggactc      120
cccaaaccca cacgggcggc ctctgaacct gtacccaaag aaaaaaaaaa caacaaaaac      180
aaatctgtgc aaattctctc cctcctcctc tctctttcta tctggaattc tggatgcagt      240
ctgcaaggat gacacaagaa caagaacaac gcgcagtctc tctcctctct acccttctgc      300
tgccatcgat ctcaaagcaa gggaagggaa gggaagccgc ctgaaagccc aaccaaacca      360
aaccaatcgc atctcccact cgaaaaaggc aggcatccaa acccatcca gggtagaaag       420 agagagggag agaacgagga ggttacccat caatcaatca acaagagacc tactgtatat      480
agagcagaga aggggatac taatttgtta gtaaaactca aacaaggaag cacttatttt       540
gtgcttgttt agttgcgatc aattagcccg ccgccgcgcc gccgcctcct cctcctatat      600
tagcccactt cccttccttc ctttgcagca gcaagaacta aggcttgtcc ctttccctct      660
cttctcctcc cctcccctcc gtctcccttc cccatcttct ctcctggaag ccgcctcggt      720
cggacccgga ca                                                          732

<210> SEQ ID NO 63
<211> LENGTH: 27
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(27)
<223> OTHER INFORMATION:

<400> SEQUENCE: 63
tgtgcgcggc gttgggcgcc agcccag                                           27

<210> SEQ ID NO 64
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(39)
<223> OTHER INFORMATION:

<400> SEQUENCE: 64
ggatccagat ctgccggtgg tggtggtaga gggaacagg                              39

<210> SEQ ID NO 65
<211> LENGTH: 27
<212> TYPE: DNA
<213> ORGANISM: artificial sequence
<220> FEATURE:
<223> OTHER INFORMATION: a fully synthesized primer
```

```
<220> FEATURE:
<221> NAME/KEY: misc_feature
<222> LOCATION: (1)..(27)
<223> OTHER INFORMATION:

<400> SEQUENCE: 65
tcggagaggc ggaggccgcc gtgtctg                                              27

<210> SEQ ID NO 66
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(39)
<223> OTHER INFORMATION:

<400> SEQUENCE: 66
ggatccagat ctggtaggtc caggagtcca aagcgttgg                                 39

<210> SEQ ID NO 67
<211> LENGTH: 28
<212> TYPE: DNA
<213> ORGANISM: artificial sequence
<220> FEATURE:
<223> OTHER INFORMATION: a fully synthesized primer
<220> FEATURE:
<221> NAME/KEY: misc_feature
<222> LOCATION: (1)..(28)
<223> OTHER INFORMATION:

<400> SEQUENCE: 67
acatcgtcca cgtggtacac ctcctcgg                                             28

<210> SEQ ID NO 68
<211> LENGTH: 39
<212> TYPE: DNA
<213> ORGANISM: artificial sequence
<220> FEATURE:
<223> OTHER INFORMATION: a fully synthesized primer
<220> FEATURE:
<221> NAME/KEY: promoter
<222> LOCATION: (1)..(39)
<223> OTHER INFORMATION:

<400> SEQUENCE: 68
ggatccagat cttgtccggg tccgaccgag gcggcttcc                                 39
```